US012251420B2

(12) United States Patent
Lelkes et al.

(10) Patent No.: US 12,251,420 B2
(45) Date of Patent: *Mar. 18, 2025

(54) SOY-DERIVED BIOACTIVE PEPTIDES FOR USE IN COMPOSITIONS AND METHODS FOR WOUND HEALING, TISSUE ENGINEERING, AND REGENERATIVE MEDICINE

(71) Applicant: Temple University—Of The Commonwealth System of Higher Education, Philadelphia, PA (US)

(72) Inventors: Peter I. Lelkes, Cherry Hill, NJ (US); Yah-el H. Har-el, Philadelphia, PA (US); Cezary Marcinkiewicz, King of Prussia, PA (US); Philip Lazarovici, Jerusalem (IL); Sogol Moaiyed Baharlou, Philadelphia, PA (US); Jonathan A. Gerstenhaber, Philadelphia, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/392,024

(22) Filed: Aug. 2, 2021

(65) Prior Publication Data

US 2022/0211804 A1 Jul. 7, 2022

Related U.S. Application Data

(63) Continuation of application No. 15/746,508, filed as application No. PCT/US2016/043388 on Jul. 21, 2016, now Pat. No. 11,077,169.

(60) Provisional application No. 62/335,195, filed on May 12, 2016, provisional application No. 62/256,480, filed on Nov. 17, 2015, provisional application No. 62/234,266, filed on Sep. 29, 2015, provisional application No. 62/195,386, filed on Jul. 22, 2015.

(51) Int. Cl.

| | |
|---|---|
| ***A61L 27/38*** | (2006.01) |
| ***A61F 2/02*** | (2006.01) |
| ***A61K 9/70*** | (2006.01) |
| ***A61K 38/16*** | (2006.01) |
| ***A61K 47/42*** | (2017.01) |
| ***A61L 15/26*** | (2006.01) |
| ***A61L 15/32*** | (2006.01) |
| ***A61L 15/44*** | (2006.01) |
| ***A61L 26/00*** | (2006.01) |
| ***A61L 27/18*** | (2006.01) |
| ***A61L 27/22*** | (2006.01) |
| ***A61L 27/52*** | (2006.01) |
| ***A61L 27/54*** | (2006.01) |
| ***A61P 17/02*** | (2006.01) |

(52) U.S. Cl.

CPC ............ *A61K 38/168* (2013.01); *A61L 15/26* (2013.01); *A61L 15/32* (2013.01); *A61L 15/44* (2013.01); *A61L 26/0019* (2013.01); *A61L 26/0047* (2013.01); *A61L 26/0066* (2013.01); *A61L 26/008* (2013.01); *A61L 27/18* (2013.01); *A61L 27/222* (2013.01); *A61L 27/227* (2013.01); *A61L 27/52* (2013.01); *A61L 27/54* (2013.01); *A61P 17/02* (2018.01); *A61L 2300/252* (2013.01); *A61L 2300/412* (2013.01)

(58) Field of Classification Search

CPC ..... A61K 38/168; A61L 27/18; A61L 27/222; A61L 27/52; A61L 27/54; A61L 2300/412; A61P 17/02

See application file for complete search history.

(56) References Cited

U.S. PATENT DOCUMENTS

2012/0058090 A1* 3/2012 Lelkes .................... A61L 15/40 530/370

FOREIGN PATENT DOCUMENTS

WO WO2012120516 * 9/2012 ............... A61K 9/70

OTHER PUBLICATIONS

Aqueous definition, the Free Dictionary, 3 pp., accessed Jul. 7, 2019, at URL thefreedictionary.com/aqueous (Year: 2019).*

Har-el et al., "Electrospun soy protein scaffolds as wound dressings: Enhanced reepithelialization in a porcine model of wound healing," Wound Medicine 5:9-15 (online May 2014 (Year: 2014).*

Lin, "Electrospun Soy Protein-based Scaffolds for Skin Tissue Engineering and Wound Healing," PhD Dissertation, Drexel University, 227 pages (2011).*

Malhotra et al, "The effect of surfactants on the solubility, zeta potential, and viscosity of soy protein isolates," Food Hydrocolloids 18:101-108 (2004) (Year: 2004).*

* cited by examiner

*Primary Examiner* — Julie Ha
*Assistant Examiner* — Kristina M Hellman
(74) *Attorney, Agent, or Firm* — Riverside Law LLP

(57) ABSTRACT

Compositions and methods for the promotion of wound healing and tissue regeneration are described. The compositions and methods make use of water-soluble soy protein isolates (WSsoy), Fraction 5, Fraction 9, and/or bioactive peptide components of soy protein isolates. The invention also relates to the unexpected discovery that purified WSsoy forms gel-like matrices when suspended within certain concentration ranges in an aqueous environment. The compositions of the invention comprising WSsoy promote natural healing and have a low risk profile.

4 Claims, 29 Drawing Sheets

Specification includes a Sequence Listing.

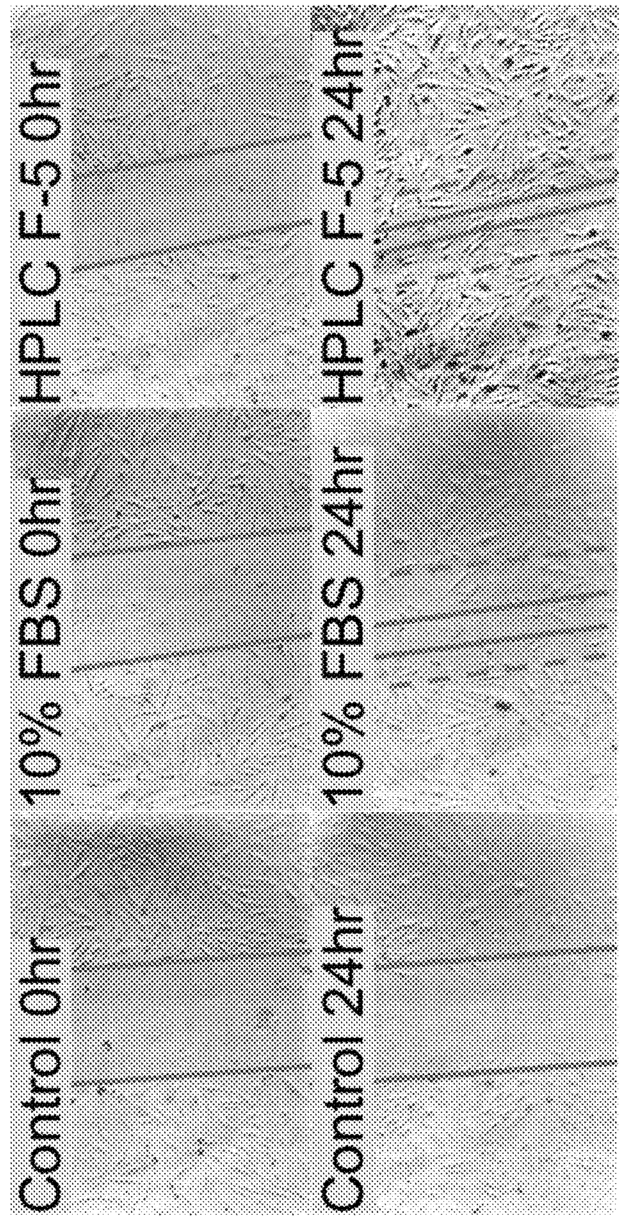
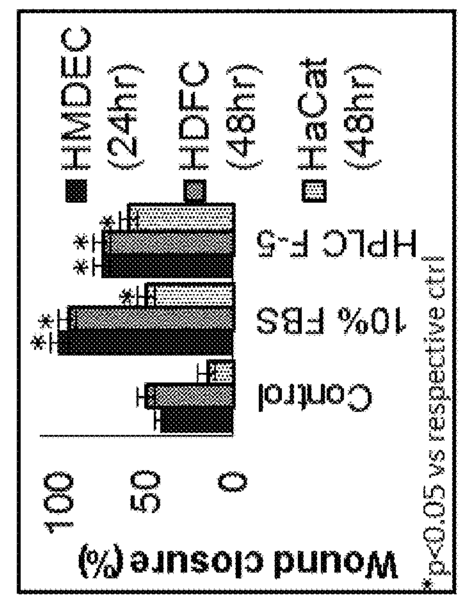
Fig. 3

β-conglycinin subunit α', partial peptides identified by proteomics in fraction SB9-BCF9-4

CS-1 fragment of fibronectin

```
                10        20        30        40        50        60        70        80        90
SEQ ID NO. 3 VEEEEECEEGQIPRPRPQHPERERQQHGEKEEDEGEQPRPFPFPRPRQPHQEEEHEQKEEHEWHRKEEKEGGKGSEEEQDEREHPRPHQP

                100       110       120       130       140       150       160       170       180
             HQKEEEKHEWQHKQEKHQGKESEEEEEDQDEDEEQDKESQESEGSESQREPRRHKNKNPFHFNSKRFQTLFKNQYGHVRVLQRFNKRSQQ
SEQ ID NO. 4 -------------------------------------------------------------------------------------SQQ

                190       200       210       220       230       240       250       260       270
             LQNLRDYRILEFNSKPNTLLLPHHADADYLIVILNGTALLTLVNNDDRDSYNLQSGDALRVPAGTTYYVVNPDNDENLRMITLAIPVNKP
             LQNLR-------------------------------------------DSYNLQSGDALRVPAGTTYYVVNPDNDENLRMITLAIPVNKP
SEQ ID NO. 5 ------------------------------------------------------LQSGDALR--------------------------

                280       290       300       310       320       330       340       350       360
             GRFESFFLSSTQAQQSYLQGFSKNILEASYDTKFEEINKVLFGREEGQQQGEERLQESVIVEISKKQIRELSKHAKSSSRKTISSEDKPF
             GR----------------------NILEASYDTK-------VLFGREEGQQQGEER-------------------------TISSEDKPF
             ------------------------NILEASYDTKFEEINK-------------------------------------------KTISSEDKPF

                370       380       390       400       410       420       430       440       450
             NLRSRDPIYSNKLGKLFEITPEKNPQLRDLDVFLSVVDMNEGALFLPHFNSKAIVVLVINEGEANIELVGIKEQQQRQQQEFQPLEVRKY
             NLR--------DELPQLVTLPHPSLHGPEILDVPST
             NLR

                460       470       480       490       500       510       520       530       540
             RAELSEQDIFVIPAGYPVVVNATSDLNFFAFGINAENNQRNFLAGSKDNVISQIPSQVQELAFPGSAKDIENLIKSQSESYFVDAQPQQK

                550
             EEGNKGRKGPLSSILRAFY

             CS-1
SEQ ID NO. 6 DELPQLVTLPHPSLHGPEILDVPST
```

Fig. 12

| | SDS-PAGE Spot ID | MW (kDa, SDS-PAGE) | MS/MS Tryptic peptide ion sequencing m/z | z | Peptide sequence | MASCOT Score | Best NCBI match | Protein/Protein family |
|---|---|---|---|---|---|---|---|---|
| SEQ ID NO. 7 | BCF5-4A | 35 | 747.0 | 3 | QHGNTGGLYYGTDTADTGTGPR | 78 | Glycine max CAG28964 | putative dehydrin |
| | | | | | | | Glycine max KRH47369 | hypothetical protein GLYMA_07G024700 |
| SEQ ID NO. 8 | | | 450.3 | 2 | VGATVMINI | *de novo* | | |
| SEQ ID NO. 9 | | | 745.4 | 3 | (761.6)YYGTNTADTGTGPR | *de novo* | Glycine max CAG28965 | putative dehydrin |
| SEQ ID NO. 10 | | | 825.3 | 2 | (1299.1)HAAWTYVATR | *de novo* | Glycine max CAG28965 | putative dehydrin |
| SEQ ID NO. 11 | BCF5-4B | 25 | 593.8 | 2 | QGETVVPGGTGGK | *de novo* | Glycine max NP_001237186 | protein SLE3 |
| SEQ ID NO. 12 | | | 590.8 | 2 | KVDEYGNVEK | 196 | Glycine max CAE47770 | dehydrin |
| SEQ ID NO. 13 | | | 510.2 | 3 | HHGTTGVYGIDTDR | | | |
| SEQ ID NO. 14 | | | 727.0 | 3 | QTDEYGNPVHAASVTYVATR | | | |
| SEQ ID NO. 15 | | | 745.3 | 3 | QHGNIGGPYYGTNTADTGTGPR | | | |
| SEQ ID NO. 16 | | | 465.7 | 2 | QCAHVCR | 140 | Glycine max XP_003525155 | defensin-like protein 1 |
| SEQ ID NO. 17 | | | 493.7 | 2 | CFCSRPC | | | |
| SEQ ID NO. 18 | | | 548.8 | 2 | SDGFIGGQCR | | | |
| SEQ ID NO. 19 | | | 763.9 | 2 | QIVTVEGGLSVISPK | 98 | Glycine max CAA37044 | glycinin |
| SEQ ID NO. 20 | | | 580.3 | 3 | QQHDAIGVYPGIDIGR | 85 | Glycine max NP_001238578 | maturation-associated protein |
| SEQ ID NO. 21 | | | 747.0 | 3 | QHGNTGGLYYGTDTADTGTGPR | | | |

Fig. 16

| | SDS-PAGE Spot ID | MW (kDa, SDS-PAGE) | MS/MS Tryptic peptide ion sequencing m/z | z | Peptide sequence | MASCOT Score | Best NCBI match | Protein/Protein family |
|---|---|---|---|---|---|---|---|---|
| SEQ ID NO. 22 | BCF5-4C | 12 | 488.3 | 2 | ELMoxNLAIR | 162 | Glycine max NP_001237974 | uncharacterized protein |
| SEQ ID NO. 23 | | | 698.3 | 2 | LGPMoxIGCDLSSDD | | | |
| SEQ ID NO. 24 | | | 856.4 | 2 | CRLGPMoxIGCDLSSDD | | | |
| SEQ ID NO. 25 | BCF5-4D | 10 | 465.7 | 2 | QCAHVCR | 164 | Glycine max XP_003525155 | defensin-like protein 1 |
| SEQ ID NO. 26 | | | 493.7 | 2 | CFCSRPC | | | |
| SEQ ID NO. 27 | | | 548.7 | 2 | SDGFIGGQCR | | | |
| SEQ ID NO. 28 | | | 541.2 | 3 | CLFDRQCAHVCR | | | |
| SEQ ID NO. 29 | | | 748.3 | 2 | SMoxPPQCSCEDIR | 115 | Glycine max 0404180A | inhibitor DII, trypsin |
| SEQ ID NO. 30 | | | 574.2 | 3 | CLDTNDFCYKPCK | | | |
| SEQ ID NO. 31 | | | 475.7 | 2 | CGVNIPYK | 47 | Glycine max XP_003516421 | non-specific lipid-transfer protein 1-like |
| SEQ ID NO. 32 | | | 670.9 | 3 | DEYSKPCCDLCMoxCTR | 101 | Glycine max 1PI2_A | Proteinase Inhibitor |
| SEQ ID NO. 33 | BCF5-5 | 12 | 698.3 | 2 | LGPMoxIGCDLSSDD | 175 | Glycine max NP_001237974 | uncharacterized protein |
| SEQ ID NO. 34 | | | 704.3 | 2 | IMoxDNQSEQLEGK | | | |
| SEQ ID NO. 35 | | | 555.3 | 3 | KQMoxERELMNLAIR | | | |
| SEQ ID NO. 36 | | | 856.4 | 2 | CRLGPMoxIGCDLSSDD | | | |
| SEQ ID NO. 37 | | | 678.3 | 3 | CCSEMoxSELKSPICQCK | | | |
| SEQ ID NO. 38 | | | 763.9 | 2 | QIVTVEGGLSVISPK | 79 | Glycine max CAA37044 | glycinin |

Fig. 16 cont.

| | Spot ID | Mw | m/z | z | Peptide sequence | Score | *NCBI/TrEmbl* | Protein family |
|---|---|---|---|---|---|---|---|---|
| SEQ ID NO. 39 | BCF9-4 | | 494.3 | 2 | SQQLQNLR | 837 | *Glycine max* BAA74452 | α' subunit of β-conglycinin, partial |
| SEQ ID NO. 40 | | | 577.3 | 2 | NILEASYDTK | | | |
| SEQ ID NO. 41 | | | 669.8 | 2 | DSYNLQSGDALR | | | |
| SEQ ID NO. 42 | | | 469.6 | 3 | TISSEDKPFNLR | | | |
| SEQ ID NO. 43 | | | 470.6 | 3 | MITLAIPVNKPGR | | | |
| SEQ ID NO. 44 | | | 512.3 | 3 | KTISSEDKPFNLR | | | |
| SEQ ID NO. 45 | | | 589.0 | 3 | VLFGREEGQQQGEER | | | |
| SEQ ID NO. 46 | | | 638.7 | 3 | NILEASYDTKFEEINK | | | |
| SEQ ID NO. 47 | | | 1069.0 | 2 | VPAGTTYYVVNPDNDENLR | | | |
| SEQ ID NO. 48 | | | 430.2 | 2 | LQSGDALR | 571 | *Glycine max* BAA23360 | α subunit of β-conglycinin, partial |
| SEQ ID NO. 49 | | | 465.0 | 3 | LITLAIPVNKPGR | | | |
| SEQ ID NO. 50 | | | 1076.5 | 2 | VPSGTTYYVVNPDNNENLR | | | |
| SEQ ID NO. 51 | | | 699.9 | 2 | ISTLNSLTLPALR | 401 | *Glycine max* CAA55977 | Gy5 |
| SEQ ID NO. 52 | | | 688.0 | 3 | AIPSEVLSNSYNLGQSQVR | | | |
| SEQ ID NO. 53 | | | 695.3 | 3 | FNECQLNNLNALEPDHR | | | |
| SEQ ID NO. 54 | BCF9-5 | | 430.2 | 2 | LQSGDALR | 806 | *Glycine max* BAA23360 | α subunit of β-conglycinin, partial |
| SEQ ID NO. 55 | | | 478.3 | 2 | SPQLQNLR | | | |
| SEQ ID NO. 56 | | | 577.3 | 2 | NILEASYDTK | | | |
| SEQ ID NO. 57 | | | 696.4 | 2 | LITLAIPVNKPGR | | | |
| SEQ ID NO. 58 | | | 703.9 | 2 | TISSEDKPFNLR | | | |
| SEQ ID NO. 59 | | | 591 | 3 | LQESVIVEISKEQIR | | | |
| SEQ ID NO. 60 | | | 597.6 | 3 | VLFSREEGQQQGEQR | | | |
| SEQ ID NO. 61 | | | 1076.5 | 2 | VPSGTTYYVVNPDNNENLR | | | |
| SEQ ID NO. 62 | | | 494.3 | 2 | SQQLQNLR | 369 | *Glycine max* BAA74452 | α' subunit of β-conglycinin, partial |
| SEQ ID NO. 63 | | | 475.9 | 3 | MoxITLAIPVNKPGR | | | |
| SEQ ID NO. 64 | | | 713.0 | 3 | VPAGTTYYVVNPDNDENLR | | | |

Fig. 17

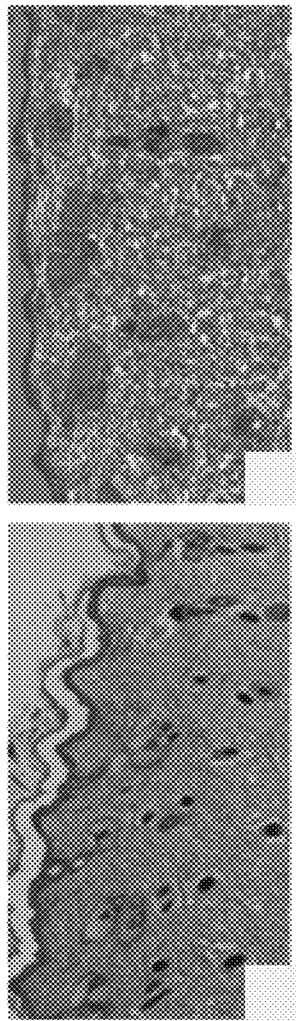
Fig. 18A
Fig. 18B
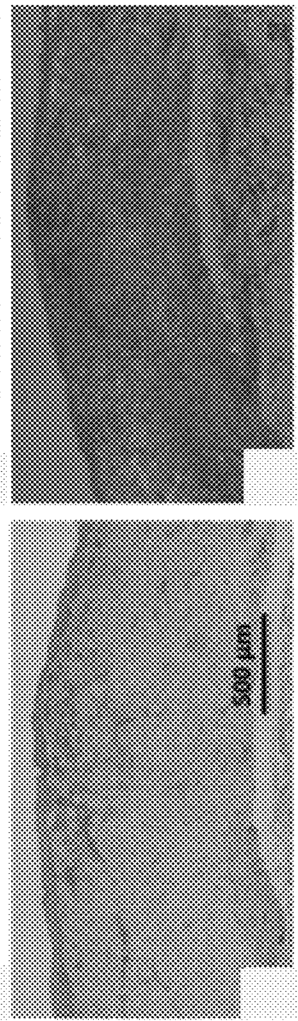
Fig. 18C
Fig. 18D
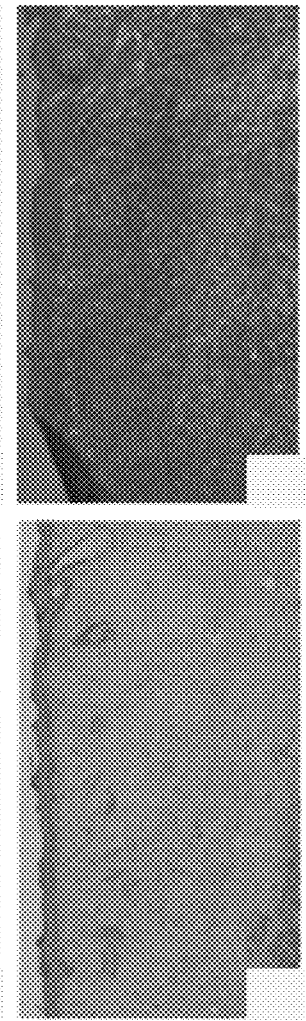
Fig. 18E
Fig. 18F
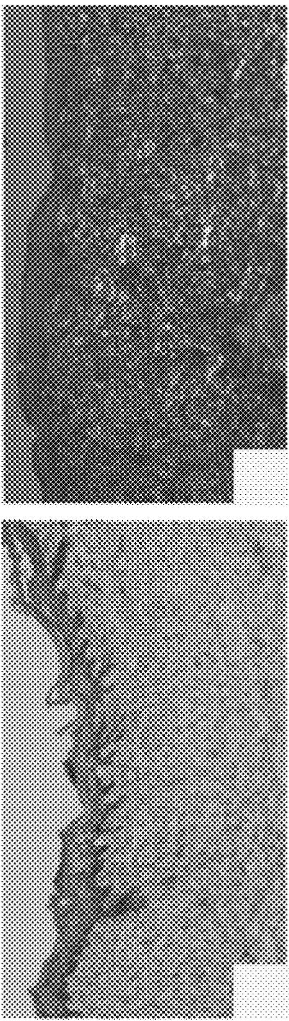
Fig. 18G
Fig. 18H SWM – Soy Wound Matrix, Oasis® - Acellular skin substitute

SOY-DERIVED BIOACTIVE PEPTIDES FOR USE IN COMPOSITIONS AND METHODS FOR WOUND HEALING, TISSUE ENGINEERING, AND REGENERATIVE MEDICINE

CROSS-REFERENCE TO RELATED APPLICATIONS

This application claims priority to U.S. Provisional Patent Application No. 62/195,386 filed Jul. 22, 2015; U.S. Provisional Patent Application No. 62/234,266 filed Sep. 29, 2015; U.S. Provisional Patent Application No. 62/256,480 filed Nov. 17, 2015; and U.S. Provisional Patent Application No. 62/335,195 filed May 12, 2016, the contents of which are incorporated by reference herein in their entirety.

BACKGROUND OF THE INVENTION

Non-healing cutaneous wounds comprise a significant source of patient morbidity and financial burden for the US healthcare system. Full-thickness wounds are characterized, (Driver, V. R., et al., 2010, *J Am Podiatr Med Assoc* 100, 335-341; Gordon, M. D., et al., 2010, *J. Burn Care Rehabil* 25, 388-410), by the complete destruction of some of the critical epithelial-regenerative elements (stem/progenitor cells) found in skin hair follicles and sweat glands.

Products used in the clinic mostly address immediate needs, such as the provision of a mechanical barrier, prevention of moisture loss and prevention of bacterial infection until wound closure can be achieved. (Skorkowska-Telichowska, K., et al., 2013, *J Am Acad Dermatol* 38, e117-126). Recent research has focused on the development of acellular and cellular bioactive wound matrices for improving the wound healing processes, (Demidova-Rice, T. N. et al., 2012, *Advances in Skin & Wound Care,* 25, 304-314; Mayet, N., et al., 2014, *Journal of Pharmaceutical Sciences* 103, 2211-2230) with emphasis on reducing scar formation and promoting regeneration of skin appendages (Sun, G., et al., 2011, *Proceedings of the National Academy of Sciences of the United States of America* 108, 20976-20981; Bonvallet, P. P., et al., 2014, *Tissue engineering. Part A* 20, 2434-2445). Acellular bioactive wound matrices are advantageous because they can enhance wound healing in the absence of exogenous cells, thus replacing more expensive cellularized wound matrices with their associated limitations of long culture times, short shelf lives, and immunogenicity. In spite of significant progress, no currently commercially available product meets the "ideal" properties of a product directly modulating the cells involved in the wound healing process—leaving a critical gap in treatment options (Pereira, R. F., et al., 2013, *Nanomedicine* (*Lond*) 8 603-621; Shevchenko, R. V., et al., 2010, *J R Soc Interface* 7, 229-258).

Currently there are several types of bioactive wound matrices in clinical use; however none of them has been able to induce full regeneration of skin tissue. In addition, some of the most promising cell-based wound matrices are prohibitively expensive and their handling is complicated by the presence of live cells and the short shelf lives of the products. The challenge is to identify inexpensive natural biomaterials that can be turned into pharmaceutical preparations including acellular wound matrices, which will enhance the complex biological processes responsible for cutaneous wound healing and will be easy to handle with long shelf-lives, thus providing novel opportunities for tissue repair and regeneration.

Promoting wound healing by a regenerative engineering approach traditionally relies on the creation of three-dimensional scaffolds, which serve as extracellular matrix (ECM) surrogates that will guide skin cell adhesion, growth, and differentiation. Recently others and us have begun to investigate the potential of soy protein isolates (SPI), a plant-derived 'green', renewable, and inexpensive natural biomaterial, for drug delivery and wound healing, (Har-el, Y., et al., 2014, *Wound Medicine* 5, 9-15; Peles, Z., et al., 2013, *J Tissue Eng Regen Med* 7, 401-412; Santos, T. C., et al., 2013, *Tissue Eng Part A* 19, 860-869). However, conventional SPI is soluble only in a strong acid or in an aggressive and expensive organic solvent (1,1,1,3,3,3-Hexafluoro-2-propanol), which hinders its large-scale commercial production and/or biomedical use because of the costs and the potential for corrosive solvent residues. Moreover, to date, no one has as yet studied the mechanism(s) by which SPI enhances wound healing in small and large animal models. The lack of detailed mechanistic information on the cellular mechanisms of action of SPI which are involved in enhanced wound healing is another barrier to the development of SPI as an optimal wound matrix.

There is a substantial unmet clinical need for a product that can expedite natural healing to a great number of patients while reducing the total cost of care, without the issues associated with currently used animal and human derived materials. The present invention meets this need.

SUMMARY OF THE INVENTION

In one aspect, the present invention provides a composition for inducing wound healing and tissue regeneration, wherein the composition comprises a bioactive peptide component of a soy protein isolate (SPI).

In one embodiment, the composition comprises Fraction 5. In one embodiment, Fraction 5 comprises a protein fraction eluted during separation of WSsoy using reverse phase-high pressure liquid chromatography (RP-HPLC) using C18 with a linear gradient of elution (0-80% acetonitrile (ACN) over 45 minutes, wherein Fraction 5 has a retention time of about 25-35 minutes. In one embodiment, Fraction 5 has as zeta potential of about 17.9 mV.

In one embodiment, the composition comprises Fraction 9. In one embodiment, Fraction 9 comprises a protein fraction eluted during separation of WSsoy using reverse phase-high pressure liquid chromatography (RP-HPLC) using C18 with a linear gradient of elution (0-80% acetonitrile (ACN) over 45 minutes, wherein Fraction 9 has a retention time of about 35-40 minutes. In one embodiment, Fraction 9 has as zeta potential of about 34.2 mV.

In one embodiment, the composition comprises a powder, gel, lotion, film, solution, spray, or scaffold.

In one aspect, the present invention provides a composition for inducing wound healing and tissue regeneration, wherein the composition comprises water soluble soy protein isolate (WSsoy).

In one aspect, the present invention provides a method for promoting wound healing and tissue regeneration in a subject in need thereof, the method comprising administering a composition comprising a WSsoy and/or a bioactive peptide component of SPI to a treatment site on the subject.

In one aspect, the present invention provides a scaffold for inducing wound healing and tissue regeneration, wherein the scaffold comprises a bioactive peptide component of a soy protein isolate (SPI).

In one embodiment, the scaffold comprises Fraction 5. In one embodiment, Fraction 5 comprises a protein fraction eluted during separation of WSsoy using reverse phase-high pressure liquid chromatography (RP-HPLC) using C18 with a linear gradient of elution (0-80% acetonitrile (ACN) over 45 minutes, wherein Fraction 5 has a retention time of about 25-35 minutes. In one embodiment, Fraction 5 has as zeta potential of about 17.9 mV.

In one embodiment, the scaffold comprises Fraction 9. In one embodiment, Fraction 9 comprises a protein fraction eluted during separation of WSsoy using reverse phase-high pressure liquid chromatography (RP-HPLC) using C18 with a linear gradient of elution (0-80% acetonitrile (ACN) over 45 minutes, wherein Fraction 9 has a retention time of about 35-40 minutes. In one embodiment, Fraction 9 has as zeta potential of about 34.2 mV.

In one embodiment, the scaffold comprises electroprocessed fibers. In one embodiment, the electroprocessed fibers comprises the bioactive peptide component of SPI. In one embodiment, the electroprocessed fibers comprise a synthetic polymer. In one embodiment, the synthetic material polymer is selected from the group consisting of poly (epsilon-caprolactone) (PCL), poly (lactic acid) (PLA), poly (glycolic acid) (PGA), copolymers poly (lactide-co-glycolide) (PLGA), polyaniline, poly(ethylene oxide) (PEO), and any combination thereof.

In one embodiment, the electroprocessed fibers comprise Fraction 9 acting as ligand for $\alpha9\beta1$ integrin. In one embodiment, the scaffold further comprises Fraction 5 in soluble form. In one embodiment, Fraction 5 is loaded within a drug delivery vehicle embedded in the scaffold.

In one embodiment, the scaffold comprises a hydrogel comprising the bioactive component of SPI. In one embodiment, the hydrogel comprises gelatin crosslinked with genipin.

In one aspect, the present invention provides a scaffold for inducing wound healing and tissue regeneration, wherein the scaffold comprises WSsoy. In one embodiment, the scaffold comprises electroprocessed fibers comprising WSsoy. In one embodiment, the electroprocessed fibers comprise a synthetic polymer. In one embodiment, the synthetic material polymer is selected from the group consisting of poly (epsilon-caprolactone) (PCL), poly (lactic acid) (PLA), poly (glycolic acid) (PGA), copolymers poly (lactide-co-glycolide) (PLGA), polyaniline, poly(ethylene oxide) (PEO), and any combination thereof. In one embodiment, the scaffold comprises a hydrogel comprising WSsoy.

In one aspect, the present invention provides a method of promoting wound healing and tissue regeneration in a subject in need thereof, the method comprising administering a scaffold comprising WSsoy and/or a bioactive peptide component of SPI to a treatment site on the subject.

In one aspect, the invention provides a method of treating a wet wound, comprising the steps of applying an effective amount of a dry composition comprising purified water-soluble soy protein isolate (WSsoy) to the wet wound, wherein the dry WSsoy, upon contacting the moisture in the wet wound, self-assembles into a semi-liquid matrix. In one embodiment, the amount of applied dry WSsoy is between 1 and 100 mg per 1 $cm^2$ of wound. In one embodiment, the dry WSsoy is applied with a thickness between 50 and 5000 μm.

In one aspect, the invention provides a method of treating a wound, comprising the steps of applying an effective amount of WSsoy in a liquid carrier to the wound, wherein the WSsoy self-assembles into a semi-liquid matrix in the liquid carrier. In one embodiment, the WSsoy has a concentration between 1 and 200 mg per 1 mL of liquid carrier. In one embodiment, the amount of WSsoy in liquid carrier is between 0.1 and 1 mL per 1 $cm^2$ of wound. In one embodiment, the water-soluble soy protein isolate in liquid carrier is applied with a thickness between 50 and 5000 μm. In one embodiment, the method of application is by direct electroprocessing onto the wound.

In one aspect, the invention provides a composition for rapid wound healing comprising WSsoy and at least one active agent. In one embodiment, the composition comprises dry WSsoy particles. In one embodiment, the particles are between 1 and 1000 μm in diameter. In one embodiment, the at least one active agent is selected from the group consisting of: an anesthetic, an antiallergic, an antihistamine, an antipruritic, a muscle relaxant, an analgesic, an antipyretic, a vitamin, an antimicrobial, an antiseptic, a disinfectant, a fungicide, an ectoparasiticide, an antiparasitic, an alkaloid, a salt, an ion, an anti-inflammatory, a wound healing agent, a plant extract, a growth factor, a polycarbonate, an extracellular matrix (ECM) constituent, an emollient, an antibacterial, an antiviral, a tranquilizer, an antitussive, a nanoparticle, and combinations thereof.

In one embodiment, the composition further comprises a dry component selected from the group consisting of: gelatin, Matrigel, keratin, collagen, elastin, fibrin, hyaluronic acid, glycosaminoglycan, proteoglycan, fibronectin, vitronectin, laminin, chitosan, polyurethane, polysiloxane or silicone, polyethylene, polyvinyl pyrrolidone, poly(2-hydroxy ethyl methacrylate), poly(N-vinyl pyrrolidone), polymethyl methacrylate, polyvinyl alcohol, polyacrylic acid, polyacrylamide, polyethylene-co-vinyl acetate, polyethylene glycol, polyethylene oxide, polymethacrylic acid, polylactide (PLA), polyglycolide (PGA), poly(lactic-co-glycolic acid) (PLGA), polystyrene, polyanhydride, polyorthoester, polycarbonate, and combinations thereof.

In one aspect, the invention provides a composition for rapid wound healing comprising WSsoy in a liquid carrier. In one embodiment, the liquid carrier is a pharmaceutically acceptable carrier. In one embodiment, the composition comprises between 1 and 200 mg of WSsoy per 1 mL of liquid carrier. In one embodiment, the composition further comprises an agent selected from the group consisting of: an anesthetic, an antiallergic, an antihistamine, an antipruritic, a muscle relaxant, an analgesic, an antipyretic, a vitamin, an antimicrobial, an antiseptic, a disinfectant, a fungicide, an ectoparasiticide, an antiparasitic, an alkaloid, a salt, an ion, an anti-inflammatory, a wound healing agent, a plant extract, a growth factor, a polycarbonate, an extracellular matrix (ECM) constituent, an emollient, an antibacterial, an antiviral, a tranquilizer, an antitussive, a nanoparticle, and combinations thereof.

In one embodiment, the composition further comprises a component selected from the group consisting of: gelatin, Matrigel, keratin, collagen, elastin, fibrin, hyaluronic acid, glycosaminoglycan, proteoglycan, fibronectin, vitronectin, laminin, chitosan, polyurethane, polysiloxane or silicone, polyethylene, polyvinyl pyrrolidone, poly(2-hydroxy ethyl methacrylate), poly(N-vinyl pyrrolidone), polymethyl methacrylate, polyvinyl alcohol, polyacrylic acid, polyacrylamide, polyethylene-co-vinyl acetate, polyethylene glycol, polyethylene oxide, polymethacrylic acid, polylactide (PLA), polyglycolide (PGA), poly(lactic-co-glycolic acid) (PLGA), polystyrene, polyanhydride, polyorthoester, polycarbonate, and combinations thereof. In one embodiment, the composition is electrospun into a fiber, a sheet, or a fabric.

In one aspect, the invention provides a kit for treating wounds, comprising at least one amount of a WSsoy composition and at least one amount of a liquid carrier. In one embodiment, the invention further comprises a method of mixing the at least one amount of a WSsoy composition and the at least one amount of a liquid carrier.

In one aspect, the invention provides a composition for rapid wound healing, comprising Bioactive Component Fraction (BCF) 5-5.

In one aspect, the invention provides a composition for rapid wound healing, comprising BCF 9-4.

In one aspect, the invention provides a composition for rapid wound healing, comprising β-conglycinin.

In one aspect, the invention provides a composition for rapid wound healing, comprising a fragment of β-conglycinin having a LDV motif.

In one aspect, the invention provides a composition for rapid wound healing, comprising a peptide or fragment thereof having a LDV motif.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A is a macroscopic view of electrospun membrane, and SEM of fibers of SPI (top) and WSsoy (bottom) FIG. 1B is a macroscopic view of estrogen receptor dependent transcription in T47D cells transfected with ERE reporter gene (Hirsch, K. et al., 2007, *Breast Cancer Res Treat,* 104, 221-230) treated with positive control compounds and SPI and WSsoy ethanol extracts indicative of the presence or absence of phytoestrogens. FIG. 1C depicts inhibition of SPI-induced wound closure in HaCaT epithelial cells by estrogen receptor antagonist Fulvestrant (ICI-182780). The pro-migratory activity of the ethanol extract of SPI (10 μM) was inhibited by 10 μM antagonist. Ethanol extract of WSsoy, lacking ERE activity was without effect in wound closure.

FIG. 3 depicts the results of experiments demonstrating that pro-migratory activity in skin cell scratch assay was detected in Fraction 5. A scratch wound of 1 mm was performed on monolayers of HMDEC, HDFC, and HaCaT cells. Cultures were incubated for 48 hours with fractions (50 ug/mL) in medium (0.1% FBS). Percent of wound closure was determined by quantitative image analysis.

FIG. 7A. Re-chromatography of Fraction 9 under the same conditions as described in FIG. 2 except for using a "flatter" gradient of ACN (40-80% over 120 min). Collected subfractions were named 9-1 to 9-5. Shaded area indicates proteins that promote α9+ cell adhesion. Inset: SDS-PAGE, under reduced conditions stained with Coomassie Blue. Marked area: band analyzed by proteomics. FIG. 7B: Analysis of subfractions 9 in cell adhesion assay obtained after 2nd step of RP-HPLC. Experiment was performed using α9+ cells as described in FIG. 5. Error bars from duplicate experiments. (*) $p<0.05$ compared with binding to 9-1.

FIG. 10A and FIG. 10B: Day 7 post wounding. FIG. 10C and FIG. 10D: 14 days pots wounding. For details see text. E: regenerating epithelial lining; A: regenerating appendages; WM: wound margin; S: scab; GT: granulation tissue; white arrow: blood vessels. Scale bars represent 200 μm.

FIG. 12 depicts the results of proteomic analysis comparing the amino acid sequences of β-conglycinin subunit α' chain, partial with sequences of peptides found in Fraction 9. Analogical fragment of fibronectin (CS-1 peptide) also included.

Figure 14:
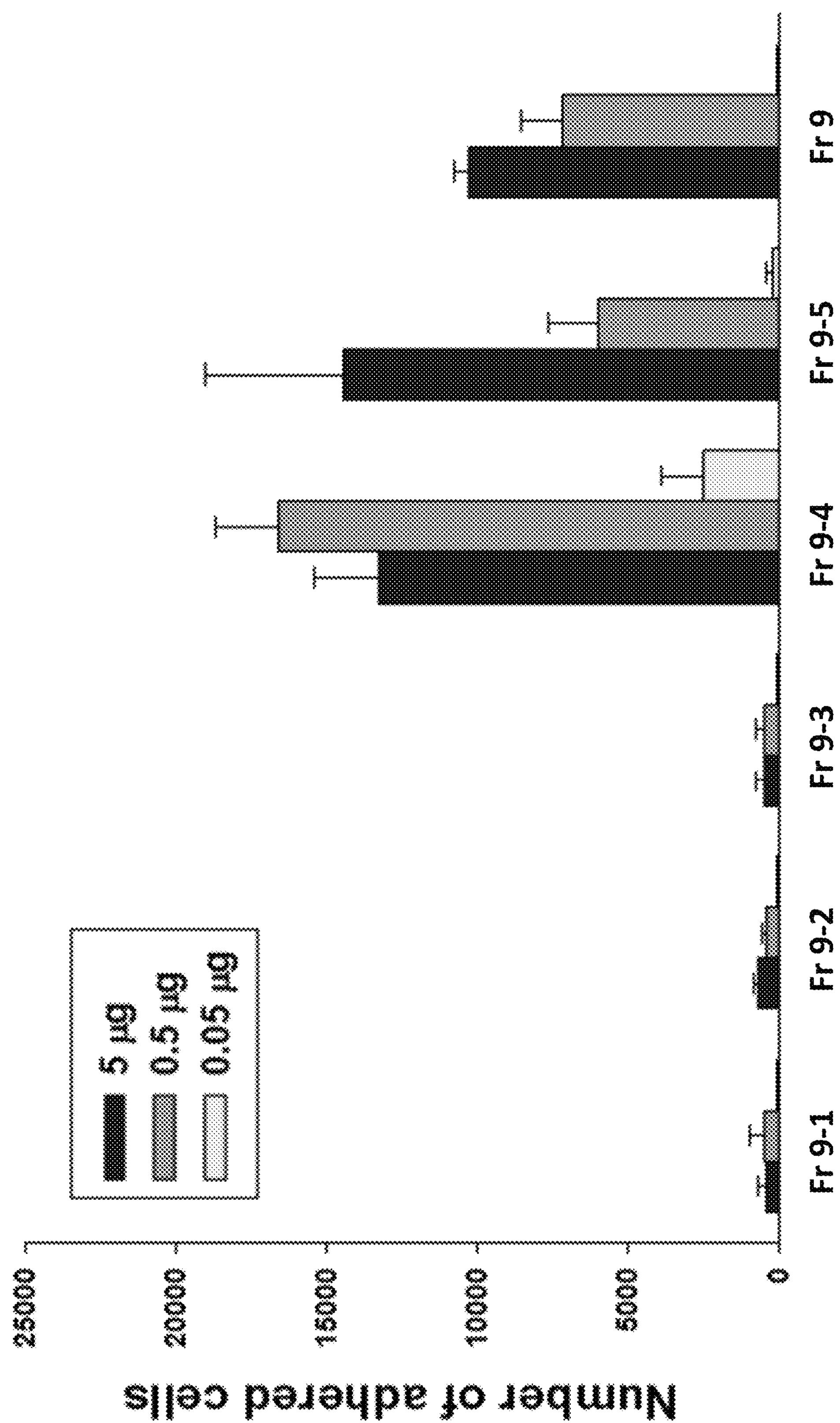

FIG. 14 depicts the results of experiments analyzing the activity of subfractions of Fraction 9 in a cell adhesion assay. Cell adhesion was performed using a a9LN18 cell line. Fractions were immobilized on a 96 well plate. Fr 9-4 and Fr 9-5 are further referred to as Bioactive Component Fraction 9-4 and Bioactive Component Fraction 9-5, or BCF9-4 and BCF9-5.

Figure 15:
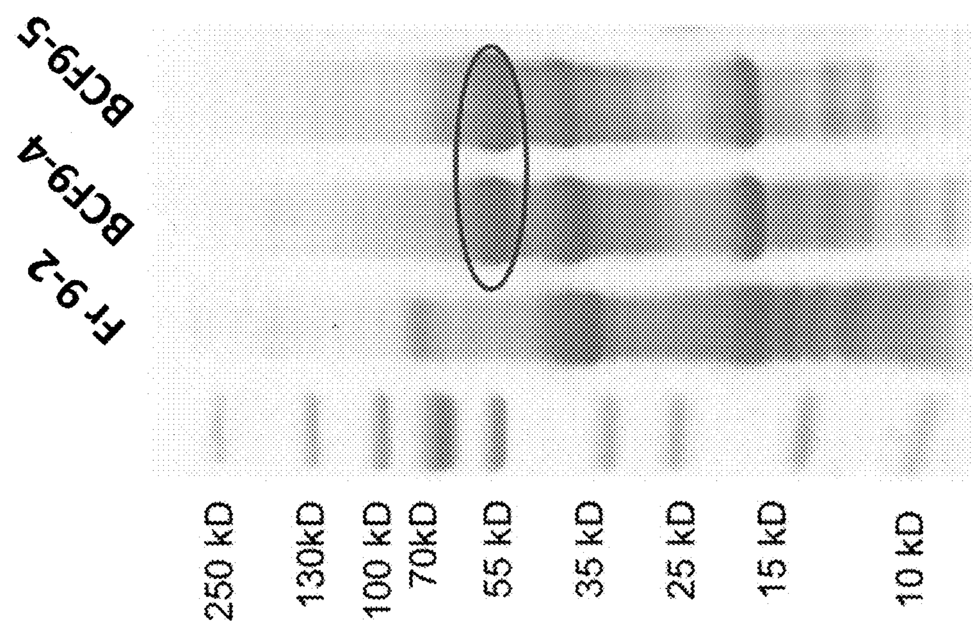

FIG. 15 depicts the results of a SDS-PAGE gel of Fraction 9 subfractions. BCF9-4 and BCF9-5 were biologically active while BCF5-2 was not. First line on the left represents molecular weight markers. Circles show bands that were analyzed for proteomics. Results are in FIG. 17.

Figure 13:
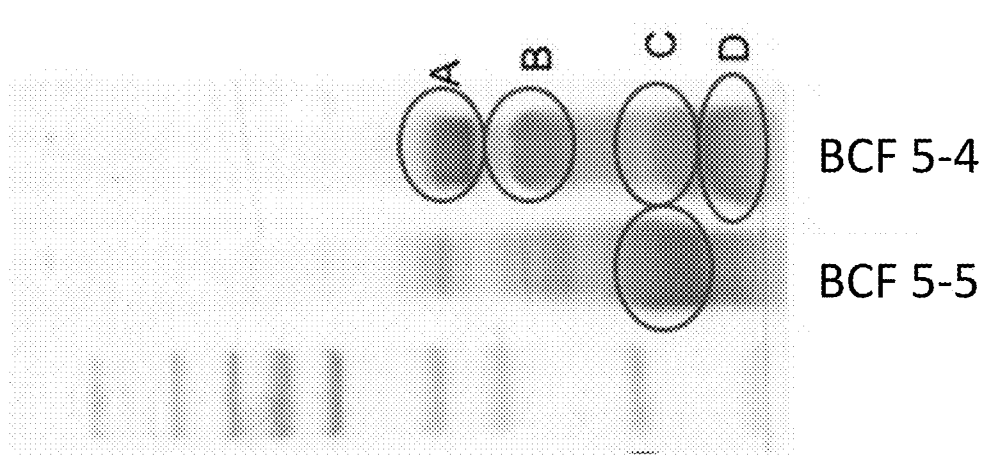
FIG. 13 depicts the results of a SDS-PAGE gel of Fraction 5 subfractions. Bioactive Component Fraction (BCF) 5-5 was biologically active while BCF5-4 was not. The first line on the left represents molecular weight markers. Circles show bands that were analyzed for proteomics. Results are in FIG. 16.

FIG. 16 is a table listing the peptide sequences of the BCF5-4 and BCF5-5 protein bands from the SDS-PAGE gel in FIG. 13. Mox is post-translationally modified methionine, oxidized amino acid (Methionine sulfoxide)

FIG. 17 is a table listing the peptide sequences of the BCF9-4 and BCF9-5 protein bands from the SDS-PAGE gel in FIG. 15. Mox is post-translationally modified methionine, oxidized amino acid (Methionine sulfoxide)

FIG. 18A through FIG. 18H depicts a series of histological stains of dermal treatments in a rat model of delayed wound closure. FIG. 18A and FIG. 18B depict intact dermal tissue. FIG. 18C and FIG. 18D depict untreated wounds. FIG. 18E and FIG. 18F depict wounds treated with a wet WSsoy composition after 14 days. FIG. 18G and FIG. 18H depict wounds treated with a dry WSsoy composition after 14 days. FIG. 18A, FIG. 18C, FIG. 18E, and FIG. 18G are Hematoxylin and Eosin (H&E) stains depicting the general histology of the samples. FIG. 18B, FIG. 18D, FIG. 18F, and FIG. 18H are picrosirius red stains indicating the presence of collagen in the samples. All images are magnified at 130×.

Figure 19:
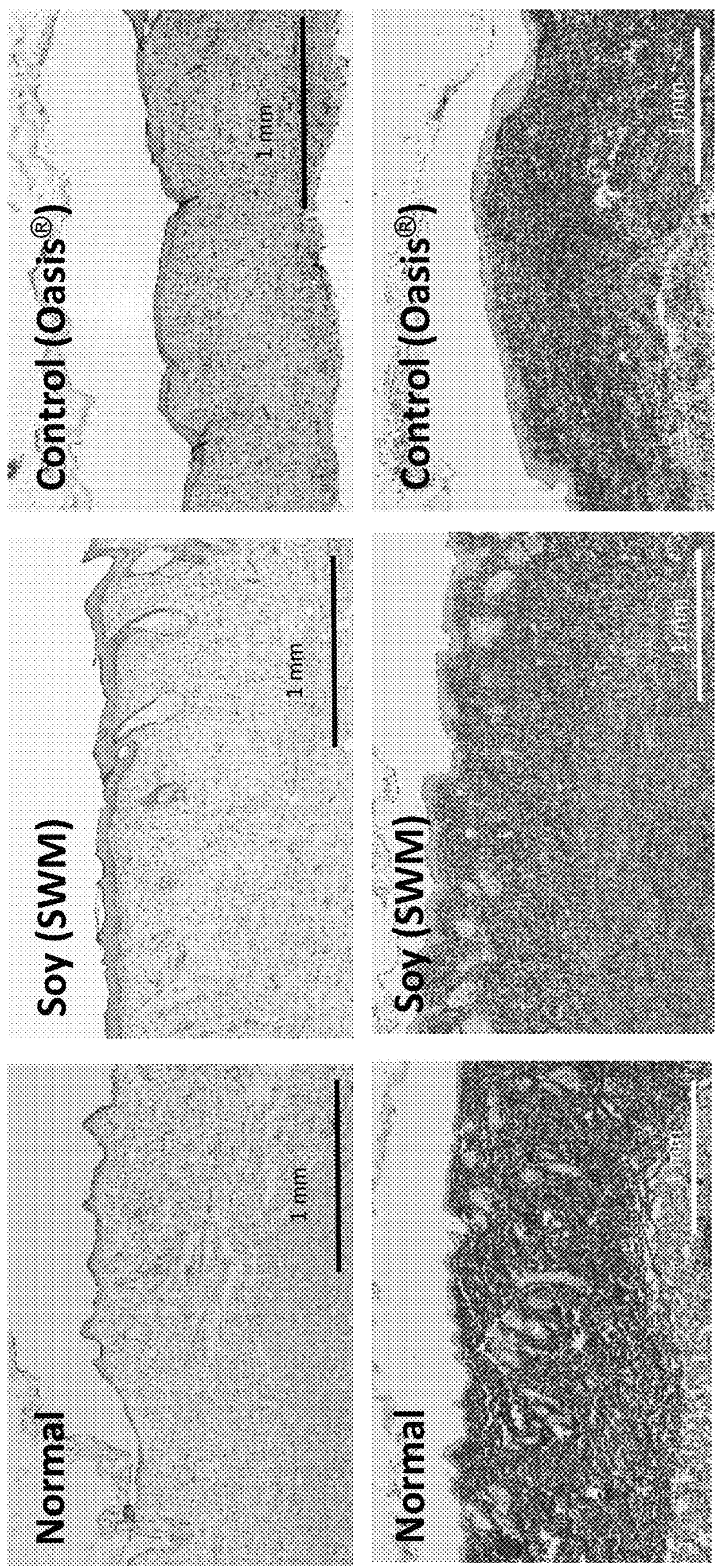

FIG. 19 is a series of histological stains of dermal treatments in a rat model. The left column depicts untreated, unwounded skin. The center column depicts wounds treated with a wet WSsoy composition after 14 days. The right column depicts wounds treated with a commercially available skin substitute, Oasis®. The top row is stained with H&E. The bottom row is stained with picrosirius red.

Figure 20:
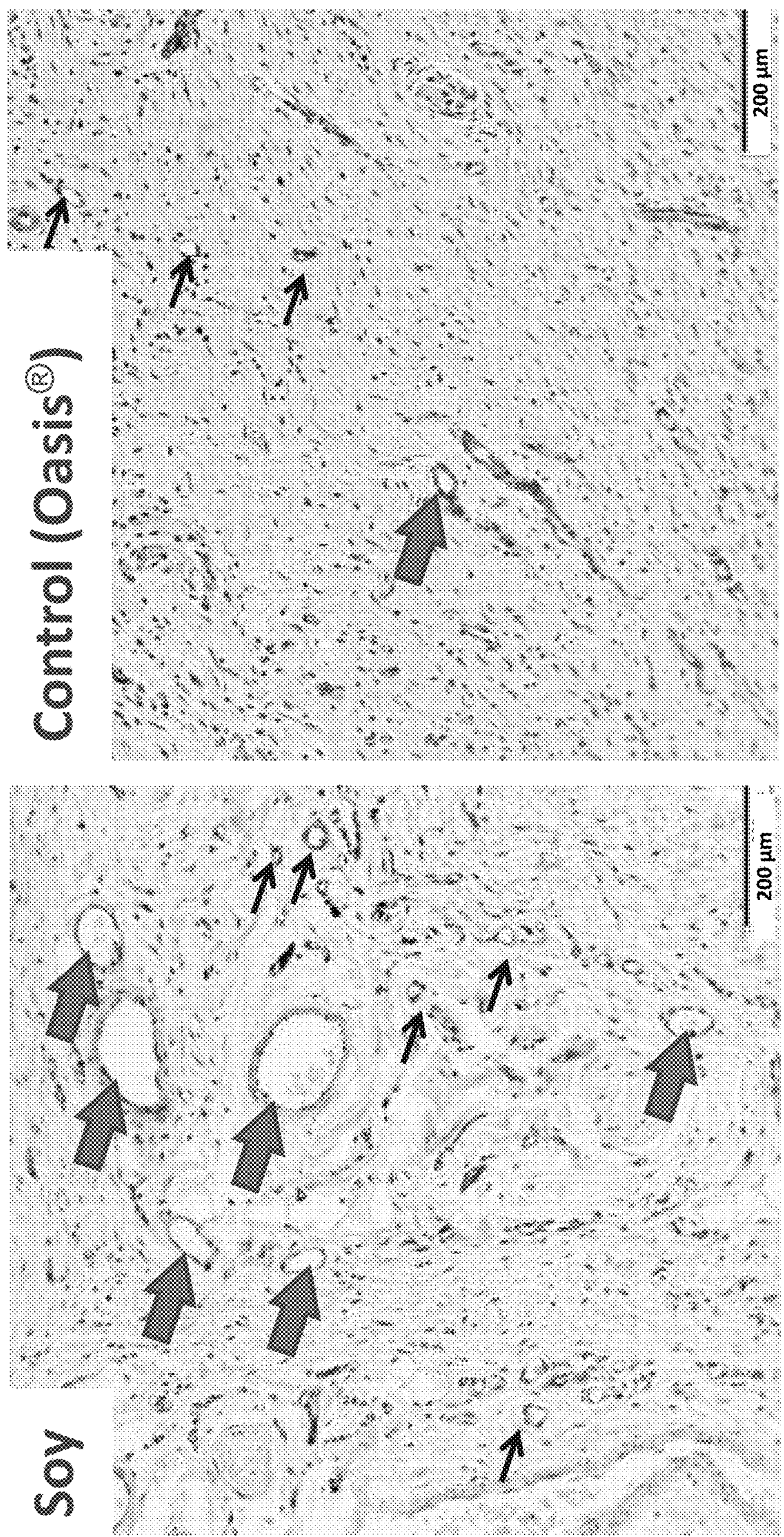

FIG. 20 depicts the results of experiments demonstrating vascularization of excisional full thickness cutaneous wounds in a rat model treated with soy protein isolate or Oasis® 21 days after treatment. Arrows point to new blood vessels which are more prevalent in Soy treated wounds than in the control wounds, which are mostly small vessels. (block arrows: large vessels; line arrows: small vessels).

Figure 21:
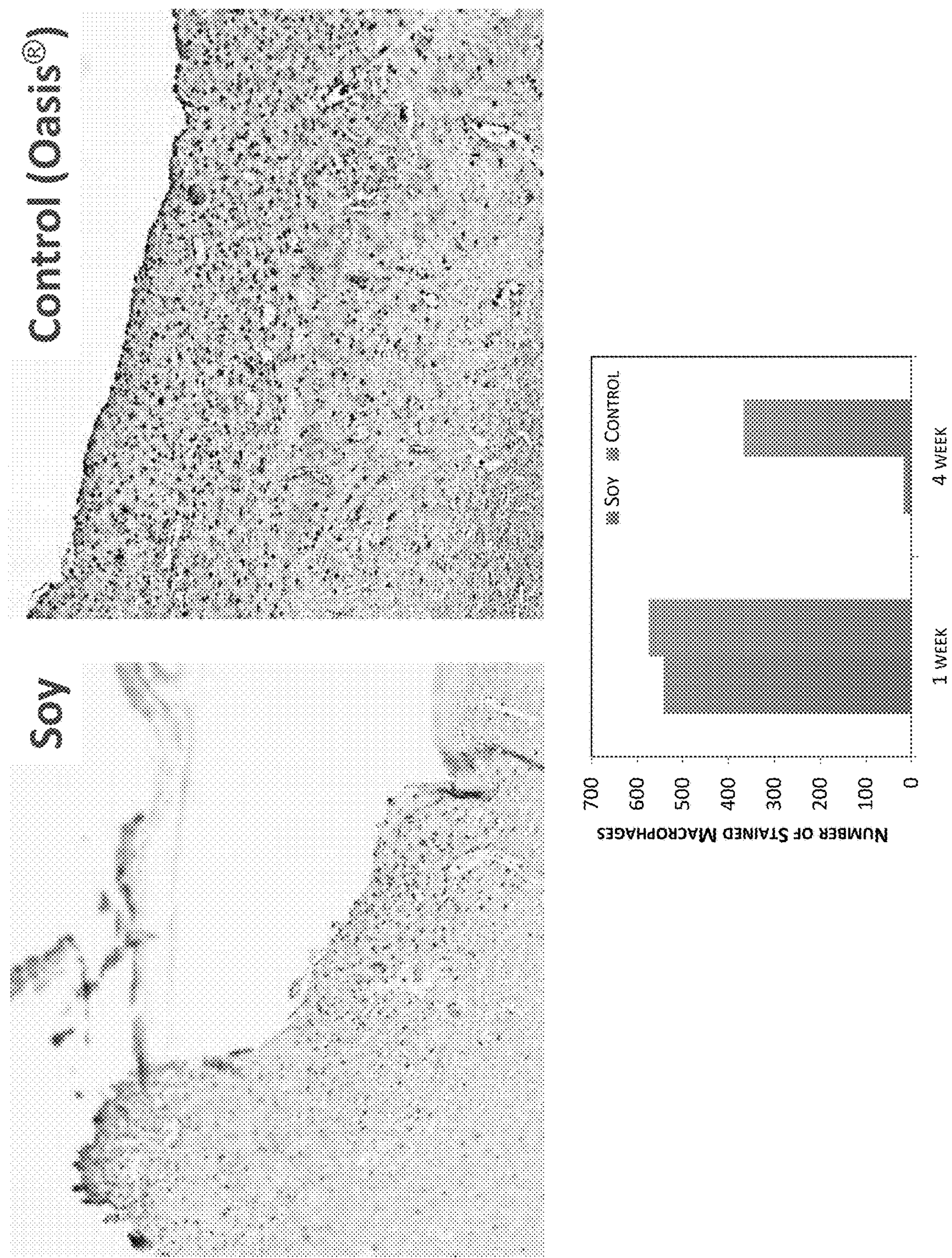

FIG. 21 depicts the results of experiments demonstrating macrophage invasion of excisional full thickness cutaneous wounds in a rat model treated with soy protein isolate or Oasis® 14 days after treatment. The bar graph depicts the amount of macrophages present in a porcine wound model treated with soy protein isolate vs untreated control after 1 week and 4 weeks.

Figure 22:
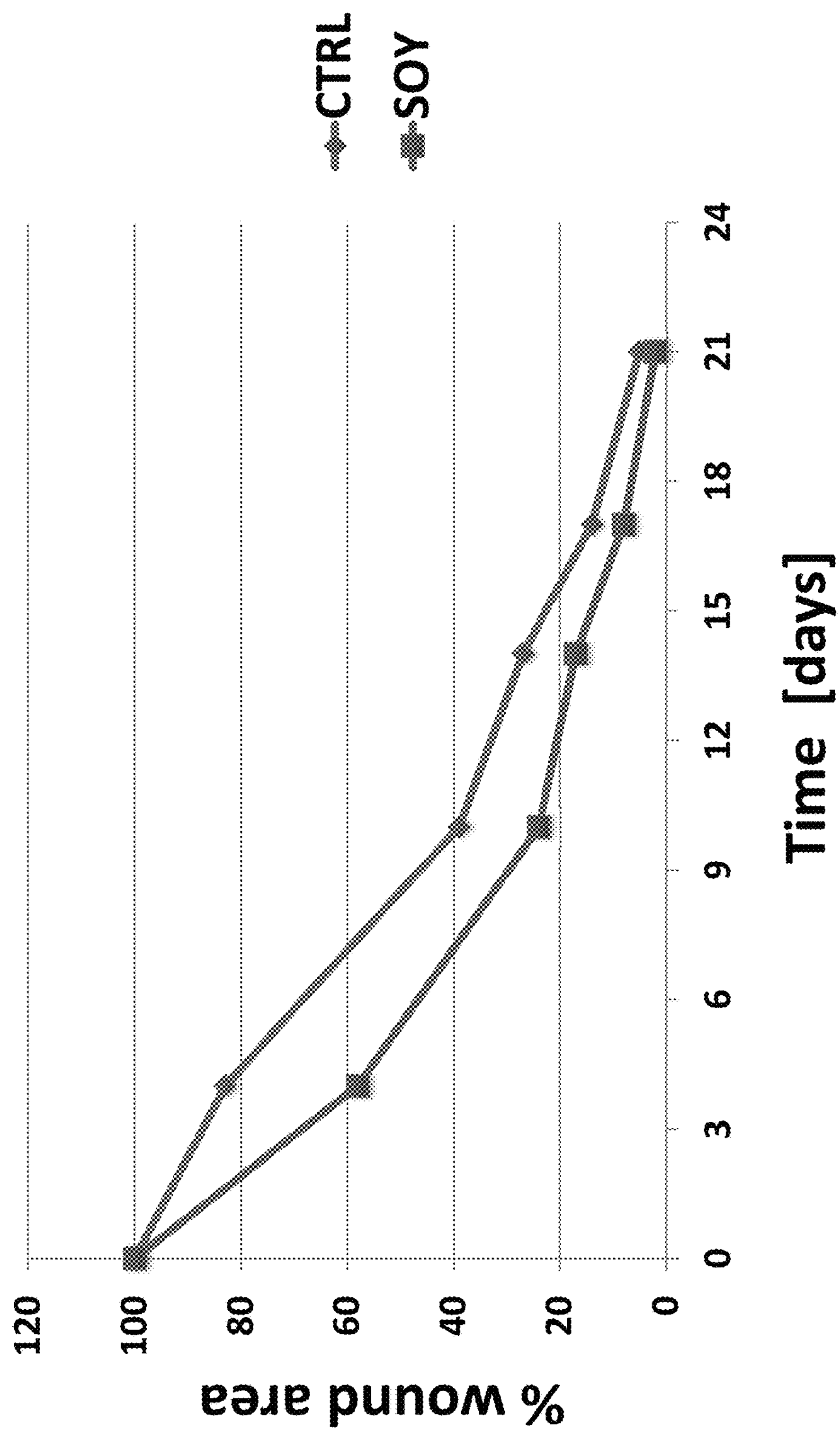

FIG. 22 depicts the results of experiments demonstrating that an exemplary electrospun soy composition accelerates wound closure in a porcine wound model treated with soy protein isolate vs. untreated control.

Figure 23:
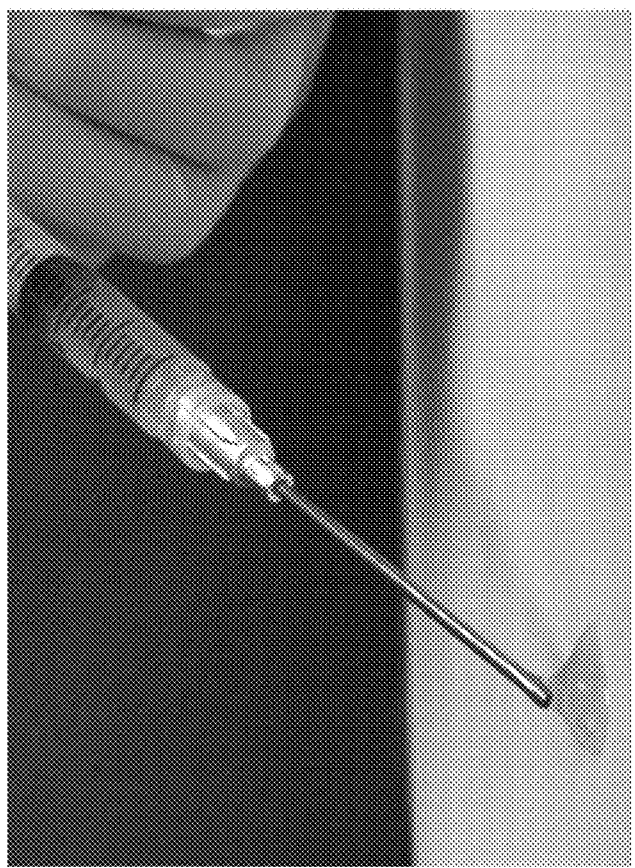

FIG. 23 depicts an exemplary WSsoy composition as a quasi-liquid matrix ready for dispensing in syringes (left panel), wherein the matrix can be dispensed through a needle and undergoes rapid polymerization (right panel).

Figures 24A, 24B, 24C, 24D:
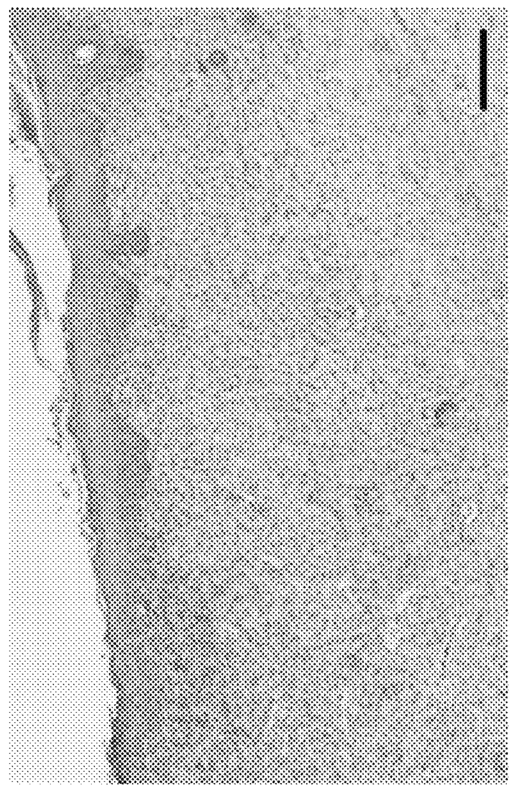

FIG. 24A through FIG. 24D depict the results of H&E staining of the epidermal layer of skin in full thickness excisional wounds treated with WSsoy formulations 14 days after wounding/treatment. FIG. 24A: WSsoy matrix applied as a gel; FIG. 24B: WSsoy matrix applied as a powder; FIG. 24C: WSsoy electroprocessed scaffold; and FIG. 24D: untreated control. The scale bars are each 200 microns.

Figure 25A:
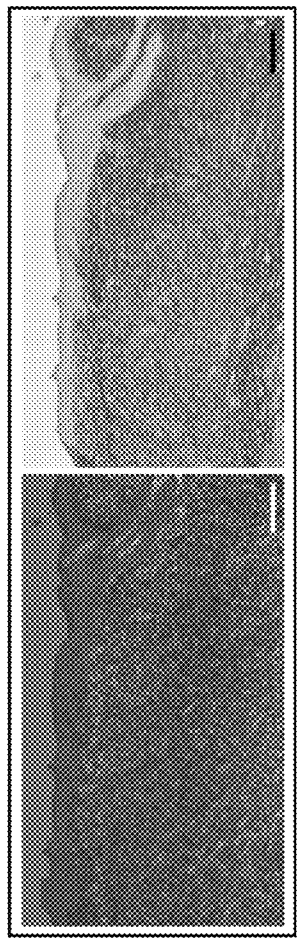
Figure 25B:
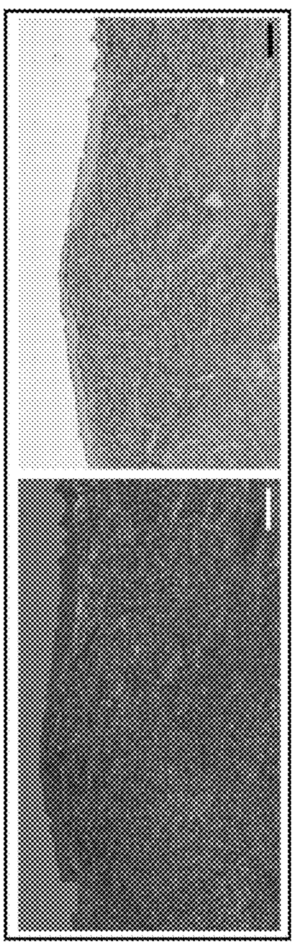
Figure 25C:
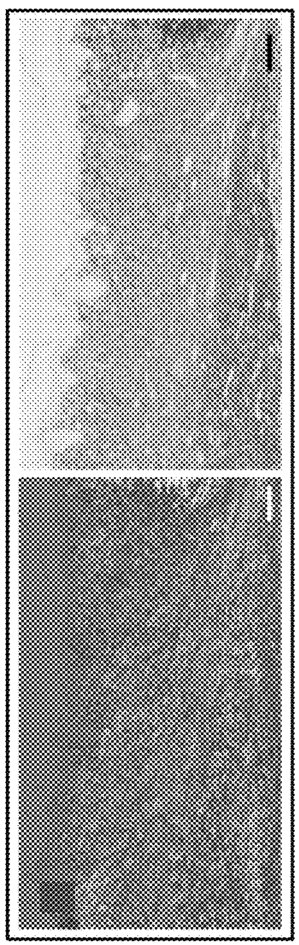
Figure 25D:
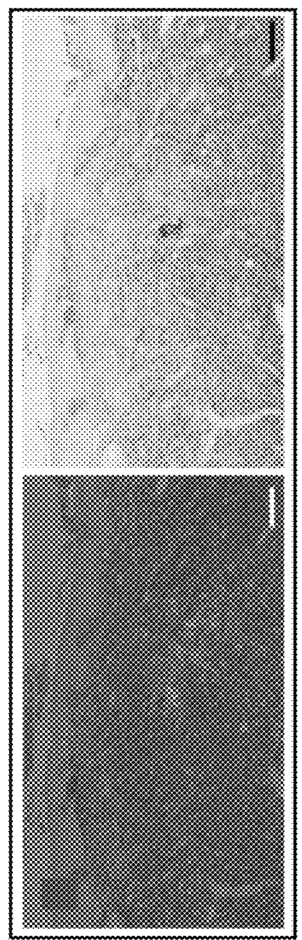

FIG. 25A through FIG. 25D depict the results of picrosirius red staining of the epidermal layer of skin in full thickness excisional wounds treated with WSsoy formulations 14 days after wounding/treatment. Each image pair contains a polarized light (left) and bright field (right) image. FIG. 25A: WSsoy matrix applied as a gel; FIG. 25B: WSsoy matrix applied as a powder; FIG. 25C: WSsoy electroprocessed scaffold; and FIG. 25D: untreated control. The scale bars are each 200 microns.

Figure 26:
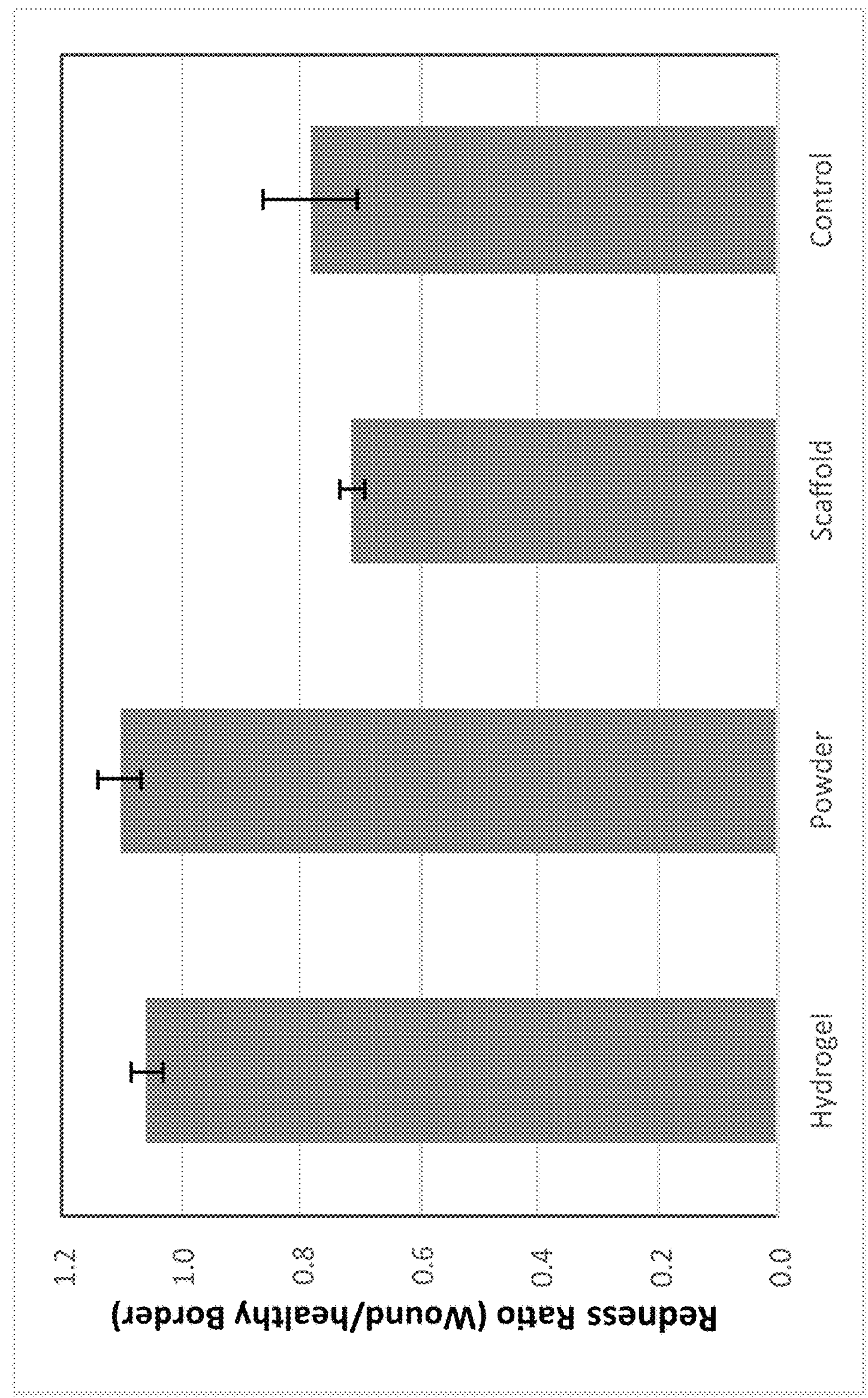

FIG. 26 depicts the quantification of collagen in picrosirius red stain (FIG. 25A through FIG. 25D) calculated as the "redness" of the wound relative to the healthy border area. 6 measurements were made in each area and the error bars represent the standard error of the mean. Calculations only represent the values from the images in FIG. 25A through FIG. 25D.

Figures 27A, 27B, 27C, 27D:
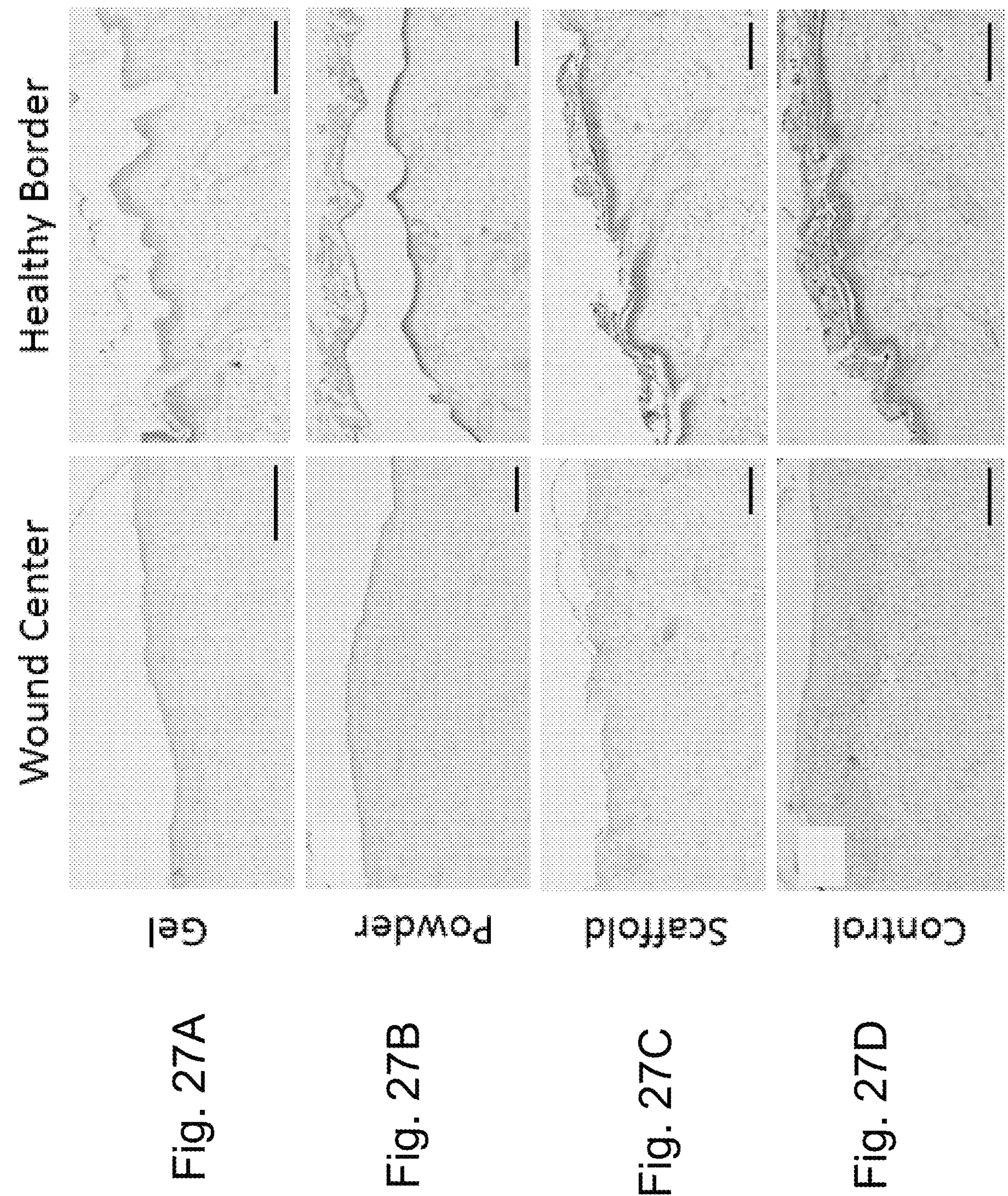

FIG. 27A through FIG. 27D depict the results of keratin staining of the epidermal layer of skin in full thickness excisional wounds treated with WSsoy formulations 14 days after wounding/treatment. More mature keratin stains darker. These samples indicate that gel and powder treated wounds have more mature keratin than the control. Each image pair contains an area in the center of the wound (left) and of healthy skin at the edges of the wound (right). FIG. 27A: WSsoy matrix applied as a gel; FIG. 27B: WSsoy matrix applied as a powder; FIG. 27C: WSsoy electroprocessed scaffold; and FIG. 27D: untreated control. The scale bars are each 200 microns.

Figure 28:
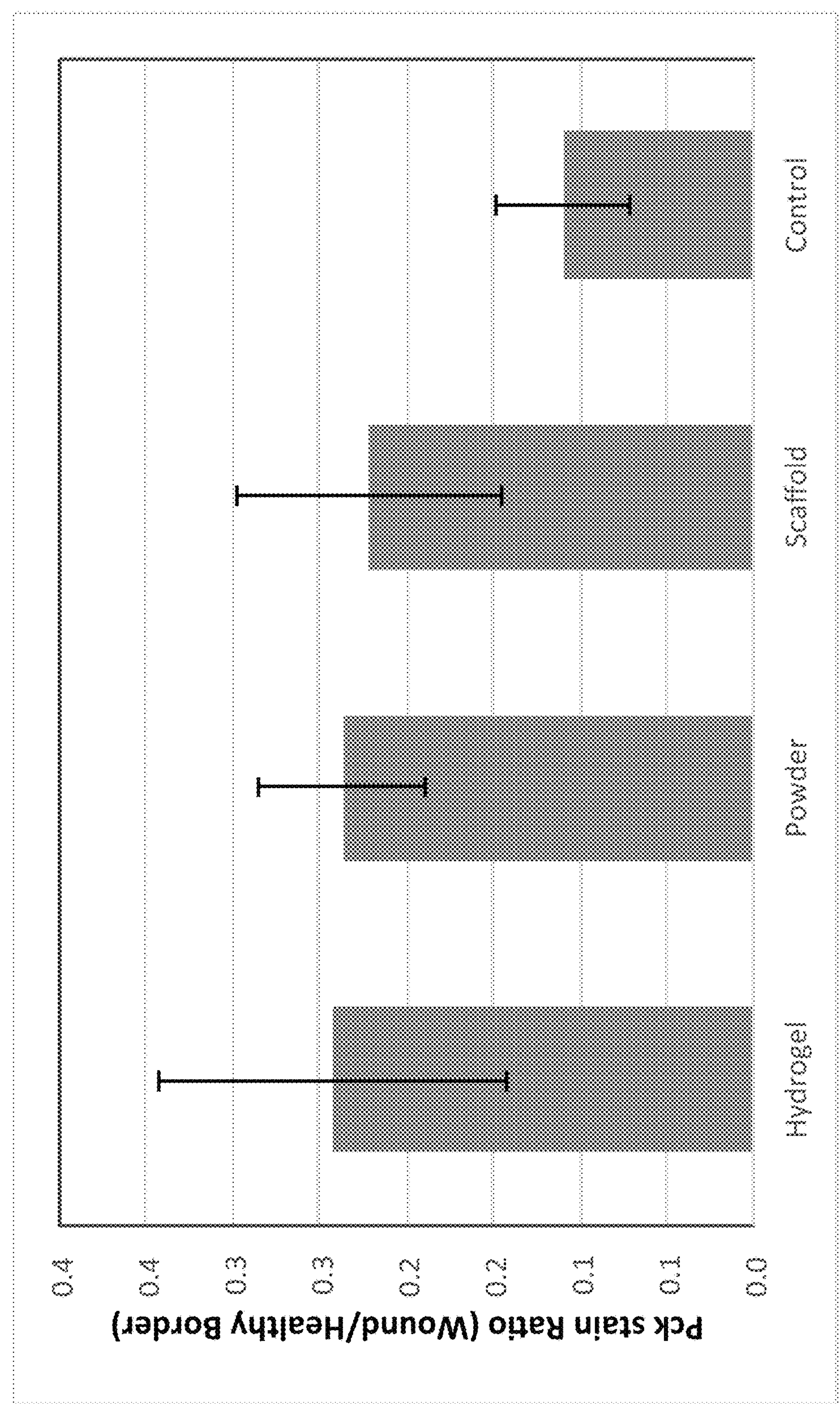

FIG. 28 depicts the quantification of the pan-cytokeratin (pck) antibody stain (FIG. 27A through FIG. 27D) in the wound relative to the healthy border area. 6 measurements were made in each area and the error bars represent the standard error of the mean. Calculations only represent the values from the images in FIG. 27A through FIG. 27D.

DETAILED DESCRIPTION

The present invention relates to compositions and methods using water-soluble soy protein isolates (referred to herein as "WSsoy") and/or bioactive peptide components of soy protein isolates (SPI). The invention is based, in part, upon the discovery that WSsoy has various advantageous over conventional soy protein isolates (SPI) for use in tissue engineering applications. For example, it is described herein that WSsoy is advantageous as it does not require the use of harsh organic solvents for processing of the soy protein. Further, WSsoy powder contained lower levels of isoflavonoids, which are a subset of estrogen analogs, which may pose challenges when using conventional SPI.

In certain embodiments, the compositions and methods comprise one or more bioactive peptide components of SPI. For example, it is described herein, that SPI comprises distinct protein/peptide fractions which confer bioactive activity. For example, various fractions of WSsoy are demonstrated to promote cell migration, cell proliferation, and angiogenesis.

The present invention provides tissue engineering and wound healing compositions comprising WSsoy and/or bioactive peptide components of SPI. Exemplary compositions include powders, solutions, hydrogels, films, lotions, sprays, drug delivery vehicles and scaffolds, alone or composite with other materials.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, amino acids, flavonoids, and combinations of these (e.g., glycoproteins, ribonucleoproteins, lipoproteins, or the like).

"Extracellular matrix" refers to one or more substances that provide substantially the same conditions for supporting cell growth as provided by an extracellular matrix synthesized by cells. The extracellular matrix may be provided on a substrate. Alternatively, the component(s) comprising the extracellular matrix may be provided in solution. Components of an extracellular matrix can include laminin, collagen and fibronectin.

The term "extracellular matrix component", as used herein, can include a member selected from laminin, collagen, fibronectin and elastin.

The term "blow spinning" refers to methods wherein materials are streamed, sprayed, sputtered or dripped toward a target substrate. The materials can be aerodynamically guided in the direction of a target substrate by one or more sources of pressurized gas streams.

The term "electrofocused" blow spinning refers to blow spinning methods wherein an electric field is provided solely to improve the focusing of a material stream towards a target substrate, rather than a necessary element to generate a stream of polymer such as in electrospinning. The term "electrofocused" is not limited to the specific examples set forth herein, and it includes any means of using an electrical field for depositing a material on a target.

The term "electroprocessing" or "electrodeposition" as used herein includes all methods of electrospinning, electrospraying, electroaerosoling, electroblowing, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. "Electrospinning" means a process in which fibers are formed from a solution or melt by streaming an electrically charged solution or melt through an orifice. "Electroaerosoling" means a process in which droplets are formed from a solution or melt by streaming an electrically charged polymer solution or melt through an orifice. "Electroblowing" means a process in which fibers are formed from a solution by blow spinning a polymer solution through an electric field. The term electroprocessing is not limited to the specific examples set forth herein, and it includes any means of using an electrical field for depositing a material on a target.

"Electroaerosoling" means a process in which droplets are formed from a solution or melt by streaming an electrically charged polymer solution or melt through an orifice.

"Growth factor" refers to a substance that is effective to promote the growth of cells. Growth factors include, but are not limited to, basic fibroblast growth factor (bFGF), acidic fibroblast growth factor (aFGF), epidermal growth factor (EGF), insulin-like growth factor-I (IGF-T), insulin-like growth factor-II (IGF-II), platelet-derived growth factor-AB (PDGF), vascular endothelial cell growth factor (VEGF), activin-A, bone morphogenic proteins (BMPs), insulin, cytokines, chemokines, morphogens, neutralizing antibodies, other proteins, and small molecules.

"Hydrogel" refers to a water-insoluble and water-swellable cross-linked polymer that is capable of absorbing at least 3 times, preferably at least 10 times, its own weight of a liquid. "Hydrogel" can also refer to a "thermo-responsive polymer" as used herein.

As used herein, "scaffold" refers to a structure, comprising a biocompatible material, that provides a biocompatible surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

The term "isolated" refers to a material that is substantially or essentially free from components, which are used to produce the material. The lower end of the range of purity for the compositions is about 60%, about 70% or about 80% and the upper end of the range of purity is about 70%, about 80%, about 90% or more than about 90%.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the terms "tissue grafting" and "tissue reconstructing" both refer to implanting a graft into an individual to treat or alleviate a tissue defect, such as a lung defect or a soft tissue defect.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

"Sample" or "biological sample" as used herein means a biological material from a subject, including but is not limited to organ, tissue, exosome, blood, plasma, saliva, urine and other body fluid. A sample can be any source of material obtained from a subject.

As used herein, to "alleviate" a disease, defect, disorder or condition means reducing the severity of one or more symptoms of the disease, defect, disorder or condition.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

As used herein, the term "growth medium" is meant to refer to a culture medium that promotes growth of cells. A growth medium will generally contain animal serum. In some instances, the growth medium may not contain animal serum.

"Differentiation medium" is used herein to refer to a cell growth medium comprising an additive or a lack of an additive such that a stem cell, fetal pulmonary cell or other such progenitor cell, that is not fully differentiated, develops into a cell with some or all of the characteristics of a differentiated cell when incubated in the medium.

An "isolated cell" refers to a cell which has been separated from other components and/or cells which naturally accompany the isolated cell in a tissue or mammal.

As used herein, a "substantially purified" cell is a cell that is essentially free of other cell types. Thus, a substantially purified cell refers to a cell which has been purified from other cell types with which it is normally associated in its naturally-occurring state.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein "endogenous" refers to any material from or produced inside an organism, cell or system.

"Exogenous" refers to any material introduced into or produced outside an organism, cell, or system.

As used herein, "wound healing" is intended to include all disorders characterized by any disease, disorder, syndrome, anomaly, pathology, or abnormal condition of the skin and/or underlying connective tissue, e.g., skin wounds caused by mechanical injury, skin wounds following surgery, skin abrasions caused by mechanical trauma, caustic agents or burns, cornea following cataract surgery or corneal transplants, mucosal epithelium wounds following infection or drug therapy (e.g., respiratory, gastrointestinal, genitourinary, mammary, oral cavity, ocular tissue, liver and kidney), diabetic wounds, skin wounds following grafting, and regrowth of blood vessels following angioplasty.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods using soybean-derived proteins for tissue engineering and wound healing purposes. In one aspect, the invention includes a scaffold, including for example a hydrogel, an electrospun scaffold, and the like, where the scaffold comprises soy-protein isolates and/or bioactive components thereof. In one aspect, the invention includes a topical composition, including a powder, ointment, gel, paste, and the like, where the composition comprises soy-protein isolates and/or bioactive components thereof. The invention provides a means of generating biomaterials comprising soy-derived protein isolates and/or bioactive components thereof. Such biomaterials can be used as a scaffold in tissue engineering, drug delivery, drug discovery, therapy, and other research purposes.

In certain embodiments, the soy-protein isolates of the present invention comprise water-soluble soy protein isolates (WSsoy) and/or bioactive components thereof. As described herein WSsoy has particular safety, economic, and practical advantages over conventional soy protein isolates.

The study of wound-healing properties of plant derived bioactive compounds (nutraceuticals) in general, and of soy/plants in particular, is in its infancy. Previous studies, focusing on conventional soy protein isolates (SPI), have demonstrated that many of the beneficial effects of SPI may be traced to the phytoestrogens/isoflavonoids contained in SPI. Being estrogen analogs, the use of phytoestrogens, such as genistein, poses its own challenges.

Described herein are compositions and methods using water-soluble formulation of soy protein isolate (WSsoy) for wound healing. WSsoy is an inexpensive, renewable, 'green' raw material, devoid of isoflavonoids. The development of WSsoy-derived bioactive/regenerative therapeutic modalities will change the paradigm of soy-based technologies for wound healing, as the material no longer contains phytoestrogens. The recent availability of water-soluble soy protein isolates, which are devoid of isoflavonoids/phytoestrogens, offers the opportunity to investigate the therapeutic contribution of this complex protein mixture and/or its components in models of wound healing.

It is described herein that WSsoy possesses regenerative bioactivity that resides in distinct soy proteins and/or their degradation products. Further, it is demonstrated herein that bioactive proteinaceous WSsoy components can influence complex cutaneous wound healing behavior of skin cells by different cellular signaling pathways. Experiments presented herein demonstrate the separation of the bioactive proteinaceous components in WSsoy, which has revealed some of the distinct mechanisms of action by which individual WSsoy protein fractions exert their activities responsible for wound healing.

In one embodiment, the invention relates to the use of a peptide fraction, referred to herein as Fraction 5, which strongly stimulates the migration of skin cells. As used herein, Fraction 5 may refer to a bioactive peptide fraction or to a bioactive peptide component of SPI. While it is described herein that Fraction 5 is derived from WSsoy, it is contemplated herein that Fraction 5 may be derived from any SPI formulation. In the experiments described herein, a Bioactive Component Fraction (BCF) of Fraction 5 may be referred to as BCF5-5.

In certain instances Fraction 5 comprises a peptide fraction that can be eluted using reverse phase-high pressure liquid chromatography (RP-HPLC) separation of WSsoy with a C18 column, using a linear gradient of elution (0-80% acetonitrile (ACN) over 45 minutes. This protein fraction elutes with a retention time of about 25-35 minutes as identified by uv detection at 230 nm. Additional analysis shows the zeta potential of this protein fraction to be 17.9+/−1.2 mV.

In one embodiment, the invention relates to the use of a peptide fraction, referred to herein as Fraction 9, which strongly selectively binds to an integrin involved in wound healing. As used herein, Fraction 9 may refer to a bioactive peptide fraction or to a bioactive peptide component of SPI. While it is described herein that Fraction 9 is derived from WSsoy, it is contemplated herein that Fraction 9 may be derived from any SPI formulation. In the experiments described herein, a Bioactive Component Fraction of Fraction 9 may be referred to as BCF9-4.

In certain instances, Fraction 9 comprises a peptide fraction that can be eluted using reverse phase-high pressure liquid chromatography (RP-HPLC) separation of WSsoy with a C18 column, using a linear gradient of elution (0-80% acetonitrile (ACN) over 45 minutes. This protein fraction elutes with a retention time of about 35-40 minutes as identified by uv detection at 230 nm. Additional analysis shows the zeta potential of this protein fraction to be 34.2+/−0.7 mV. In certain embodiments, Fraction 9 comprises the alpha prime chain of beta-conglycinin ((3CG) or fragments thereof.

In certain instances, the bioactive peptide fractions may be further purified to yield smaller protein fractions, or subfractions. The subfractions may comprise peptides having the highest bioactivity, such as β-conglycinin. B-conglycinin comprises the LDV motif, which is critical for integrin binding and permits the binding of plant protein to mammalian tissue. In some embodiments, the invention relates to peptides or fragments thereof comprising the LDV motif. In one embodiment, the invention relates to the use of the bioactive peptide subfractions.

As such, the invention should also be construed to include any peptide having substantial homology the peptides disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of a peptide disclosed herein.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

Thus, WSsoy and bioactive peptide components of SPI can be developed into novel therapeutic modalities/drugs for wound healing drugs by different formulations such as powders, solutions, films, sprays, lotions, ointments, hydrogel and fibrous wound matrices alone or in combination with other drugs (antibiotics, anti-inflammatories, analgesics, etc.).

Composition

The invention is based on the discovery that WSsoy and bioactive peptide components of SPI can be used to promote wound healing. Thus, the present invention provides a composition for wound healing and tissue engineering applications comprising WSsoy, Fraction 5, Fraction 9, and/or bioactive peptide components of SPI. In various embodiments, the composition comprises a powder, solution, gel, paste, lotion, hydrogel, nicrosphere, or electrospun scaffold, wherein the composition comprises WSsoy, Fraction 5, Fraction 9, and/or bioactive peptide components of SPI.

As used herein, the term "soy material" is defined as a material derived from soybeans. The term "soybean" refers to the species *Glycine max, Glycine soja*, or any species that is sexually cross compatible with *Glycine max.*

The term "soy protein isolate" as used herein is used in the sense conventional to the soy protein industry. For example, a soy protein isolate is a soy material having a protein content of at least 90% soy protein on a moisture free basis. "Isolated soy protein", as used in the art, has the same meaning as "soy protein isolate" as used herein and as used in the art. A soy protein isolate is formed from soybeans by removing the hull and germ of the soybean from the cotyledon, flaking or grinding the cotyledon and removing oil from the flaked or ground cotyledon, separating the soy protein and carbohydrates of the cotyledon from the cotyledon fiber and lipids, and subsequently separating the soy protein from the carbohydrates. In certain embodiments, the resultant material is washed with ethanol to remove a percentage of isoflavonoids.

In one embodiment, the soy-based composition comprises a fibrous material containing soy protein and soy cotyledon fiber. The fibrous material generally comprises a defatted soy protein material and soy cotyledon fiber. The fibrous material is produced by extruding the soy protein material and soy cotyledon fiber. The fibrous material has a moisture content of from 6% to 80%. Moisture conditions employed in producing the fibrous material are low moisture fibrous material (6% to 35%) and high moisture fibrous material (50% to 80%). Additional ingredients may be extruded with the soy protein material and the soy cotyledon fiber such as wheat gluten, starch, and Kunitz protein inhibitor.

The soy protein isolate should not be a highly hydrolyzed soy protein isolate having a low molecular weight distribution since highly hydrolyzed soy protein isolates lack the protein chain length to properly form protein fibers in the process. Highly hydrolyzed soy protein isolates, however, may be used in combination with other soy protein isolates provided that the highly hydrolyzed soy protein isolate content of the combined soy protein isolates is less than 40% of the combined soy protein isolates, by weight.

The soy protein isolate utilized should have a water holding capacity sufficient to enable the protein in the isolate to form fibers upon electroprocessing. The water holding capacity of the soy protein isolate is a measure of the amount of swelling the protein undergoes when hydrated. The swelling of the protein should be sufficient to enable the protein to form intermolecular contacts to permit fiber formation to occur. The soy protein isolate used in the process of the invention preferably has a water holding capacity of at least 4.0 grams of water per gram of soy protein isolate (as is) at pH 7.0, and more preferably has a water holding capacity of at least 5.0 grams of water per gram of soy protein isolate (as is) at pH 7.0. The water holding capacity is determined by using the centrifuge method.

Non-highly hydrolyzed soy protein isolates having a water holding capacity of at least 4.0 grams of water per gram of soy protein isolate that are useful in the present invention are commercially available.

Soy protein isolates useful in the fibrous material may be produced from soybeans according to conventional processes in the soy protein manufacturing industry. Exemplary of such a process, whole soybeans are initially detrashed, cracked, dehulled, degermed, and defatted according to conventional processes to form soy flakes, soy flour, soy grits, or soy meal. The soybeans may be detrashed by passing the soybeans through a magnetic separator to remove iron, steel, and other magnetically susceptible objects, followed by shaking the soybeans on progressively smaller meshed screens to remove soil residues, pods, stems, weed seeds, undersized beans, and other trash. The detrashed soybeans may be cracked by passing the soybeans through cracking rolls. Cracking rolls are spiral-cut corrugated cylinders which loosen the hull as the soybeans pass through the rolls and crack the soybean material into several pieces. The cracked soybeans may then be dehulled by aspiration. The dehulled soybeans are degermed by shaking the dehulled soybeans on a screen of sufficiently small mesh size to remove the small sized germ and retain the larger cotyledons of the beans. The cotyledons are then flaked by passing the cotyledons through a flaking roll. The flaked cotyledons are defatted by extracting oil from the flakes by mechanically expelling the oil from the flakes or by contacting the flakes with hexane or other suitable lipophilic/hydrophobic solvent. The defatted flakes may be ground to form a soy flour, a soy grit, or a soy meal, if desired.

The defatted soy flakes, soy flour, soy grits, or soy meal is/are then extracted with an aqueous alkaline solution, typically a dilute aqueous sodium hydroxide solution having a pH of from 7.5 to 11.0, to extract protein soluble in an aqueous alkaline solution from insolubles. The insolubles are soy cotyledon fiber which is composed primarily of insoluble carbohydrates. An aqueous alkaline extract containing the soluble protein is subsequently separated from the insolubles, and the extract is then treated with an acid to lower the pH of the extract to around the isoelectric point of the soy protein, preferably to a pH of from 4.0 to 5.0, and most preferably to a pH of from 4.4 to 4.6. The soy protein precipitates from the acidified extract due to the protein's lack of solubility in an aqueous solution at or near its isoelectric point. The precipitated protein curd is then separated from the remaining extract. The separated protein may be washed with water to remove residual soluble carbohydrates and ash from the protein material. The separated protein is then dried using conventional drying means such as spray drying or tunnel drying to form a soy protein isolate.

In certain embodiments, the soy protein isolate may be washed with ethanol, methanol, isopropyl alcohol, and the like, which removes isoflavonoids, such as genistein, but does not remove of the bioactive fractions Prokinet and Fraction 9

Soy protein concentrate may be blended with the soy protein isolate to substitute for a portion of the soy protein isolate as a source of soy protein. Soy protein isolates, in general, have higher water holding capacity and form better fibers than soy protein concentrates. Therefore, the amount of soy protein concentrate substituted for soy protein isolate should be limited to an amount that will permit significant fiber formation in the extrudate. Preferably, if a soy protein concentrate is substituted for a portion of the soy protein isolate, the soy protein concentrate is substituted for up to 40% of the soy protein isolate by weight, at most, and more preferably is substituted for up to 30% of the soy protein isolate by weight.

Soy protein concentrates useful in the fibrous material are commercially available. Soy protein concentrates useful in the present invention may also be produced from soybeans according to conventional processes in the soy protein manufacturing industry. For example, defatted soy flakes, soy flour, soy grits, or soy meal produced as described above may be washed with aqueous ethanol (preferably 60% to 80% aqueous ethanol) to remove soluble carbohydrates from the soy protein and soy fiber. The soy protein and soy fiber containing material is subsequently dried to produce the soy protein concentrate. Alternatively, the defatted soy flakes, soy flour, soy grits, or soy meal may be washed with an aqueous acidic wash having a pH of from 4.3 to 4.8 to remove soluble carbohydrates from the soy protein and soy fiber. The soy protein and soy fiber containing material is subsequently dried to produce the soy protein concentrate.

The soy cotyledon fiber utilized in the fibrous material should effectively bind water when the mixture of soy protein material and soy cotyledon fiber are co-extruded. By binding water, the soy cotyledon fiber induces a viscosity gradient across the extrudate as the extrudate is extruded through a cooling die, thereby promoting the formation of protein fibers. To effectively bind water for the purposes of the process of the present invention, the soy cotyledon fiber should have a water holding capacity of at least 5.50 grams of water per gram of soy cotyledon fiber, and preferably the soy cotyledon fiber has a water holding capacity of at least 6.0 grams of water per gram of soy cotyledon fiber. It is also preferable that the soy cotyledon fiber has a water holding capacity of at most 8.0 grams of water per gram of soy cotyledon fiber.

The soy cotyledon fiber is a complex carbohydrate and is commercially available. Soy cotyledon fiber useful in the process of the present invention may also be produced according to conventional processes in the soy processing industry. For example, defatted soy flakes, soy flour, soy grits, or soy meal produced as described above may be extracted with an aqueous alkaline solution as described above with respect to the production of a soy protein isolate to separate the insoluble soy cotyledon fiber from the aqueous alkaline soluble soy protein and carbohydrates. The separated soy cotyledon fiber is then dried, preferably by spray drying, to produce a soy cotyledon fiber product. Soy cotyledon fiber is generally present in the fibrous material at from 1% to 8%, preferably at from 1.5% to 7.5% and most preferably at from 2% to 5% by weight on a moisture free basis.

As described herein, the present invention comprises water-soluble soy protein isolate (WSsoy), and components or fractions thereof. In certain embodiments the water-soluble SPI solution is separated from any insoluble that may be present. As described elsewhere herein, in certain instances WSsoy is characterized by a reduced level of isoflavonoids/phytoestrogens that are present in conventional soy protein isolates.

Figure 2:
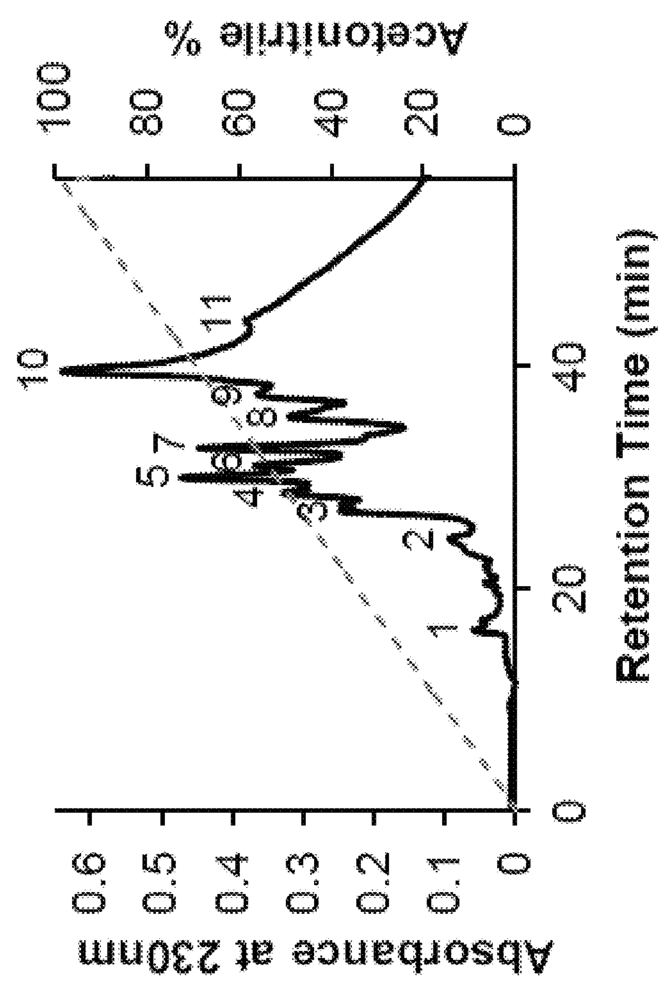
FIG. 2 is a graph depicting the RP-HPLC separation of WSsoy. WSsoy was solubilized in TFA and injected into a Cis VYDAC column and separated with a linear gradient of ACN (dotted line). Numbers indicate fractions that were collected and characterized by biological assays.

In certain embodiments, WSsoy is fractionated into bioactive components. For example, WSsoy may be fractionated using methods known in the art including, but not limited to, 1D- or 2D-electrophoresis, liquid chromatography, fast liquid chromatography, high pressure liquid chromatography, cation exchange chromatography, anion exchange chromatography, reversed phase chromatography, biphasic ion-exchange chromatography, chromatofocusing, and size exclusion chromatography. As described elsewhere herein, in certain embodiments, WSsoy is fractionated using reverse phase-high pressure liquid chromatography (RP-HPLC). For example, in WSsoy can be separated using C18 with a linear gradient of elution (0-80% acetonitrile (ACN), which results in 11 protein fractions (FIG. 2). For example, RP-HPLC fractionation results in at least two protein fractions (denoted as Fraction 5 and Fraction 9) which display significant wound healing properties. In certain embodiments, bioactive fractions can be further fractionated by re-chromatographing the fraction. For example, Fraction 5 can be further fractioned by re-chromatographing on a RP-HPLC Cis column, using a "flatter" gradient of ACN (30-80% over 120 min.). Further, Fraction 9 can be further fractioned by re-chromatographing on RP-HPLC using a "flatter" gradient of acetonitrile (40-80% over 120 min.). In certain embodiments, the bioactive fractions may be purified for inclusion into the wound-healing compositions described herein.

In certain embodiments, the composition comprises a powder comprising WSsoy, Fraction 5, Fraction 9, and/or bioactive peptide components of SPI. For example, in certain embodiments, WSsoy, Fraction 5, Fraction 9, and/or bioactive peptide components of SPI may be lyophilized, or freeze-dried, using any method known in the art, see, e.g., U.S. Pat. No. 4,001,944. For example, WSsoy, Fraction 5, Fraction 9, and/or bioactive peptide components of SPI may be quickly frozen in 100% ethanol and dry ice, then lyophilized at −20° C. in a sterile lyophilizer until dry.

In certain embodiments, WSsoy, Fraction 5, Fraction 9, and/or bioactive peptide components of SPI are milled, minced, or grounded into a fine powder. Formation of the derived powder may be carried out by any method known in the art. For example, in one embodiment, WSsoy, Fraction 5, Fraction 9, and/or bioactive peptide components of SPI are placed within a cryogenic impact grinder. An exemplary cryogenic impact grinder is the Spex SamplePrep 6870 Freezer/Mill®, which allows for cycling of cooling phases and milling phases during the grinding of samples.

In one embodiment, the compositions of the invention comprise a solution comprising WSsoy, Fraction 5, Fraction 9, and/or bioactive peptide components of SPI. For example, in certain embodiments, WSsoy, Fraction 5, Fraction 9, and/or bioactive peptide components of SPI are mixed with a suitable buffer to arrive at a solution. In certain embodiments, the pH of the solution is adjusted. For example, the solution may be adjusted to a pH in the range of about 7-7.5.

In some embodiments, WSsoy, Fraction 5, Fraction 9, and/or bioactive peptide components of SPI may be mixed with a suitable isotonic buffer or cell culture medium. Suitable buffers include, but are not limited to, phosphate buffered saline (PBS), saline, MOPS, HEPES, Hank's Balanced Salt Solution, and the like. A suitable cell culture medium includes, but is not limited to, RPMI 1640, Fisher's, Iscove's, McCoy's, Dulbecco's medium, and the like.

In certain embodiments, the composition comprises a cream, liquid, gel, spray, ointment, or the like which comprises WSsoy, Fraction 5, Fraction 9, and/or bioactive peptide components of SPI. For example, in certain embodiments, the composition comprises a cream, liquid, gel, spray, ointment, or the like comprising powderized or soluble WSsoy, Fraction 5, Fraction 9, and/or bioactive peptide components of SPI.

In one embodiment, the composition comprises a drug delivery vehicle comprising WSsoy, Fraction 5, Fraction 9, and/or bioactive peptide components of SPI. For example, the drug delivery vehicle may be embedded with WSsoy, Fraction 5, Fraction 9, and/or bioactive peptide components of SPI. In certain embodiments, the vehicle is formulated for controlled, continual, or delayed release of WSsoy, Fraction 5, Fraction 9, and/or bioactive peptide components of SPI from the vehicle. Exemplary drug delivery vehicles include, but are not limited to microspheres, microparticles, nanoparticles, polymerosomes, lipid nanoparticles, micelles, and the like.

In certain embodiments, the drug delivery vehicle comprises microspheres comprising one or more biopolymers or synthetic polymers. For example, in one embodiment, the microspheres comprise PLGA. In one embodiment, the microspheres comprise alginate. However, the present invention is not limited to any particular formulation of polymeric microspheres. Rather the present invention encompasses any suitable microsphere known in the art capable of being loaded or embedded with WSsoy, Fraction 5, Fraction 9, and/or bioactive peptide components of SPI, either in solution or embedded within nanoparticles.

Pharmaceutical Compositions

The present invention also provides pharmaceutical compositions comprising WSsoy, Fraction 5, Fraction 9, and/or bioactive peptide components of SPI. As described elsewhere herein, the present invention is based upon the finding that WSsoy, Fraction 5, Fraction 9, and/or bioactive peptide components of SPI enhances wound healing and tissue regeneration. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., anti-inflammatories, antibiotics, or analgesic agents.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, *Remington's* Pharmaceutical Sciences, Mack Publishing Co., Easton, PA), which is incorporated herein by reference.

In an embodiment, the composition includes an antioxidant and a chelating agent that inhibits the degradation of one or more components of WSsoy, Fraction 5, Fraction 9, and/or bioactive peptide components of SPI. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of WSsoy, Fraction 5, Fraction 9, and/or bioactive peptide components of SPI in an aqueous or oily vehicle. Aqueous vehicles include, for example, water, and isotonic saline. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

In certain instances, one benefit of the composition of the present invention is that it has the ability to fill irregular and deep wounds. Thus, in one embodiment, the pharmaceutical composition may be topically applied to a wound or to a site in need of tissue regeneration.

Formulations suitable for topical administration include, but are not limited to, liquid or semi-liquid preparations such as liniments, lotions, oil-in-water or water-in-oil emulsions such as hydrogels, creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent in the presence of excipients. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the formulations suitable for topical administration may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone and their formulation, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

Formulations suitable for topical administration should be applied in an amount effective to affect desired changes. As used herein "amount effective" shall mean an amount sufficient to cover the region of skin surface where a change is desired. An active compound should be present in the amount of from about 0.0001% to about 50% by weight volume of the composition. More preferable, it should be present in an amount from about 0.0005% to about 15% of the composition; most preferably, it should be present in an amount of from about 0.001% to about 5% of the composition. Such compounds may be synthetically- or naturally derived.

In another embodiment, the pharmaceutical composition comprising WSsoy, Fraction 5, Fraction 9, and/or bioactive peptide components of SPI may be applied to a bandage or dressing, which is then applied to the wound or treatment site of a subject. For example, in one embodiment, a dressing is soaked in a liquid solution or liquid suspension comprising WSsoy, Fraction 5, Fraction 9, and/or bioactive peptide components of SPI. In another embodiment, an ointment comprising WSsoy, Fraction 5, Fraction 9, and/or bioactive peptide components of SPI is applied to a surface of a dressing or bandage.

In another embodiment, the pharmaceutical composition comprises an aerosolized or atomized solution or suspension comprising WSsoy, Fraction 5, Fraction 9, and/or bioactive peptide components of SPI. Such aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Scaffolds

The invention provides the use of WSsoy, Fraction 5, Fraction 9, and/or bioactive peptide components of SPI for the generation of a biomaterial useful for engineering applications. As described herein, WSsoy and bioactive components thereof can be used in the production of a scaffold that supports cell migration, cell proliferation, and angiogenesis and thus can be used in various tissue engineering applications, including wound healing.

For example, in one embodiment, WSsoy, Fraction 5, Fraction 9, and/or bioactive peptide components of SPI is incorporated within a scaffold. In one embodiment, WSsoy, Fraction 5, Fraction 9, and/or bioactive peptide components of SPI is applied to the surface of a scaffold. The scaffold of the invention may be of any type known in the art. Non-limiting examples of such a scaffold includes a, hydrogel, electrospun scaffold, foam, mesh, sheet, patch, and sponge.

Hydrogels

In one embodiment, the present invention provides a hydrogel comprising WSsoy, Fraction 5, Fraction 9, and/or bioactive peptide components of SPI. Hydrogels can generally absorb a great deal of fluid and, at equilibrium, typically are composed of 60-90% fluid and only 10-30% polymer. In a preferred embodiment, the water content of hydrogel is about 70-80%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility may be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66; Peppas and Mikos. Preparation Methods and Structure of Hydrogels in Hydrogels in Medicine and Pharmacy, Peppas, Ed. 1986, CRC Press: Boca Raton, Fla., pp 1-27). The hydrogels may be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose. (see.: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical cross-linking synthetic polymers include but are not limited to (meth)acrylate-oligolactide-PEO-oligolactide-(meth)acrylate, poly(ethylene glycol) diacrylate (PEGDA), poly(ethylene glycol) (PEO), poly(propylene glycol) (PPO), PEO—PPO-PEO copolymers (Pluronics), poly(phosphazene), poly (methacrylates), poly(N-vinylpyrrolidone), PL(G)A-PEO-PL(G)A copolymers, poly(ethylene imine), etc. (see A. S Hoffman, 2002, Adv. Drug Del. Rev, 43, 3-12).

In one embodiment, the hydrogel comprises at least one biopolymer. In other embodiments, the hydrogel scaffold further comprises at least two biopolymers. In yet other embodiments, the hydrogel scaffold comprises at least one biopolymer and at least one synthetic polymer.

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels may also be made degradable in vivo by incorporating PLA, PLGA or PGA polymers. Moreover, hydrogels may be modified with fibronectin, laminin, vitronectin, or, for example, RGD for surface modification, which may promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes may influence strength, elasticity, and degradation properties of the instant hydrogels (Nguyen and West, 2002, Biomaterials 23(22):4307-14; Ifkovits and Burkick, 2007, Tissue Eng. 13(10):2369-85).

Hydrogels may also be modified with functional groups for covalently attaching a variety of proteins (e.g., collagen) or compounds such as therapeutic agents. Therapeutic agents which may be linked to the matrix include, but are not limited to, analgesics, anesthetics, antifungals, antibiotics, anti-inflammatories, anthelmintics, antidotes, antiemetics, antihistamines, antihypertensives, antimalarials, antimicrobials, antipyretics, antiseptics, antiarthritics, antivirals, chemotherapeutic agents, a colored or fluorescent imaging agent, corticoids (such as steroids), diagnostic aids, enzymes, hormonesminerals, parasympathomimetics, potassium supplements, radiation sensitizers, sedatives, sulfonamides, sympathomimetics, tranquilizers, vasoconstrictors, vasodilators, vitamins, xanthine derivatives, and the like. The therapeutic agent may also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix may be via a protease sensitive linker or other biodegradable linkage. Molecules which may be incorporated into the hydrogel matrix include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

In certain embodiments, one or more multifunctional cross-linking agents may be utilized as reactive moieties that covalently link biopolymers or synthetic polymers. Such bifunctional cross-linking agents may include glutaraldehyde, genipin, epoxides (e.g., bis-oxiranes), oxidized dextran, p-azidobenzoyl hydrazide, N-[α-maleimidoacetoxy] succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NETS) and other bifunctional cross-linking reagents known to those skilled in the art. It should be appreciated by those in skilled in the art that the mechanical properties of the hydrogel are greatly influenced by the cross-linking time and the amount of cross-linking agents.

In another embodiment utilizing a cross-linking agent, polyacrylated materials, such as ethoxylated (20) trimethylpropane triacrylate, may be used as a non-specific photo-activated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Continuous exposure of this reactive mixture to long-wavelength light (>498 nm) would produce a cross-linked hydrogel network.

In one embodiment, the hydrogel comprises a UV sensitive curing agent which initiates hydrogel polymerization. For example, in one embodiment, a hydrogel comprises the photoinitiator 4-(2-hydroxyethoxy)phenyl-(2-hydroxy-2-propyl)ketone. In one embodiment, polymerization is induced by 4-(2-hydroxyethoxy)phenyl-(2-hydroxy-2-propyl)ketone upon application of UV light. Other examples of UV sensitive curing agents include 2-hydroxy-2-methyl-1- phenylpropan-2-one, 4-(2-hydroxyethoxy)phenyl (2-hydroxy-2-phenyl-2-hydroxy-2-propyl)ketone, 2,2-dimethoxy-2-phenyl-acetophenone 1-[4-(2-Hydroxyethoxy)-phenyl]-2-hydroxy-2-methyl-1-propane-1-one, 1-hydroxycyclohexylphenyl ketone, trimethyl benzoyl diphenyl phosphine oxide and mixtures thereof.

The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent may include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents may be added to the matrix composition before or during the crosslinking of the high molecular weight components.

In one embodiment, WSsoy, Fraction 5, Fraction 9, and/or bioactive peptide components of SPI is incorporated into the hydrogel. For example, WSsoy, Fraction 5, Fraction 9, and/or bioactive peptide components of SPI may be added to the hydrogel solution prior to gelation or polymerization of the gel. WSsoy, Fraction 5, Fraction 9, and/or bioactive peptide components of SPI may be added to hydrogel solution in any amount desired to produce a desired effect. In one embodiment, the ratio of WSsoy, Fraction 5, Fraction 9, and/or bioactive peptide components of SPI to hydrogel solution ranges from about 10:1 to 1:10. In another embodiment, the ratio of WSsoy, Fraction 5, Fraction 9, and/or bioactive peptide components of SPI to hydrogel solution ranges from about 5:1 to 1:5. In another embodiment, the ratio of WSsoy, Fraction 5, Fraction 9, and/or bioactive peptide components of SPI to hydrogel solution is 1:1. In this way, components of WSsoy, Fraction 5, Fraction 9, and/or bioactive peptide components of SPI become interspersed within the hydrogel. In another embodiment, the polymerized hydrogel is coated with an effective amount of WSsoy, Fraction 5, Fraction 9, and/or bioactive peptide components of SPI. In some embodiments, the hydrogel permits diffusion of WSsoy, Fraction 5, Fraction 9, and/or bioactive peptide components of SPI into and throughout the hydrogel.

Electrospun Scaffolds

The invention provides fibers as well as nanofibrous biocompatible biomatrices electrospun from a natural product such as soy. In some instances, the natural product is blended with a biopolymer and/or a synthetic polymer, such as poly(ethylene oxide) (PEO) to produce a tissue engineering scaffold. In certain embodiments, the particular blends provide a unique mix of mechanical and physical properties that facilitates cell penetration and proliferation within the scaffolds without crosslinking.

The scaffolds of the invention can be produced in a variety of ways. In an exemplary embodiment, the scaffold can be produced by electrospinning. Electrospinning is an atomization process of a conducting fluid which exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material can be collected as an interconnected web containing relatively fine, i.e. small diameter, fibers. The resulting films (or membranes) from these small diameter fibers have very large surface area to volume ratios and small pore sizes. A detailed description of electrospinning apparatus is provided in Zong, et al., 2002 Polymer 43: 4403-4412; Rosen et al., 1990 *Ann Plast Surg* 25: 375-87; Kim, K., Biomaterials 2003, 24: 4977-85; Zong, X., 2005 Biomaterials 26: 5330-8. After electrospinnning, extrusion and molding can be utilized to further fashion the polymers. To modulate fiber organization into aligned fibrous polymer scaffolds, the use of patterned electrodes, wire drum collectors, or post-processing methods such as uniaxial stretching has been successful. Zong, X., 2005 Biomaterials 26: 5330-8; Katta, P., 2004 *Nano Lett* 4: 2215-2218; Li, D., 2005 *Nano Lett* 5: 913-6.

The protein solution comprising WSsoy, Fraction 5, Fraction 9, and/or bioactive peptide components of SPI, can be produced in one of several ways. One method involves dissolving the soy protein isolate, or bioactive components of WSsoy, in an appropriate solvent. This process can be accomplished in a syringe assembly or it can be subsequently loaded into a syringe assembly. Another method involves purchasing commercially available polymer solutions or commercially available polymers and dissolving them to create polymer solutions. For example, poly(ethylene oxide) (PEO) can be purchased from Sigma (Sigma, St. Louis, Mo.), poly-L-lactide (PLLA) can be purchased from DuPont (Wilmington, Del.), poly(lactide-co-glycolide) can be purchased from Ethicon (Somerville, N.J.). Additional polymer scaffold components of the invention, such as cells and biomolecules, are also commercially available from suppliers.

In certain embodiments, the soy protein isolate or bioactive component of WSsoy is first dissolved in a solvent. For example, in one embodiment, the solvent is water or other suitable buffer. In certain embodiments, the solvent is devoid of harsh organic solvents, such as N,N-Dimethyl formamide (DMF), tetrahydrofuran (THF), methylene chloride, dioxane, ethanol, hexafluoroisopropanol (HFIP), chloroform, 1,1,1,3,3,3-hexafluoro-2-propanol (HFP), or glacial acetic acid.

The protein solution can optionally contain a salt which creates an excess charge effect to facilitate the electrospinning process. Examples of suitable salts include NaCl, $KH_2PO_4$, $K_2HPO_4$, $KIO_3$, KCl, $MgSO_4$, $MgCl_2$, $NaHCO_3$, $CaCl_2$) or mixtures of these salts.

The protein solution forming the conducting fluid preferably has a protein concentration in the range of about 1 to about 80 wt %, more preferably about 8 to about 60 wt %.

The electric field created in the electrospinning process preferably is in the range of about 5 to about 100 kilovolts (kV), more preferably about 10 to about 50 kV. The feed rate of the conducting fluid to the spinneret (or electrode) preferably is in the range of about 0.1 to about 1000 microliters/min, more preferably about 1 to about 250 microliters/min.

The single or multiple spinnerets sit on a platform which is capable of being adjusted, varying the distance between the platform and the grounded collector substrate. The distance can be any distance which allows the solvent to essentially completely evaporate prior to the contact of the polymer with the grounded collector substrate. In an exemplary embodiment, this distance can vary from 1 cm to 25 cm. Increasing the distance between the grounded collector substrate and the platform generally produces thinner fibers.

In electrospinning cases where a rotating mandrel is required, the mandrel is mechanically attached to a motor, often through a drill chuck. In an exemplary embodiment, the motor rotates the mandrel at a speed of between about 1 revolution per minute (rpm) to about 500 rpm. In an exemplary embodiment, the motor rotation speed of between about 200 rpm to about 500 rpm. In another exemplary embodiment, the motor rotation speed of between about 1 rpm to about 100 rpm.

Additional embodiments or modifications to the electrospinning process and apparatus are described herein.

The invention also includes combinations of natural materials, combinations of synthetic materials, and combinations of both natural and synthetic materials. Examples of combinations include, but are not limited to: blends of different types of collagen (e.g. Type I with Type II, Type I with Type III, Type II with Type III, etc.); blends of one or more types of collagen with fibrinogen, thrombin, elastin, PGA, PLA, and polydioxanone; and blends of fibrinogen with one or more types of collagen, thrombin, elastin, PGA, PLA, and polydioxanone.

The electroprocessed material of the present invention can result from the electroprocessing of natural materials, synthetic materials, or combinations thereof. Examples include but are not limited to amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans.

Some preferred materials to be electroprocessed are naturally occurring extracellular matrix materials and blends of naturally occurring extracellular matrix materials, including but not limited to collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, and proteoglycans. Especially preferred materials for electroprocessing include collagen, fibrin, fibrinogen, thrombin, fibronectin, and combinations thereof. Some collagens that are used include but are not limited to collagen types I, II, III, IV, V, VI, VII, VIII, IX, X, XI, XII, XIII, XIV, XV, XVI, XVII, XVIII, and XIX. Some preferred collagens include types I, II, and III. These proteins may be in any form, including but not limited to native and denatured forms. Other preferred materials for electroprocessing are carbohydrates such as polysaccharides (e.g. cellulose and its derivatives), chitin, chitosan, alginic acids, and alginates such as calcium alginate and sodium alginate. These materials may be isolated from plant products, humans or other organisms or cells or synthetically manufactured. Some especially preferred natural materials for electroprocessing are collagen, fibrinogen, thrombin, fibrin, fibronectin, and combinations thereof. Also included are crude extracts of tissue, extracellular matrix material, extracts of non-natural tissue, or extracellular matrix materials (i.e. extracts of cancerous tissue), alone or in combination. Extracts of biological materials, including but are not limited to cells, tissues, organs, and tumors may also be electroprocessed.

Collagen and fibrinogen can each been electrospun to produce fibers having repeating, band patterns along the length of the fibers. These patterns are observable, for example with transmission electron microscopy, and are typical of those produced by natural processes. In some embodiments, the banded pattern observed in electrospun collagen fibers is the same as that produced by cells in vivo. In some embodiments, the banding pattern in electrospun fibrinogen is the same as that of fibrinogen found in normal clots formed in vivo. While not wishing to be bound by any particular theory, it is believed that the banding apparent along natural collagen fibers results from the helical pattern of the protein chains in the collagen, while the banding in fibrinogen in vivo results from close packing of individual fibrin molecules in a stacked configuration. In some of these embodiments, the compositions are composed of fibrous webs rather than networks characteristic of fibrin clots. Further, in some embodiments, electroprocessed fibrinogen is not soluble in water, unlike native fibrinogen.

The invention includes all natural or natural-synthetic hybrid compositions that result from the electroprocessing of any material. Materials that change in composition or structure before, during, or after electroprocessing are within the scope of the invention.

It is to be understood that these electroprocessed materials may be combined with other materials and/or substances in forming the compositions of the present invention. Electroprocessed materials in some embodiments are prepared at very basic or acidic pHs (for example, by electroprocessing from a solution having a specific pH) to accomplish the same effect. As another example, an electroprocessed matrix, containing cells, may be combined with an electroprocessed biologically compatible polymer and growth factors to stimulate growth and division of the cells in the electroprocessed matrix.

Synthetic materials electroprocessed for use in the scaffold include any materials prepared through any method of artificial synthesis, processing, isolation, or manufacture. The synthetic materials are preferably biologically compatible for administration in vivo or in vitro. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Some preferred synthetic materials include PLA, PGA, copolymers of PLA and PGA, polycaprolactone, poly(ethylene-co-vinyl acetate), EVOH, PVA, and PEO. Polymers with cationic moieties are also preferred in some embodiments. Examples of such polymers include, but are not limited to, poly(allyl amine), poly (ethylene imine), poly(lysine), and poly(arginine). The polymers may have any molecular structure including, but not limited to, linear, branched, graft, block, star, comb and dendrimer structures. Matrices can be formed of electrospun fibers, electroaerosol, electrosprayed, or electrosputtered droplets, electroprocessed powders or particles, or a combination of the foregoing.

By selecting different natural and synthetic materials, or combinations thereof, many characteristics of the scaffold are manipulated. The properties of the matrix comprised of electroprocessed material and a substance may be adjusted. In addition, selection of materials for electroprocessing can affect the permanency of an implanted matrix. For example, many matrices made by electroprocessing fibrinogen or fibrin may degrade more rapidly while many matrices made of collagen are more durable and many other matrices made by electroprocessing materials are more durable still. Thus, for example, incorporation of durable synthetic polymers (e.g. PLA, PGA) increase the durability and structural strength of matrices electroprocessed from solutions of fibrinogen in some embodiments. Use of matrices made by electroprocessing natural materials such as WSsoy also minimize rejection or immunological response to an implanted matrix. Accordingly, selection of materials for electroprocessing and use in substance delivery is influenced by the desired use.

In one embodiment, a skin patch comprising electroprocessed WSsoy, Fraction 5, Fraction 9, and/or bioactive peptide components of SPI, is combined with healing promoters, analgesics and or anesthetics and anti-rejection substances and applied to the skin and may subsequently dissolve into the skin. In embodiments in which the matrix contains substances that are to be released from the matrix, incorporating electroprocessed synthetic components, such as biocompatible substances, can modulate the release of substances from an electroprocessed composition. For example, layered or laminate structures can be used to control the substance release profile. Unlayered structures can also be used, in which case the release is controlled by the relative stability of each component of the construct. For example, layered structures composed of alternating electroprocessed materials are prepared by sequentially electroprocessing different materials onto a target. The outer layers are, for example, tailored to dissolve faster or slower than the inner layers. Multiple agents can be delivered by this method, optionally at different release rates. Layers can be tailored to provide a complex, multi-kinetic release profile of a single agent over time. Using combinations of the foregoing provides for release of multiple substances released, each with its own profile. Complex profiles are possible.

Natural components such as biocompatible substances can be used to modulate the release of electroprocessed materials or of substances from an electroprocessed composition. For example, a drug or series of drugs or other materials or substances to be released in a controlled fashion can be electroprocessed into a series of layers. The layered construct can be implanted, and as the successive layers dissolve or break down, the drug (or drugs) is released in turn as each successive layer erodes. In some embodiments, unlayered structures are used, and release is controlled by the relative stability of each component of the construct.

In some embodiments, the electroprocessed material itself may provide a therapeutic effect. For example, as described herein Fraction 9 comprises bioactive components which confer their activity in their immobilized state by acting as a ligand for $\alpha 9\beta 1$ integrin. Therefore, electroprocessed WSsoy and/or Fraction 9 of SPI provides a therapeutic effect.

Non-limiting examples of a material that has a therapeutic effect is electroprocessed fibrinogen, thrombin, fibrin, or combinations thereof. For example, thrombin converts fibrinogen to fibrin. Fibrin assists in arrest of bleeding (hemostasis). Fibrin is a component of the provisional matrix that is laid down during the early stages of healing and may also promote the growth of vasculature in adjacent region. In many ways fibrin is a natural healing promoter. In some embodiments, electroprocessed fibrinogen also assists in healing. When placed in contact with a wound of a patient, such an electroprocessed material provides the same healing properties as fibrin.

In certain embodiments, the scaffold further comprises soluble bioactive WSsoy components. For example, it is described herein that Fraction 5 confers its bioactive activity in its soluble form. Thus, the scaffold may comprise WSsoy and/or Fraction 5 within the electrospun scaffold. For example, the scaffold may comprise a hydrogel layer which releases soluble WSsoy and/or Fraction 5. In one embodiment, the electrospun scaffold comprises embedded microspheres comprising soluble WSsoy and/or Fraction 5.

Method for Forming Matrices or Scaffolds

The biocompatible scaffold may be shaped using methods such as, for example, solvent casting, compression molding, filament drawing, meshing, leaching, weaving, foaming, electrospinning and coating. In solvent casting, a solution of one or more proteins in an appropriate solvent, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the artificial organ. Next a solvent is used to dissolve away one of the components, resulting in pore formation. (See U.S. Pat. No. 5,514,378 to Mikos).

The scaffold may be shaped into any number of desirable configurations to satisfy any number of overall system, geometry or space restrictions. For example, the matrix or scaffold may be shaped to conform to the dimensions and shapes of the whole or a part of the tissue being treated. The scaffold may be shaped in different sizes and shapes to conform to the organs or to the wounds of differently sized patients. The matrix or scaffold may also be shaped in other fashions to accommodate the special needs of the patient.

In one embodiment, the scaffolds are seeded with one or more populations of cells to form an artificial organ construct. The artificial organ construct can be autologous, where the cell populations are derived from the subject's own tissue, or allogenic, where the cell populations are derived from another subject within the same species as the patient. The artificial organ construct can also be xenogenic, where the different cell populations are derived form a mammalian species that is different from the subject. For example the cells can be derived from organs of mammals such as humans, monkeys, dogs, cats, mice, rats, cows, horses, pigs, goats and sheep.

Cells can be isolated from a number of sources, including, for example, biopsies from living subjects and whole-organ recover from cadavers. The isolated cells are preferably autologous cells, obtained by biopsy from the subject intended to be the recipient. For example, a biopsy of skeletal muscle from the arm, forearm, or lower extremities, or smooth muscle from the area treated with local anesthetic with a small amount of lidocaine injected subcutaneously, and expanded in culture. The biopsy can be obtained using a biopsy needle, a rapid action needle which makes the procedure quick and simple.

Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption can also be accomplished by a number of methods including, but not limited to, scraping the surface of the organ, the use of grinders, blenders, sieves, homogenizers, pressure cells, or insonicators.

Preferred cell types include, but are not limited to, urothelial cells, mesenchymal cells, especially smooth or skeletal muscle cells, myocytes (muscle stem cells), fibroblasts, chondrocytes, adipocytes, fibromyoblasts, and ectodermal cells, including ductile and skin cells, hepotocytes, Islet cells, cells present in the intestine, and other parenchymal cells, osteoblasts and other cells forming bone or cartilage. In some cases, it may also be desirable to include nerve cells. In other cases, it mal be desirable to include stem cells.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting.

Cell fractionation may also be desirable, for example, when the donor has diseases such as cancer or metastasis of other tumors to the desired tissue. A cell population may be sorted to separate malignant cells or other tumor cells from normal noncancerous cells. The normal noncancerous cells, isolated from one or more sorting techniques, may then be used for organ reconstruction.

Isolated cells can be cultured in vitro to increase the number of cells available for coating the biocompatible scaffold. The use of allogenic cells, and more preferably autologous cells, is preferred to prevent tissue rejection. However, if an immunological response does occur in the subject after implantation of the artificial organ, the subject may be treated with immunosuppressive agents such as, cyclosporin or FK506, to reduce the likelihood of rejection. In certain embodiments, chimeric cells, or cells from a transgenic animal, can be coated onto the biocompatible scaffold. Isolated cells may be transfected prior to coating with genetic material.

Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery.

Isolated cells can be normal or genetically engineered to provide additional or normal function. Methods for genetically engineering cells with retroviral vectors, polyethylene glycol, or other methods known to those skilled in the art can be used. These include using expression vectors which transport and express nucleic acid molecules in the cells. (See Goeddel; Gene Expression Technology: Methods in Enzymology 185, Academic Press, San Diego, Calif. (1990).

Vector DNA is introduced into prokaryotic or cells via conventional transformation or transfection techniques. Suitable methods for transforming or transfecting host cells can be found in Sambrook et al. (*Molecular Cloning: A Laboratory Manual,* 3nd Edition, Cold Spring Harbor Laboratory press (2001)), and other laboratory textbooks.

Seeding of cells onto the matrix or scaffold can be performed according to standard methods. For example, the seeding of cells onto polymeric substrates for use in tissue repair has been reported (see, e.g., Atala, A. et al., J. Urol. 148(2 Pt 2): 658-62 (1992); Atala, A., et al. J. Urol. 150 (2 Pt 2): 608-12 (1993)). Cells grown in culture can be trypsinized to separate the cells, and the separated cells can be seeded on the matrix. Alternatively, cells obtained from cell culture can be lifted from a culture plate as a cell layer, and the cell layer can be directly seeded onto the scaffold without prior separation of the cells.

In a preferred embodiment, in the range of 1 million to 700 50 million cells are suspended in medium and applied to each square centimeter of a surface of a scaffold. Preferably, between 1 million and 50 million cells, and more preferably, between 1 million and 10 million cells are suspended in media and applied to each square centimeter of a surface of a scaffold. The matrix or scaffold is incubated under standard culturing conditions, such as, for example, 37° C., 5% $CO_2$, for a period of time until the cells attached. However, it will be appreciated that the density of cells seeded onto the scaffold can be varied. For example, greater cell densities promote greater tissue regeneration by the seeded cells, while lesser densities may permit relatively greater regeneration of tissue by cells infiltrating the graft from the host. Other seeding techniques may also be used depending on the matrix or scaffold and the cells. For example, the cells may be applied to the matrix or scaffold by vacuum filtration. Selection of cell types, and seeding of cells onto a scaffold, will be routine to one of ordinary skill in the art in light of the teachings herein.

In one embodiment, the scaffold is seeded with one population of cells to form an artificial organ construct. In another embodiment, the matrix or scaffold is seeded on two sides with two different populations of cells. This may be performed by first seeding one side of the matrix or scaffold and then seeding the other side. For example, the scaffold may be placed with one side on top and seeded. Then the matrix or scaffold may be repositioned so that a second side is on top. The second side may then be seeded with a second population of cells. Alternatively, both sides of the matrix or scaffold may be seeded at the same time. For example, two cell chambers may be positioned on both sides (i.e., a sandwich) of the scaffold. The two chambers may be filled with different cell populations to seed both sides of the matrix or scaffold simultaneously. The sandwiched scaffold may be rotated, or flipped frequently to allow equal attachment opportunity for both cell populations. Simultaneous seeding may be preferred when the pores of the matrix or scaffold are sufficiently large for cell passage from one side to the other side. Seeding the scaffold on both sides simultaneously can reduce the likelihood that the cells would migrate to the opposite side.

In another embodiment, two separate scaffolds may be seeded with different cell populations. After seeding, the two matrices may be attached together to form a single matrix or scaffold with two different cell populations on the two sides. Attachment of the scaffolds to each other may be performed using standard procedures such as fibrin glue, liquid co-polymers, sutures and the like.

In order to facilitate cell growth on the scaffold of the present invention, the scaffold may be coated with one or more cell adhesion-enhancing agents. These agents include but are not limited collagen, laminin, and fibronectin. The scaffold may also contain cells cultured on the scaffold to form a target tissue substitute. The target tissue that may be formed using the scaffold of the present invention may be an arterial blood vessel, wherein an array of microfibers is arranged to mimic the configuration of elastin in the medial layer of an arterial blood vessel. In the alternative, other cells may be cultured on the scaffold of the present invention. These cells include, but are not limited to, cells cultured on the scaffold to form a blood vessel substitute, epithelial cells cultured on the scaffold to form epithelial tissue, muscle cells cultured on the scaffold to form muscle tissue, endothelial cells cultured on the scaffold to form endothelial tissue, skeletal muscle cells cultured on the scaffold to form skeletal muscle tissue, cardiac muscle cells cultured on the scaffold to form cardiac muscle tissue, collagen fibers cultured on the scaffold to form cartilage, interstitial valvular cells cultured on the scaffold to form valvular tissue and mixtures thereof.

Therapeutic Application

Grafting of scaffolds to an organ or tissue to be augmented can be performed according to the methods described in herein or according to art-recognized methods. The matrix or scaffold can be grafted to an organ or tissue of the subject by suturing the graft material to the target organ. Implanting a neo-organ construct for total organ replacement can be performed according to the methods described herein or according to art-recognized surgical methods. The scaffold is also useful for delivery of biologics, enzymes that activate drugs, protease inhibitors, and the like.

In one embodiment, the invention includes the use of the natural protein based scaffolds as a platform to direct wound healing by the induction of native skin fibroblasts and keratinocytes to populate the scaffolds and secrete appropriate matrix components. In some instances, the scaffold can also include desirable cells. For example, the scaffold can included cells that have the ability to express angiogenic growth factors and cytokines, secrete wound healing related cytokines, secrete collagen, and promote wound healing in vivo.

Scaffolds of the invention described can be useful for clinical and personal wound care and soft tissue regeneration. In one aspect of the invention, scaffold is used as a wound dressing or graft for external skin wounds. In a clinical setting, the scaffold can be used to treat wounds resulting from trauma, burns, ulcers, abrasions, lacerations, surgery, or other damage. Surgeons can use these grafts to cover and protect the wound area, to temporarily replace lost or damaged skin tissue, and to guide new tissue generation and wound healing into the damaged area. In a clinical setting, the scaffold may be secured to the wound area using sutures, adhesives, or overlaying bandages. The scaffold may be cut to match the size of the wound, or may overlap the wound edges.

In another aspect of the invention, the scaffold may be tailored for personal/home care by combining the sheet with an adhesive backing to create a scaffold bandage. An adhesive section can hold the scaffold in place on a wounded area and can be removed when the fibers degrade or fuse with the tissue. The scaffold sheet may also be secured with a liquid or gel adhesive.

In another aspect of the invention, scaffold sheets can be used as gauze to absorb fluid and protect large wounds. This scaffold gauze can be wrapped around a wounded area or secured with tape.

In another aspect of the invention, scaffold sheets can be used to treat internal soft tissue wounds such as wounds in the amniotic sac, ulcers in the gastrointestinal tract or mucous membranes, gingival damage or recession, internal surgical incisions or biopsies, etc. The scaffold grafts can be sutured or adhered into place to fill or cover the damaged tissue area.

The scaffold has numerous characteristics that are useful for wound healing. First, the polymer scaffolds described herein that include nanofibers are both nano-porous and breathable. They can prevent microbes and infectious particles from crossing through, but they allow air flow and moisture penetration which are critical in natural wound healing.

Second, the fibers in this invention are biodegradable, which allows for temporary wound coverage followed by eventual ingrowth of new tissue. The choice of material for scaffold wound dressings can be determined to match the natural tissue characteristics including mechanical strength and rate of degradation/tissue regeneration.

Third, the scaffolds may be embedded or conjugated with various factors which may be released upon degradation. These factors may include, but are not limited to epidermal growth factor (EGF), platelet derived growth factor (PDGF), basic fibroblast growth factor (bFGF), transforming growth factor-β (TGF-β), and tissue inhibitors of metalloproteinases (TIMP), which have been shown to be beneficial in wound healing. Additional wound healing factors such as antibiotics, bacteriocides, fungicides, silver-containing agents, analgesics, and nitric oxide releasing compounds can also be incorporated into the scaffold wound dressings or grafts.

Fourth, scaffold grafts for wound healing may be seeded with cells for faster tissue regeneration and more natural tissue structure. These cells may include, but are not limited to fibroblasts, keratinocytes, epithelial cells, endothelial cells, mesenchymal stem cells, and/or embryonic stem cells.

Fifth, the nano-scale architecture of the nanofibrous scaffolds closely mimics that of the extracellular matrix (ECM) of many common soft tissues. For example, the nano-scale fibers are structurally similar to collagen fibrils found in skin and other tissues. This architecture may prevent scar formation by providing an organized scaffold for cells to migrate into a wound. In this aspect of the invention, alignment of the scaffold is preferred to keep cells aligned and organized, rather than allowing them to arrange randomly as in the formation of scar tissue. Aligned scaffolds may be oriented with respect to a given axis of the wound to allow faster tissue ingrowth and wound coverage.

Scaffold alignment can also be used to closely match the architecture of natural tissue ECM. This may include fiber alignment in a single direction, criss-cross alignment in orthogonal directions, or more complicated fiber architecture. In this instance of the invention, the scaffold includes multiple layers of fibers with specific fiber orientation in each layer. Similarly, each individual scaffold layer may also contain a specific factor or cell type such as the ones listed previously. This allows for creation of polymer scaffolds that can closely match natural tissue architecture and composition. For example, a simple scaffold wound dressing or graft might include a single layer of aligned fibers. On the other hand, a more complex scaffold skin graft might include multiple aligned fiber sheets layered in a criss-cross pattern with fibroblasts in the bottom sheets and keratinocytes in the top sheet, as well as bFGF in the bottom sheets and an antimicrobial agent in the top sheet. Other such combinations are possible, depending on the specific needs of the patient.

In another embodiment, the scaffold can include a therapeutic agent. The therapeutic agent can be an anti-tumor agent including but not limited to a chemotherapeutic agent, an anti-cell proliferation agent or any combination thereof.

The invention also encompasses tissue regeneration applications. The objective of the tissue regeneration therapy approach is to deliver high densities of repair-competent cells (or cells that can become competent when influenced by the local environment) to the defect site in a format that optimizes both initial wound mechanics and eventual neotissue production.

The composition of the invention may be administered to an individual in need thereof in a wide variety of ways. Preferred modes of administration include intravenous, intravascular, intramuscular, subcutaneous, intracerebral, intraperitoneal, soft tissue injection, surgical placement, arthroscopic placement, and percutaneous insertion, e.g. direct injection, cannulation or catheterization. Most preferred methods result in localized administration of the inventive composition to the site or sites of tissue defect. Any administration may be a single application of a composition of invention or multiple applications. Administrations may be to single site or to more than one site in the individual to be treated. Multiple administrations may occur essentially at the same time or separated in time.

Self-Assembling Compositions

The present invention also provides self-assembling compositions comprising WSsoy. Purified WSsoy can, under certain conditions, unexpectedly self-assemble into matrices. Self-assembly refers to the spontaneous association and bonding between individual water-soluble soy proteins to form higher order structures, such as fibers, films, sheets, bundles, and lattices. WSsoy in a dry form does not exhibit any spontaneous association. When dry WSsoy particles are suspended in an aqueous environment within certain concentration ranges, the intermolecular contacts are sufficient to enable the WSsoy to self-assemble into higher order structures to form matrices. In various embodiments, different wet WSsoy compositions may exhibit characteristics ranging from slightly viscous liquids, flowable gels (FIG. 23), flowable pastes with delayed gelling, and spontaneously forming hard gels.

In some embodiments, the present invention comprises dry WSsoy compositions. Dry WSsoy compositions are useful in applications where treatment is for a wound site that is moist, such as a fresh wound. Dry WSsoy compositions typically comprise WSsoy in granular or powder form. For example, dry WSsoy particles can be between 1 and 1000 μm in diameter. In some embodiments, the dry WSsoy particles have a uniform size, while in other embodiments, the dry WSsoy particles have various sizes. As would be understood by a person skilled in the art, the particle size ranges described herein are not absolute ranges. For example, a dry WSsoy particle mixture of the present invention with a size range of about 200-500 microns can contain a portion of particles that are smaller or larger than the about 200-500 microns range. In some embodiments, the particle size range represents a particles size distribution (PSD) wherein a percentage of the particles of the mixture lie within the listed range. For example, a dry WSsoy particle size range of about 200-500 microns can represent a mixture of dry WSsoy particles having at least 50% of the particles in the range of about 200-500 microns, but more preferably a higher percentage, such as, but not limited to: 60%, 70%, 80%, 90%, 95%, 97%, 98% or even 99%.

It should be appreciated that the particles of the dry compositions may be spherical or of any other shape desired. In one embodiment the particles may have an uneven or a “dimpled” surface. In such embodiments, the uneven surface may increase the ability of additional components to cling to the particles and produce a uniform coating. In some embodiments, particles having such a shape may be more readily adhered, and to remain adhered, to the wound of a subject, thereby improving the ability of the dry compositions to self-assemble into a wound healing matrix.

In certain embodiments, the dry WSsoy compositions comprise only dry WSsoy. In other embodiments, the dry WSsoy compositions comprises additional dry elements. For example, the dry compositions may further comprise excipients such as bulking agents. Bulking agents may include any suitable water-soluble and biocompatible material that is generally solid at room temperature, such as stearic acid, starch, and talc.

In other embodiments, the dry WSsoy compositions may further comprise pharmaceutical and therapeutic components such as: anesthetics, antiallergics, antihistamines, antipruritics, muscle relaxants, analgesics, antipyretics, vitamins, antimicrobial agents, antiseptics, disinfectants, fungicides, ectoparasiticides, antiparasitics, alkaloids, salts, ions, anti-inflammatories, wound healing agents, plant extracts, growth factors, polycarbonates, extracellular matrix (ECM) constituents such as ECM proteins, emollients, antibacterial or antiviral agents, tranquilizers, antitussives, nanoparticles such as silver ions, and the like.

In other embodiments, the dry WSsoy compositions may further comprise an additional polymer. Non-limiting examples of polymers include: polyurethane, polysiloxane or silicone, polyethylene, polyvinyl pyrrolidone, poly(2-hydroxy ethyl methacrylate), poly(N-vinyl pyrrolidone), polymethyl methacrylate, polyvinyl alcohol, polyacrylic acid, polyacrylamide, polyethylene-co-vinyl acetate, polyethylene glycol, polyethylene oxide, polymethacrylic acid, polylactide (PLA), polyglycolide (PGA), poly(lactic-co-glycolic acid) (PLGA), polystyrene, polyanhydride, polyorthoester, polycarbonate, and the like.

In some embodiments, the present invention comprises wet WSsoy compositions. Wet WSsoy compositions typically comprise WSsoy suspended in a liquid carrier, wherein the WSsoy self-assembles into a gel-like matrix. Suitable liquid carriers comprise biocompatible, nonreactive aqueous solutions such as the pharmaceutically acceptable carriers described elsewhere herein. In various embodiments, the liquid carrier may further comprise the soluble therapeutic components and additives described above.

The wet WSsoy compositions comprise WSsoy within a certain concentration range in a liquid carrier to provide gel-like matrices. For example, the concentration of WSsoy in liquid carrier can be between 1 and 200 mg/mL. In some embodiments, the concentration of WSsoy can be expressed as between 1 and 20 wt %.

In some embodiments, the liquid carrier may further comprise cells. Non-limiting examples include stem cells, progenitor cells, committed stem cells, and differentiated cells. Examples of "stem cells" include, but are not limited to, pluripotent stem cells, such as embryonic stem cells, induced pluripotent cells, or neonatal or adult multipotent stem cells, such as bone marrow stem cells, adipose stem cells, dental pulp stem cells, follicular stem cells, placental stem cells, and umbilical cord stem cells. Other cells include epidermal cells and stromal cells. In other embodiments, the liquid carrier may further comprise agents that promote cell growth and wound healing, such as growth factors, salts, ions, vitamins, antibodies, nucleic acids, proteins, electrolytes, peptides, polypeptides, carbohydrates, hormones, cytokines, and the like. In some embodiments, the liquid carrier may further comprise a gel or matrix forming material described elsewhere herein.

In some embodiments, a dry WSsoy composition may be provided with a liquid carrier. For example, a dry WSsoy composition and a liquid carrier may be provided separately, such that when combined just prior to application, a wet WSsoy composition may be prepared. Providing a dry WSsoy composition and a liquid carrier separately may improve shelf life and ease of manufacture. Allowing a user to prepare the wet WSsoy composition further provides flexibility in determining the final concentration of WSsoy in the wet composition, or even whether to use the liquid carrier at all.

It should be understood that the WSsoy of the present invention is not limited to the abovementioned wet and dry compositions. In various embodiments, the WSsoy component of the present invention is suitable for inclusion in an aerosol, a cream, an ointment, a patch, a wrapping, and the like. In other embodiments, the compositions of the present invention are suitable for use in electroprocessing (as defined above). Compositions comprising WSsoy may be electroprocessed to form sheets, fibers, fabrics, scaffolds, and the like, which are not irritating to the wound bed, are highly flexible, and do not need to be removed as they are biodegradable, avoiding unnecessary debridement of the wound bed. The electroprocessed compositions are environmentally friendly and do not require any toxic solvents during creation for either the operator or for the wound bed.

Methods of Use

WSsoy composition and applying it to a wound site in need of healing.

The amount of the WSsoy composition provided may be determined based on the size of the wound to be treated. For example, 1 to 100 mg of dry WSsoy composition or 0.1 to 1 mL of wet WSsoy composition may be provided for every 1 $cm^2$ of wound. In other embodiments, the amount of WSsoy composition provided may be determined based on the size and depth of the wound to be treated. Wounds may be described as partial thickness wounds or full thickness wounds. Persons skilled in the art will understand that partial thickness wounds refer to wounds comprising damage to the dermis or epidermis, while full thickness wounds refer to wounds comprising damage to the subcutaneous layer or deeper. The amount of a WSsoy composition provided for treating a wound may be adjusted depending on the wound type. For example, for two wounds having the same surface area but having different depths, more WSsoy composition may be used to treat the deeper wound. In some embodiments, the amount of WSsoy composition provided may be determined based on the desired thickness of application, such as a thickness between 50 and 5000 μm. In other embodiments, an exact amount of WSsoy composition may not be needed. For example, any amount of WSsoy composition may be applied to a wound, such that there is enough WSsoy composition to provide coverage to the entirety of the wound. Excess WSsoy composition may simply fall away or be removed by any other convenient means.

Application of a WSsoy composition to a wound site will vary with the type of WSsoy composition provided. For example, dry WSsoy compositions may be applied by sprinkling the composition on the wound site, dusting the composition on the wound site, or pouring the composition on the wound site. Wet WSsoy compositions may be applied by spray, injection, topical application, or pouring. In some embodiments, wet WSsoy compositions may be applied by a portable electrospinning device.

It should be appreciated that the WSsoy compositions disclosed herein are applicable for other cutaneous treatments. For example, the WSsoy compositions are amenable for treating topical ailments, abrasions (superficial wounds), preventative care, disinfection, as well as any other treatment of a simple 2D or complex 3D region of skin requiring a thin coating.

Kit for Treating Wounds

The present invention relates to kits comprising components useful within the methods of the invention and instructional material that describes, for instance, the method of using the WSsoy compositions as described elsewhere herein. The kit may comprise components and materials useful for performing the methods of the invention. For instance, the kit may comprise one or more containers, each holding a premeasured, ready to dispense amount of a dry WSsoy composition or a liquid carrier. In some embodiments, the kit may comprise at least two syringes, wherein at least one syringe is partially filled with a dry WSsoy composition, and at least one syringe is partially filled with a liquid carrier or able to accept a liquid carrier. The WSsoy composition may be prepared for use by joining the dispensing ends of the syringes together, wherein an operator may repeatedly depress one syringe to fill the other and mix the dry WSsoy with the liquid carrier.

In certain embodiments, the kit comprises instructional material. Instructional material may include a publication, a recording, a diagram, or any other medium of expression which can be used to communicate the functions of the kit described herein. The instructional material of the kit of the invention may, for example, be affixed to a package which contains one or more instruments which may be necessary for the desired procedure. Alternatively, the instructional material may be shipped separately from the package, or may be accessible electronically via a communications network, such as the Internet.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

In searching for such "smart" wound matrices, we previously described the beneficial effects of acellular scaffolds electrospun from common purified soy-protein isolate (SPI), which contain phytoestrogens, on the enhanced re-epithelialization and regeneration of appendages in rodents and pigs (Har-el, Y., et al., 2014, *Wound Medicine* 5, 9-15; Har-el, Y. et al. 2014, *Biomedical Engineering Society Annual Meeting*). The experiments presented herein demonstrate that wound matrices electrospun from water-soluble soy protein isolate (WSsoy), devoid of isoflavonoids, enhance the healing in a rodent model of full thickness cutaneous wounds.

Cutaneous wound healing is a complex, multi-step biological process, requiring a coordinated response by hematopoietic cells, fibroblasts, keratinocytes and endothelial cells (Demidova-Rice T. N., et al., 2012, *Advances in skin & wound care* 25, 304-314). The initial steps of wound healing include re-epithelialization (lateral migration of keratinocytes followed by inward migration of dermal fibroblasts) and angiogenesis (migration of dermal endothelial cells and capillary formation) (Tarnawski, A., 2000, *Drug news & perspectives* 13, 158-168; Johnson, K. E., et al. 2014, *Adv Wound Care* (New Rochelle) pp 647-661). During the re-epithelialization phase of wound healing, migration of keratinocytes, fibroblasts and endothelial cells into the wound requires rapid binding and dissociation from the extracellular matrix to enhance cell movement. These cell types express different integrins, which mediate their migration and attachment to ECM proteins. For example, in the normal epidermis, α3β1 and α6β4 integrins link keratinocytes to the basal membrane laminins (Carter, W. G., et al. 1990, *J Cell Biol* 111, 3141-3154) whereas α2β1, α5β1 and α9β1 integrins are crucial mediators of interaction of keratinocytes with collagen, fibronectin and tenascin during wound closure (Kim, J. P., et al., 1992, *J Cell Physiol* 151, 443-450; Mercurio, A. M., 2000, *Am J Pathol*, pp 3-6; Singh, P., et al., 2009, *J InvestDermatol* 129, 217-228). The spatial expression patterns of cellular fibronectin and α9β1 are distinct, but correlatively overlap in the dermal-epidermal junction (Singh, P., et al., 2004, J Invest Dermatol 123, 1176-1181). These observations suggest an important role for α9β1 in keratinocyte function following wounding. Moreover, the absence of integrin α9β1 results in defects in cell proliferation causing poor re-epithelialization (Singh, P., 2004, *J Invest Dermatol* 123, 1176-1181). The present data suggest that one of the mechanisms by which WSsoy-derived scaffolds enhance re-epithelialization is via bioactive proteinaceous components in WSsoy that may act as α9β1 integrin ligands.

Nutraceutical functions of natural food products for use in therapeutic applications is drawing considerable attention. Soybean bioactive peptides, (Singh, B. P. et al., 2014, *Peptides* 54, 171-179), taken as nutritional supplements, reportedly exhibit numerous health-enhancing properties, such as easing the symptoms of postmenopausal women, reducing the risk of osteoporosis, preventing cardiovascular disease, and anticancer effects (Chen, K. I., 2012, *Appl Microbiol Biotechnol* 96, 9-22). Specifically, isoflavonoids (nonsteroidal, phytoestrogenic, antioxidant compounds, ~1-5 μg/g dry soybean isolate) account for many of the above-mentioned health-enhancing properties. Numerous soybean protein products have been commercialized ranging from dietary supplements and infant formula, to animal husbandry products because of the soy's high nutritional content and the presence of many bioactive ingredients (Chen, K. I., 2012, *Appl Microbiol Biotechnol* 96, 9-22; Agostoni, C., et al., 2006, *J Pediatr Gastroenterol Nutr*, pp 352-361). Several biochemical and cellular studies have demonstrated beneficial systemic effects of soy protein—derived proteins/peptides such as, lunasin, which possesses anti-oxidative anti-inflammatory properties and anticancer activity, (Lule, V. K., et al. 2015, *J. Food Sci.*) Bowman-Birk, and glyceollin, which exhibit anti-carcinogenic properties, (Anta, L., et al., 2010, *J Chromatogr A* pp 7138-7143; Shin, S. H., 2013, *Exp Mol Med*, p e17) and Kunitz trypsin inhibitor, which blocks angiogenesis (Shakiba, Y., et al., 2007, *Fitoterapia* pp 587-589). Other bioactive soy protein constituents include an angiotensinl-converting enzyme inhibitory peptide with antihypertensive properties (Mallikarjun Gouda, et al., 2006, *J. Agric Food Chem* 54, 4568-4573) an adipogenesis inhibitor peptide with anti-obesity effect, Kim, H. J., et al., 2007, *Peptides*, pp 2098-2103) and anti-oxidant peptides with neuroprotective effects (Liu, P., et al., 2014, *Rejuvenation Res* 17, 209-211) Soy bean agglutinin (lectin) modulates monolayer formation in endothelial and epithelial cells, promoting wound healing (Gordon, S. R. 2011, *J Tissue Viability*, pp 20-29). More recently, the biological effects of soybean protein isolate (SPI) preparations that are soluble in strong acids or aggressive organic solvents containing protein/peptides as well as isoflavonoids and other bioactive compounds have been studied. SPI has been considered for skin wound healing, (Har-el, Y., et al., 2014, *Wound Medicine* 5, 9-15; Peles, Z., et al., 2013, *J Tissue Eng Regen Med* 7, 401-412; Santos, T. C., et al., 2013, *Tissue Eng Part A* 19, 860-869; Lin, L., et al., 2013, *Journal of Tissue Engineering and regenerative medicine* 7, 994-1008; Peles, Z., et al., 2012, *Acta Biomater* 8, 209-217; Ramji, K., et al., 2014, *J Biomater Appl* 29, 411-422; Santos, T. C., et al., 2010, *Tissue Eng Part A* 16, 2883-2890; Chien, K. B., et al., 2013, *Acta Biomater* 9, 8983-8990; Chien, K. B. et al., 2014, *J Biomater Appl* 28, 1085-1096; Shevchenko, R., et al., 2014, *Burns and Trauma* 2, 187-195) in the form of a paste, (Shevchenko, R., et al., 2014, *Burns and Trauma* 2, 187-195) hydrogels, (Chien, K. B. et al., 2014, *J Biomater Appl* 28, 1085-1096; Shevchenko, R., et al., 2014, *Burns and Trauma* 2, 187-195) films (Peles, Z. et al., 2013, *J Tissue Eng Regen Med* 7, 401-412) and electrospun fibrous membrane scaffolds (Har-el Y., et al., 2014, *Wound medicine* 5, 9-15; Lin, L., et al., 2013, *Journal of tissue engineering and regenerative medicine* 7, 994-1008). These formulations have been characterized as safe and fully degraded within two weeks, upon subcutaneous implantation in mice, with no signs of fibrosis or an allergic response to the soy-derived material (Chien, K. B., 2013, *Acta Biomater* 9, 8983-8990; Chien, K. B., et al., 2014, *J Biomater Appl* 28 1085-1096). In a rat-ring model of delayed wound-healing, it has been demonstrated that SPI scaffolds promote rapid re-epithelialization and wound closure, while studies in the pig have shown re-epithelialization and the regeneration of appendages, and neither has demonstrated overt immune-toxicity (Har-el, Y., et al., 2014, *Wound Medicine* 5, 9-15; Har-el, Y., et al., 2014, *Biomedical Engineering Society Annual Meeting*). In this context, the soy isoflavonoid genistein, one of the constituents of SPI, has been shown to enhance wound healing through multiple independent mechanisms (Park, E., et al., 2011, *Biochem Biophys Res Commun* 410, 514-519; Emmerson, E., et al., 2010, *Mol Cell Endocrinol*, pp 184-193). Furthermore, soymetide-4, an immune-modulatory soy-peptide fragment exhibits an anti-alopecia effect (prevents hair loss) (Tsuruki, T., et al., 2005, *Peptides,* 26, 707-711). Taken together, these results indicate that proteins, oligopeptides and/or phytoestrogens found in conventional soybean preparations, are promising as a "green" therapeutic platform for enhanced would healing. The present experiments were conducted to examine whether isolated protein components from WSsoy, a preparation that is devoid of phytoestrogens, will either individually or in combination, enhance wound healing and, specifically, re-epithelialization in diverse animal models. The data demonstrates that there are at least two different protein fractions in WSsoy, with distinct mechanisms of action: one (operationally termed Fraction 5) contains one or more pro-migratory, pro-proliferative and pro-angiogenic protein(s), which will affect skin cells in soluble form, while the other (Fraction 9) will promote migration, proliferation and angiogenesis in the solid phase (immobilized, e.g. in a scaffold) serving as a ligand for α9β1-expressing cells.

Example 2: Enhanced Re-Epithelialization and Angiogenesis are Based in Part on a Pro-Migratory Effect Induced by Soluble Proteins in the Absence of Isoflavonoids Many biological activities of commonly used SPI, including, possibly, wound healing, can be attributed to the presence of isoflavonoids (such as genistein), i.e., a sub-class of phytoestrogens that bind to estrogen receptors (ERs) and display weak estrogenic activity (McCarver, G., et al., 2011, *Birth Defects Res B Dev Reprod Toxicol* 92, 421-468; Thornton, M. J., 2013, *Dermatoendocrinol* pp 264-270). Therefore, it was first investigated whether water-soluble SPI (WSsoy, marketed as Clarisoy™ by ADM, Decatur, Illinois) preparations contain phytoestrogens, as do other soy-derived biomaterials (Hirsch, K., 2007, *Breast Cancer Res Treat* 104, 221-230). For this purpose electrospun SPI and WSsoy scaffolds were ethanol extracted and their phytoestrogenic activity was evaluated by comparison to genistein and estradiol E2 using a sensitive bioassay (McCarver, G., et al., 2011, *Birth Defects Res B Dev Reprod Toxicol* 92, 421-468).

Figure 1A:
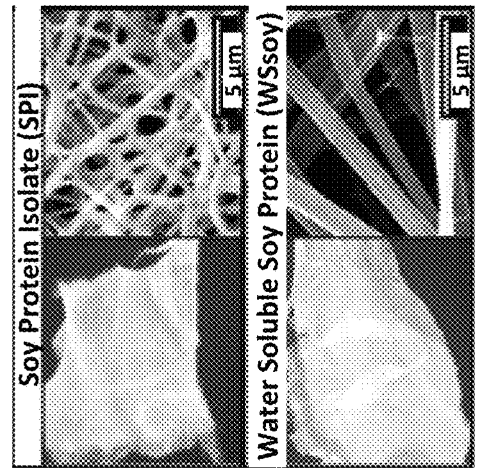
FIG. 1A, FIG. 1B and FIG. 1C depict the results of experiments demonstrating the identification of phytoestrogens in SPI, and to a lower level, in WSsoy powder and their respective electrospun fibers.
Figure 1B:
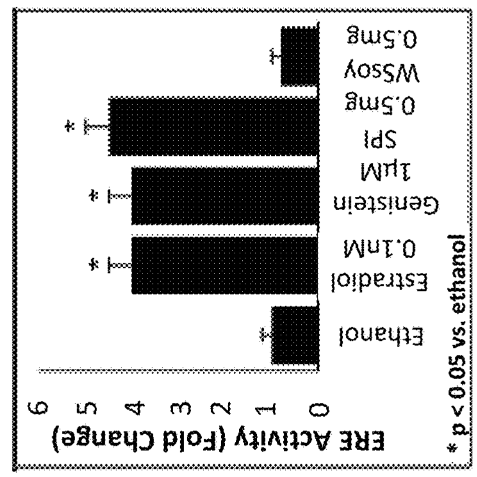
Figure 1C:
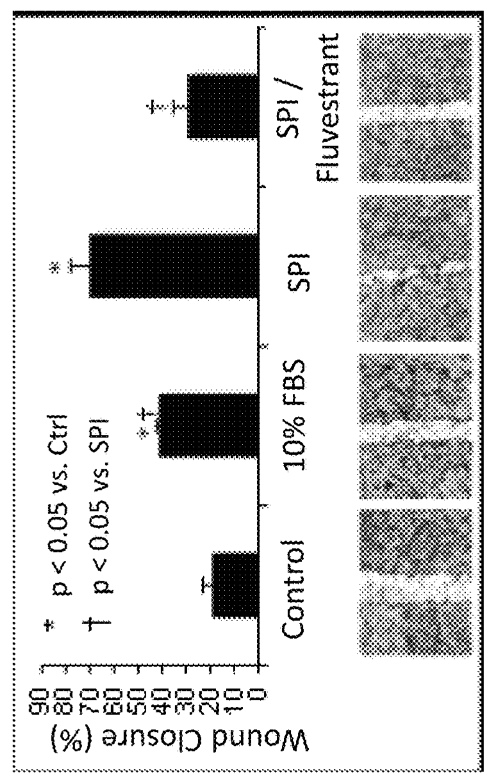

FIG. 1 indicates that extracts of electrospun soy fibrous membranes (0.5 mg SPI) induce an estrogen response element-dependent activity similar to genistein and estradiol, indicative of the presence of phytoestrogens in the SPI formulation. By contrast, the data also indicate that WSsoy powder and electrospun WSsoy matrices have reduced amount of phytoestrogens. Moreover, SPI-induced wound closure in HaCaT cells was significantly inhibited by the non-selective estrogen antagonist Fluvestrant, which did not affect WSsoy-induced wound closure. Furthermore, as demonstrated in FIG. 9-FIG. 11B, electrospun WSsoy matrices enhance wound healing, specifically re-epithelialization and angiogenesis in the absence of phytoestrogens.

Given these results, further studies are conducted isolate bioactive WSsoy proteins by reverse phase and ion exchange liquid chromatography. The extracted proteins are identified by proteomics, and their effects are characterized on cultured skin cells (i.e. keratinocytes, endothelial cells and fibroblasts) involved in wound healing. Considering that the wound healing activity of WSsoy may be due to distinct bioactive proteins/peptides, reverse phase-high pressure liquid chromatography (RP-HPLC) was used for the initial (1st step) preparative separation of WSsoy into several bioactive fractions (FIG. 2). This separation, performed using $C_{18}$ column with a linear gradient of elution (0-80% acetonitrile (ACN) over 45 min.), resulted in 11 protein fractions. Since cell migration in the wounded skin is a critical part of the re-epithelialization process (Li, J., et al. 2007, *Clin Dermatol* 25, 9-18) Fractions 3-11 with zeta potentials from +8 to +34 mV were tested in a wound healing assay in vitro (scratch assay) for the ability to stimulate migration of cultured skin cells, i.e. human dermal keratinocytes (HaCaT/primary keratinocytes), fibroblasts (HDFC) and microvascular endothelial cells (HDMVEC) (Lecht, S., et al., 2015, *Biochim Biophys Acta* 1850, 1169-1179). Fraction 5, similar to the total WSsoy extract, strongly stimulated the migration of all these cells in the scratch assay (FIG. 3). These findings indicate the presence in WSsoy of protein(s), which induce(s) pro-migratory activity of skin cells.

Figure 4:
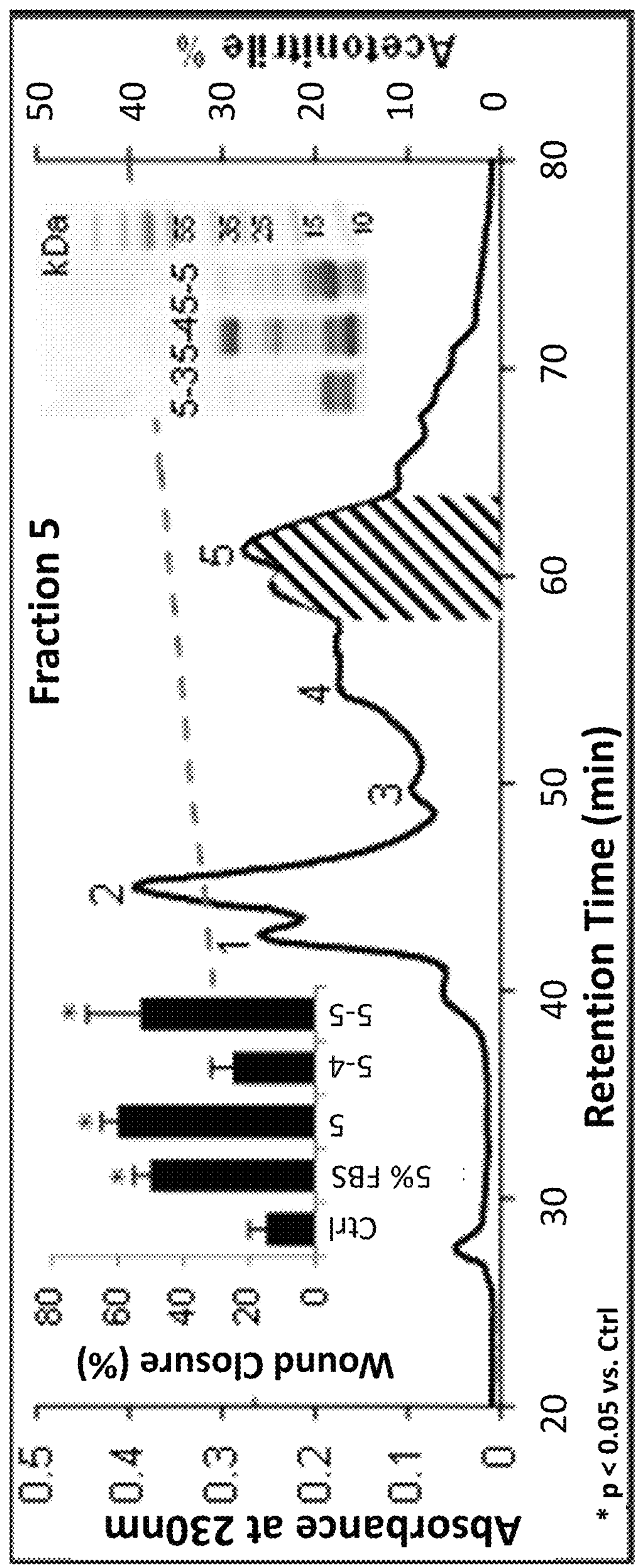
FIG. 4 is a graph depicting the re-chromatography of Fraction 5. Conditions were the same as in FIG. 2, except a "flatter" ACN gradient was used (30-80% over 120 min). Collected subfractions were named as 5-1 to 5-5. Shaded area indicates protein activity in HaCaT scratch assay (left inset). Right inset: SDS-PAGE gel stained with Coomassie Blue.

To further purify the pro-migratory protein(s), Fraction 5 was re-chromatographed on a RP-HPLC C18 column, using a "flatter" gradient of ACN (30-80% over 120 min.). Separation resulted in 5 new subfractions, termed 5-1 to 5-5 (FIG. 4). Maximal stimulation of keratinocyte migration was seen with Fraction 5-5 (FIG. 4, left inset). SDS-PAGE analysis under reduced conditions revealed that Fraction 5-5 still contains several protein bands (FIG. 4, right inset).

Additional purification is performed to identify and purify the pro-migratory bioactive component(s) from Bioactive Component Fraction 5-5 (BCF5-5) and to purify them to homogeneity.

Experiments are conducted to purify and characterize Fraction 5-5 by ion exchange chromatography. Fraction 5-5 components are purified to homogeneity by ion-exchange chromatography using FPLC with MonoQ HR 5/5 and MonoS HR 5/5 columns, a method successfully applied for isolation of soybean protein (Amigo-Benavent, M., et al., 2010, *J Chromatogr B Analyt Technol Biomed Life Sci*, pp 2453-2456).

The in vitro effects of purified components of Fraction 5-5 on the migration/proliferation of various cultured skin cells are investigated. Pro-migratory activity of the purified proteins are evaluated by an established wound scratch assay in 24 well plates (Lecht, S., et al., 2015, *Biochim Biophys Acta* 1850, 1169-1179). In brief, fully confluent cell layers are serum starved overnight and then scratched to generate artificial wounds in the monolayers. Cell migration is stimulated by 2% FBS (HMVDEC), 5% FBS (HaCaT or primary keratinocytes) and 10% FBS (HDFC) in the culture medium (positive controls) or by medium with 0.1% FBS in the absence (negative control) or presence of 1-100 μg/mL of purified BCF5-5 to generate a dose response. The plates are incubated at 37° C. in 5% $CO_2$ atmosphere for 24 hr. The extent of "wound closure" is visualized and calculated, as described (Lecht, S., et al., 2015, *Biochim Biophys Acta* 1850, 1169-1179). Proliferation activity in vitro is tested by measuring BrdU incorporation, (Ventresca, E. M., et al., 2015, *Cell Signal* 27, 1225-1236) into skin cells following stimulation with BCF5-5. The results of the BrdU assay are confirmed by cell counting and AlamarBlue assays. Measurement is performed at 24, 48, and 72 hr.

Further, the effects of purified components of Fraction 5-5 on angiogenesis are investigated in vitro (Matrigel assay) and in the quail chorioallantoic membrane (CAM) in vivo. Pro-angiogenic activity in vitro is analyzed by a tube formation assay using Matrigel with reduced growth factors (Walsh, E. M., et al., 2012, *Neuro Oncol*, pp 890-901). HDMVEC are cultured on Matrigel and treated with soluble BCF5-5. Pro-angiogenic activity in vivo is analyzed using embryonic quail CAM assay, as described (Walsh, E. M., et al., 2012, *Neuro Oncol*, pp 890-901). Embryos are treated with BCF5-5 and analysis of the angiogenic index is performed as described (Lazarovici, P., et al., 2006, *Endothe-*

*lium* 13, 51-59). The dose of BCF5-5 is determined by the in vitro dose response results. As additional negative control, the effects of the non-active Fraction 5-4 are investigated.

The primary sequence of the bioactive components of Fraction 5-5 is identified by MALDI-TOF. Amino acid sequence alignments with known high and low abundance proteins annotated on the NIH PDB protein data bank and a soy protein data base (Tavakolan, M., et al., 2014 Bioinformation pp 599-601) are performed using the BLASTp tool.

Further, the cellular receptor(s) and cell signaling pathways induced by bioactive components of Fraction 5-5 component(s) are identified in cultured skin cells.

Figure 5:
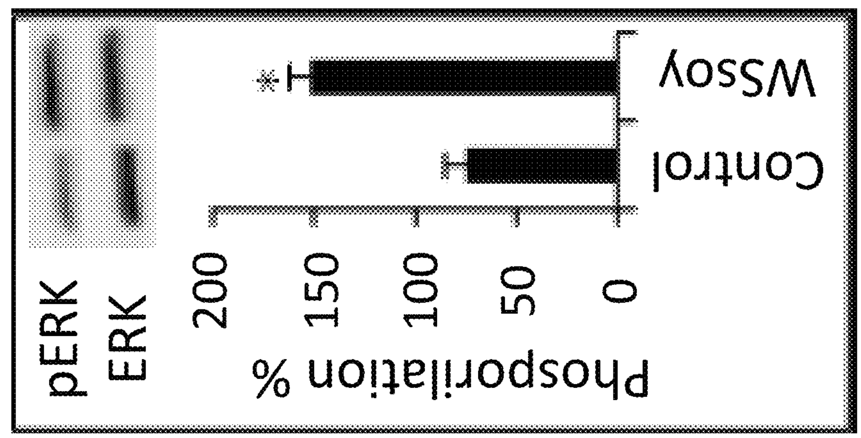
FIG. 5 depicts the results of experiments demonstrating WSsoy stimulation of ERK phosphorylation activity in HaCaT cells. Cells were stimulated with 50 m/ml WSsoy. Cell lysates were electrophoresed and transferred to paper and immunoblotted with phospho-ERK followed by pan-ERK antibodies. Top: phosphorylated bands. Bottom: phosphorylation ratio % between pERK/ERK.

Activated protein profiling is studied using by PhosphoScan. Based on reports that soy proteins induce phosphorylation of ERK-mTOR-S6 kinase (Lee, J., et al., 2012, *J Nutr Biochem* 23, 1341-1351), JAK2 and AMPK (Jang, E. H., et al., 2008, *Int J. Obes* (*Lond*) 32, 1161-1170) in different cell types as well as findings presented herein of ERK1,2 phosphorylation induced by WSsoy (FIG. 5), the effect of purified BCF5-5 on skin cell phosphorylation is investigated. The different cell types are treated with 50 m/ml of BCF5-5 (a concentration that enhances cell migration). Peptides obtained by trypsin digestion are purified by HPLC (Seppak C18 column), as described (Gu, T. L., et al., 2011, *PLoS One* 6, e15640). Phosphorylated proteins are isolated by immunoprecipitation with a monoclonal anti-phosphotyrosine antibody (pY100), concentrated on reverse-phase micro tips and analyzed by liquid chromatography tandem mass spectrometry (LC/MS-MS) (Gu, T. L., et al., 2012, *PLoS One* 6, e15640). To isolate and characterize a putative membrane receptor that stimulates cell migration/proliferation and/or angiogenesis, purified BCF5-5 conjugated with a highly photo-reactive azido group is first prepared, followed by biotinylation (Kurose, T., et al., 1994, *J Biol Chem* 269, 29190-29197). To identify the receptor the probe is photo-crosslinked to skin cells to generate a photo-affinity labeled ligand-receptor complex. This product is digested with endopeptidases and the resulting cross-linked peptide fragments are separated by streptavidin-affinity chromatography and analyzed using LC-LTQ ion trap mass spectrometer)/ (Lupe-Garcia. J. L., 2010, *Proteoinics* 10, 940-952).

The studies presented herein result in the purification and primary sequence identification of one or more pro-migratory protein(s) in Fraction 5-5 and the characterization of its/their effective dose to induce migration of skin cells in vitro. According to the soy protein data base, soy preparations contain two major storage proteins: β-conglycinin (βCG) and glycinin accounting for 80% of total proteins and more than 100 lower abundance proteins (Tavakolan, M., et al., 2014, *Bioinformation*, pp 599-601). The pro-migratory protein(s) in BCF5-5 are either one of the abundant (whole protein, subunit or derived peptide fragment) or a minor protein/peptide that can be identified with the aid of proteomic mass spectrum data followed by bioinformatics-based data mining.

In case the two steps of ion exchange chromatography do not provide a homogeneous bioactive protein suitable for proteomic sequencing, other chromatographic alternatives for purification, such as DEAE-Toyopearl anion exchange column chromatography (Zhang, G. Y., 2002, *Phytochemistry*, pp 675-681) and size exclusion chromatography using Sephadex G-100 (Bhushan, R., et al., 2007, *Biomed Chromatogr* 21, 1245-1251) may be used, both of which have been successfully used for purification of soybean proteins such as glycinin and conglycinin (Amigo-Benacent, M., et al., 2010, *J. Chromatogr B Analyt Technol Biomed Life Sci* pp 2453-2456). In case the isolated protein is a glycoprotein, deglycosylation of the soybean pro-migratory protein is performed, as described (Fu, C., et al., 2007, *J Agric Food Chem* 55 4014-4020), using an enzymatic N-deglycosylation kit (GlycoProfile II, Sigma) in accordance with the manufacturer's instructions and the efficiency of the deglycosylation is verified by a shift in mobility of the protein on a SDS-PAGE gel. The deglycosylated protein(s) is tested for pro-migratory activity to assess the contribution of glycosylation to the biological effects. In case the active compound is an oligopeptide (<30 amino acids), validation is performed by solid phase synthesis. An alternative to the in vivo CAM angiogenesis assay in quails, pro-angiogenic activity of BCF5-5 is measured in the corneal micropocket assay in rats (Momic, T, et al., 2014, *J Pharmocol Exp Ther* 350, 506-519). In an alternative to identifying phosphoproteins as described above, a global kinomics approach is used. The extracts of skin cells treated with bioactive soy proteins are analyzed by commercial human phosphorylated peptides microarrays (Kindrachuk, J., et al., 2012, *Mol Cell Proteomics* 11, M111.015701. Signaling pathways are analyzed based on the activated kinases in the samples using bioinformatics approaches (Lecht, S., et al., 2014, *Stem Cells Dev* 23, 1923-1936). In case of difficulties characterizing the pro-migratory protein receptor as described above, mass spectrometry coupled with in situ chemical crosslinking (Pertl-Obermeyer, H., et al., 2014, *J Proteomics* 10817-29) and immunoaffinity purification (Kim, K. M., et al., 2012, *Methods*, pp 161-165), is used for identifying the cellular receptor of BCF5-5. For this, rabbit polyclonal or mouse monoclonal antibodies are generated against the purified BCF5-5.

Figure 6:
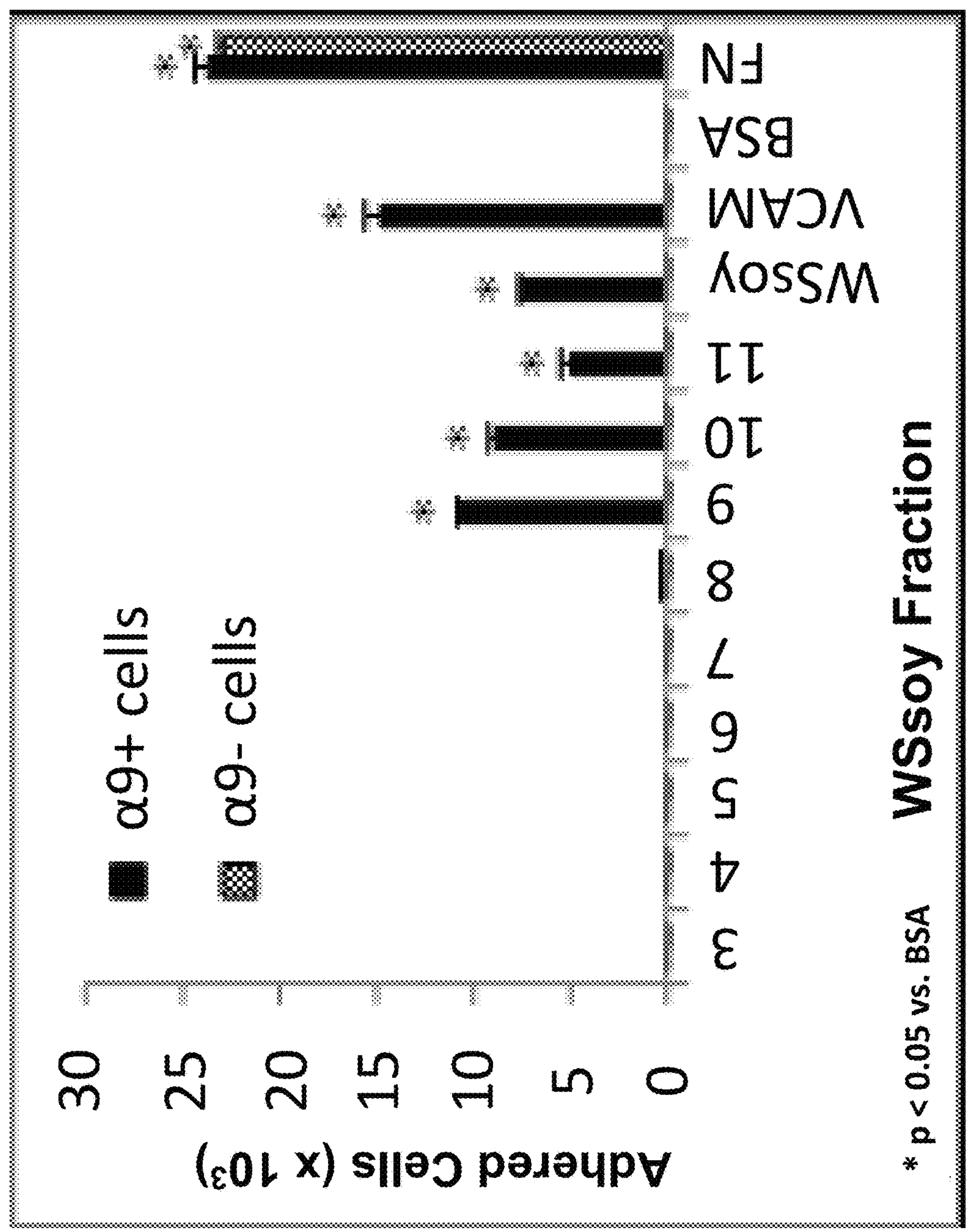
FIG. 6 is a graph demonstrating the results of experiments investigating the adhesion of cells transfected or not with α9 integrin subunit to immobilized WSsoy fractions (50 μg/mL) obtained after 1st RP-HPLC (see FIG. 2). Adhesion was performed and analyzed as described (Brown et al., 2008, Neuro Oncol, 10: 968-980). WSsoy: immobilized water-soluble soy. Vascular Cell Adhesion Molecule-1 (VCAM-1, a natural ligand for α9β1 integrin): positive control. Fibronectin (FN): positive control for both cell types. Bovine serum albumin (BSA): negative control. Error bars represent duplicate experiments (*) $p<0.001$ if compared to binding to BSA.

Example 3: Enhanced Re-Epithelialization and Angiogenesis is Mediated by Distinct WSsoy Protein(s) and their Derivatives, which are Ligands for α9β1 Integrin In the described studies, the 11 WSsoy fractions obtained by RP-HPLC separation (see FIG. 2) were immobilized and their ability to promote adhesion of cells that did or did not express α9β1 integrin was tested using cells that have been transfected with the α9 integrin subunit (α9+) (Ventresca, E. M., et al., 2015, *Cell Signal* 27, 1225-1236; Brown, M. C., et al., 2008, *Neuro Oncol* 10, 968-980). Screening of these fractions revealed adhesion of α9+ cells to immobilized Fractions 9, 10 and 11 (FIG. 6). No adhesion was observed for wild type cells (α9−), which do not express α9β1 integrin. Importantly, these adhesion experiments were performed in the absence of any stimulatory factors for integrin (activating monoclonal antibodies or high concentrations of manganese cations). The most efficient adhesion was observed for Fraction 9, and this fraction was selected for further investigation.

Figures 7A, 7B:
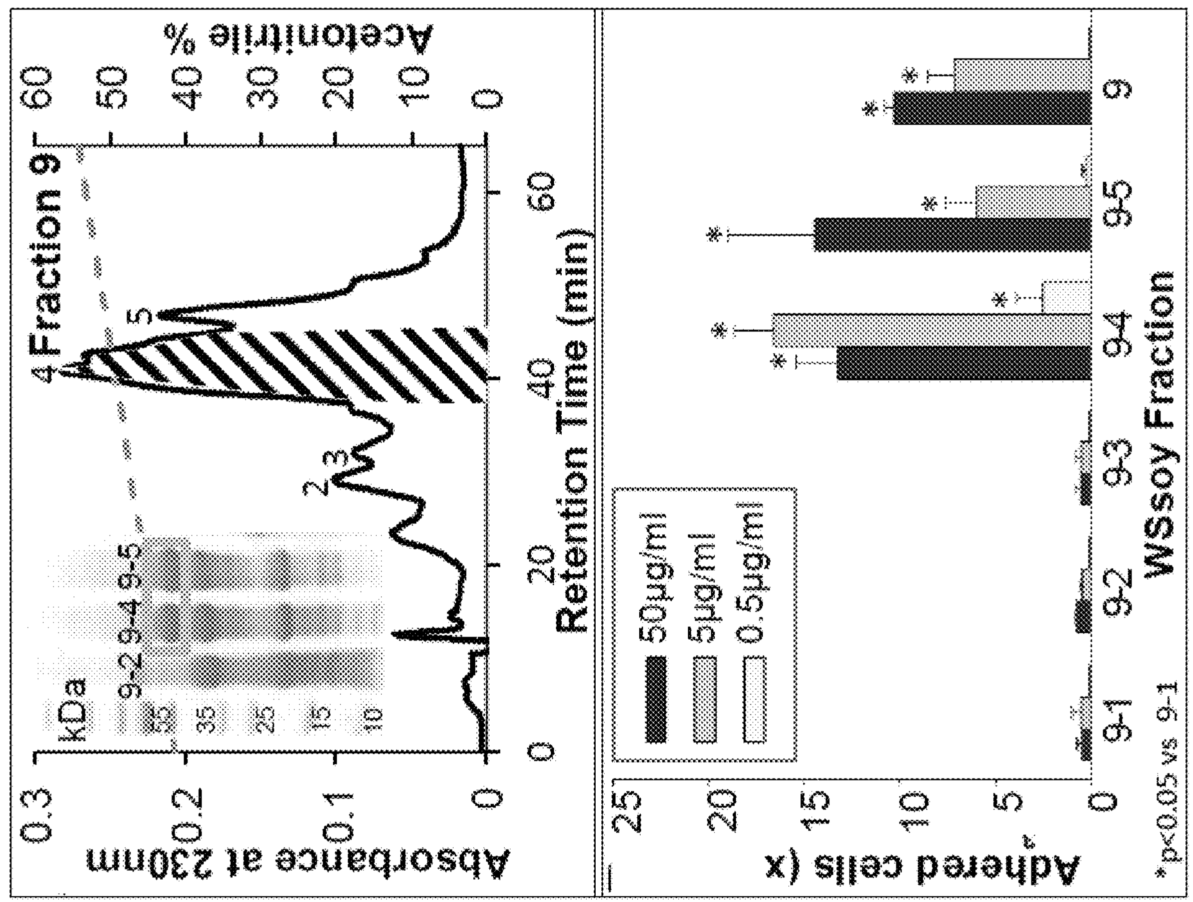
FIG. 7A and FIG. 7B, depicts the results of experiments performed for the characterization of Fraction 9 obtained after 1st RP-HPLC.

In order to identify the active protein(s) in Fraction 9, which is a ligand for α9β1 integrin, this fraction was re-chromatographed on RP-HPLC using a "flatter" gradient of acetonitrile (40-80% over 120 min.), which resulted in five subfractions (FIG. 7A). Pro-adhesive activity at the lowest concentration tested (0.5 m/mL) was mainly found in Fraction 9-4 (FIG. 7B). SDS-PAGE analysis of the subfractions showed a high degree of heterogeneity under non-reducing conditions (FIG. 7B, inset). Comparison of the presence of particular bands in active Fraction 9-4 and non-active Fraction 9-2, revealed possible candidates for α9β1 integrin-binding, most prominently a protein with an apparent MW of 55 kDa. This band was excised and analyzed by mass spectrometry (proteomics) by sequencing trypsin-generated peptides. All identified peptide sequences in this band (55 kDa) correspond as expected to sequences of fragments of the alpha prime chain of beta-conglycinin (βCG).

Further, the selectivity of the interaction of protein(s) in Fraction 9-4 with α9β1 integrin expressing cells was tested in competition experiments with VLO5. VLO5 is a snake venom MLD-disintegrin, which potently binds to α9β1 integrin (Bazan-Socha, S., et al., 2004, *Biochemistry* 43, 1639-1647), VLO5 inhibited adhesion of α9+ cells to immobilized Fraction 9-4 (IC50=5.6 nM) with similar potency as to immobilized VCAM-1 (IC50=3.2 nM), showing a comparable affinity of α9β1 binding to both these ligands. Importantly, addition of soluble Fraction 9-4 (up to 100 μg/ml) did not inhibit α9+ cell adhesion to other immobilized α9β1 integrin ligands, including VCAM-1, VLO5 and NGF. It is thus concluded that proteins in Fraction 9-4 bind α9β1 integrin only in the solid phase, which is characteristic for a majority of ECM proteins. This observation may explain the observed efficacy of electrospun WSsoy matrices enhancing therapeutic wound healing in rats (FIG. 10).

Figure 8B:
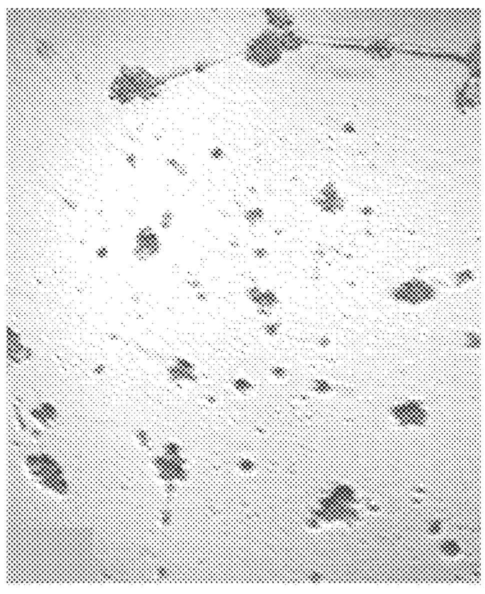
FIG. 8A and FIG. 8B, depicts the results of experiments investigating HDMVEC tube formation in Matrigel in the presence (FIG. 8A) or absence (FIG. 8B) of Fraction 9-4. Matrigel was co-polymerized with Fraction 9-4 (30 microgr/50 μL) and cells ($1\times10^4$ per 150 μL of serum and growth factor-free EGM-2 media) were applied. Images were taken after 24 hours incubation at 37° C.
Figure 8A:
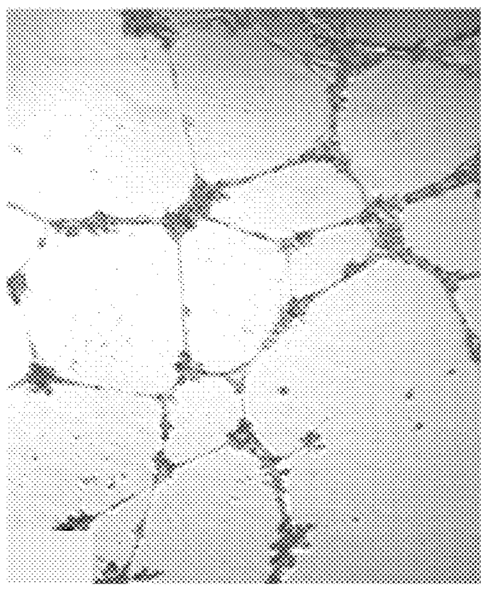
Figure 9:
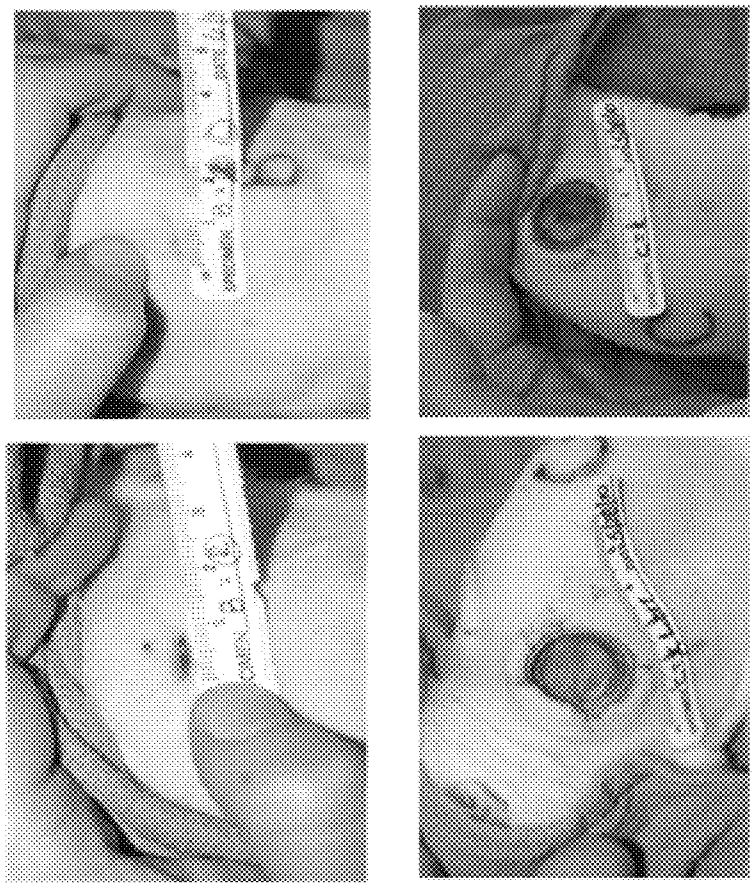
FIG. 9 depicts results of experiments using the ring model of delayed wound healing in rats. Left and right panels: wounds left untreated and covered with Tegaderm (Control) & electrospun soy sound matrix and then covered with Tegaderm. Top panels: wound healing in "normal" rats at day 18—note accelerated healing with electrospun soy scaffolds (right top). Bottom panels: delayed wound healing in the rat-ring model: The Tegaderm-covered wound appears essentially non-healing, while the soy scaffold treated wound appears covered with a scab, but is re-epithelialized underneath.

To assess the effects of Fraction 9-4 on angiogenesis in vitro, the Matrigel tube formation assay was used as described (Walsh, E. M., et al., 2012, *Neuro Oncol*, pp 890-901). Given the fact that the proteins of Fraction 9-4 were only active in immobilized form, Fraction 9-4 was co-polymerized with growth factor reduced Matrigel. As expected, HDMVEC did not form tubular structures on the growth factor depleted Matrigel, however robust capillary-like network formation as observed when Fraction 9-4 proteins were added to the Matrigel prior to polymerization (FIG. 8).

Experiments are performed to purify and characterize Fraction 9-4 by ion exchange chromatography. For the purification of α9β1 integrin-binding proteins, Fraction 9-4 is purified to homogeneity by applying different purification strategies, e.g. differential pH precipitation (Lakemond, C. M., et al., 2000, *J. Agric Food Chem* 48, 1985-1990) and ion-exchange chromatography, described elsewhere herein. Each step is monitored by testing the pro-adhesive activity of the fractions to α9+ cells.

Experiments are also performed to investigate the in vitro effects of purified Fraction 9-4 components on the migration/proliferation of various cultured skin cells. Further the effects of the purified Fraction 9-4 components on angiogenesis in vitro (Matrigel assay) and in the quail CAM in vivo are also examined. Cellular responses of purified proteins are studied using cultured skin cells. Specifically, migration, proliferation, and angiogenesis assays are performed as described elsewhere herein, using immobilized proteins from Fraction 9-4. The specificity of the interaction of the bioactive components Fraction 9-4 (BCF9-4) with α9β1 integrin are verified using a specific inhibitor of this integrin, VLO5 (Walsh, E. M., et al., 2012, *Neuro Oncol*, pp 890-901).

Experiments are also conducted to identify the primary sequence of the bioactive protein(s) in Fraction 9-4 by MALDI-TOF. Amino acid sequence alignments with known high and low abundance proteins are performed as discussed elsewhere herein.

Experiments are also performed to identify cellular signaling by which bioactive component(s) of Fraction 9-4 activate α9β1 integrin. Cell signaling experiments are performed to identify cytoplasmic signaling molecules, which are activated following attachment of cells to BCF9-4. First, experiments are performed with a focus on tyrosine kinases, where the phosphorylation of their cognate substrates are compared following skin cell spreading/attachment on BCF9-4 using Western blot with anti-tyrosine antibody, as described (Jiang, H., et al., 1997, *J Cell Biochem* 66, 229-244). Further, the substrates for tyrosine phosphorylation are identified by proteomic approaches. Separation of cellular lysates by Western blot is processed using a 2-D gel. Protein spots showing increased intensity are excised from the gel and sent for proteomic analysis. Other key pathways studied include MAP kinases, AKT and FAK, which are involved α9β1 integrin-mediated cell migration/proliferation. Recently, it was described that these pathways are activated by α9β1 integrin (Ventresca, E. M., et al., 2015, *Cell Signal* 27, 1225-1236).

The presently described studies demonstrate that purification of Fraction 9-4 yield an active compound interacting with α9β1 integrin in an immobilized form and stimulate migration/proliferation in the proposed skin cell lines Moreover, the experiments confirm the pro-angiogenic effect of BCF9-4 in vitro, when co-polymerized at different concentrations with growth factor reduced Matrigel. Inhibiting interactions of BCF9-4 with α9β1 integrin by the MLD-disintegrin, VLO5, block cell migration and proliferation, as well as tube formation in Matrigel. Further, BCF9-4 results in the activation of kinases such as ERK or focal adhesion kinases (FAK), which are activated following interactions of ligands with a majority of integrins. If indeed these or other kinases are activated, established biochemical assays are performed using specific inhibitors to ascertain their involvement in BCF9-4 dependent migration/proliferation and angiogenesis.

Comparative analysis of the BCF 9-4 with inactive Fraction 9-2 (FIG. 7A and FIG. 7B) is performed by 2-D electrophoresis to identify unique spots that may represent potential active protein(s). The proteins in these spots are identified by proteomics. The major proteins from this evaluation are screened for binding to α9β1 integrin in cell adhesion assays. In an alternative to identifying phosphoproteins as described above, a global kinomics approach, as described elsewhere herein, is used.

Figures 10A, 10B, 10C, 10D:
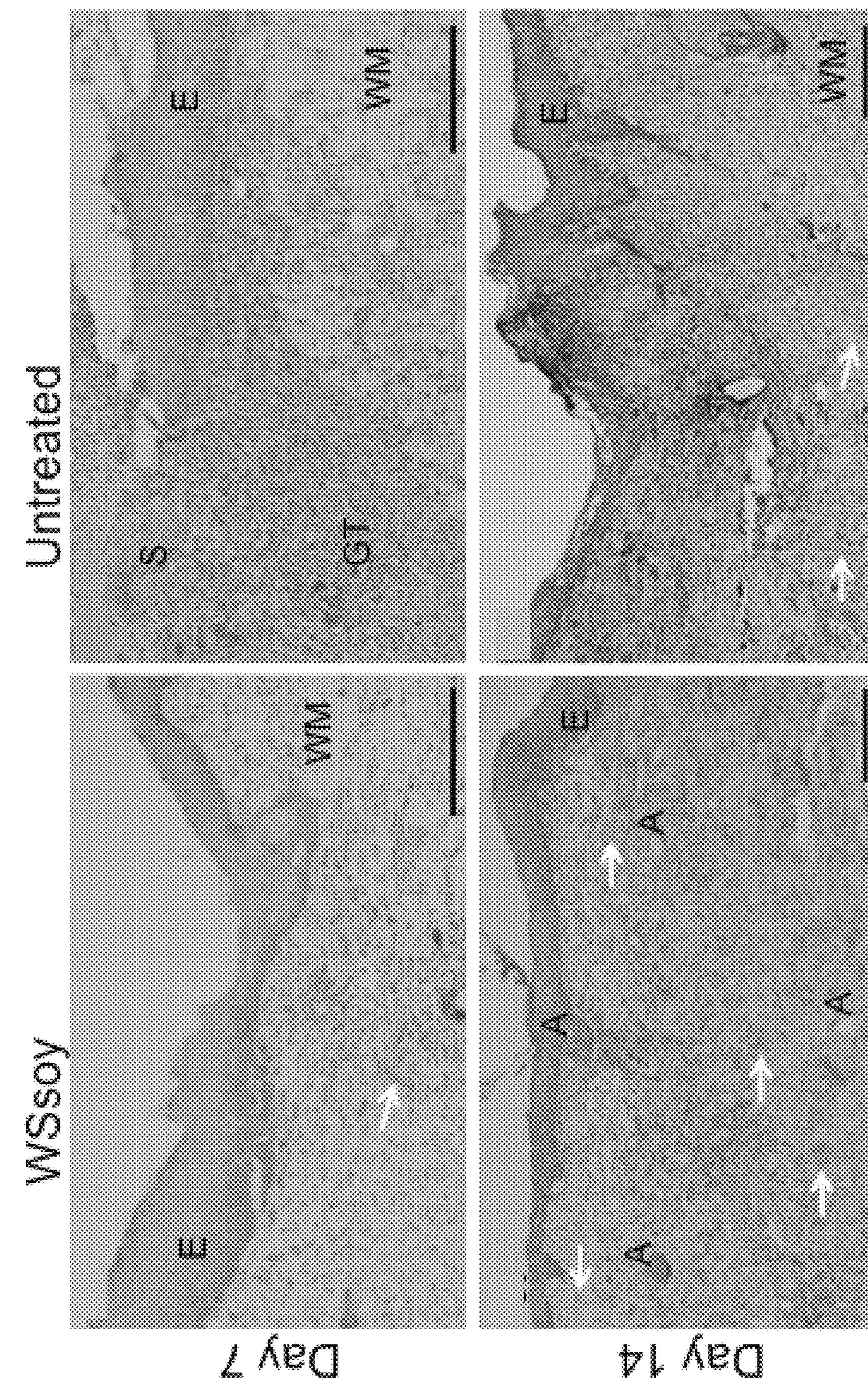
FIG. 10A-FIG. 10D, depicts the results of Hematoxylin and Eosin staining of control and WSsoy treated full thickness cutaneous wounds.
Figures 11A, 11B:
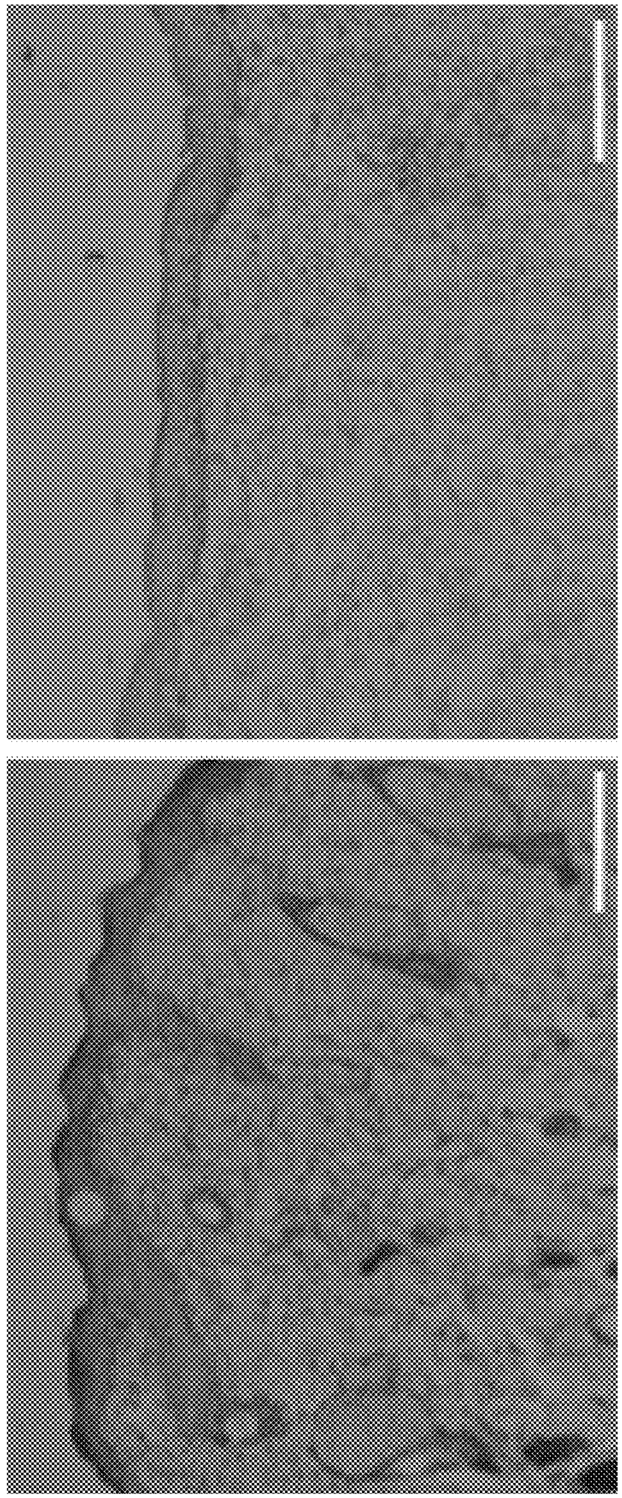
FIG. 11A and FIG. 11B, depicts the results of panCytokeratin staining of full thickness cutaneous wounds treated with WSsoy scaffolds (FIG. 11A) or left untreated and covered with Tegaderm only, (FIG. 11B). For details see text. Scale bars represent 200 μm.

Example 4: Effects of Bioactive Components of WSsoy Re-Epithelialization and Angiogenesis in Full Thickness Cutaneous Wounds in Rat and Pig Models In previous studies, the HFP-soluble form of SPI was used, which contains isoflavonoids and demonstrated enhanced re-epithelialization and vascularization in rat and pig models of full thickness cutaneous wounds (Har-el, Y., et al., 2014, *Wound Medicine,* 5, 9-15; Har-el Y., et al., 2014, *Biomedical Engineering Society Annual Meeting*; Lin, L., 2011, PhD thesis, Drexel University, *Biomedical Engineering* p 207). Specifically, for the rat studies a model for delayed healing (Galiano, R. D., et al., 2004, *Wound Repair Regen* 12, 485-492), was adapted (FIG. 9), in which wound closure by contraction is avoided by securing the skin around the edges of the wound with a silicone ring. Focusing on water-soluble soy protein instead of conventional SPI, this "rat-ring model" in the presently described studies. As seen in FIG. 10A through FIG. 10D, at day 7 post wounding (pw), wounds covered with WSSoy exhibit complete epithelial coverage (FIG. 10A), whereas control wounds covered with Tegaderm lack the epidermis, while the dermis in the center of the wound is essentially granulation tissue lacking any organization (FIG. 10B). By day 14 pw, the control, the Tegaderm-covered wounds, exhibit some level of epithelialization while the epidermis is replete with granulation tissue (FIG. 10D). By contrast, and in line with previously published results in the wounds covered with the WSsoy scaffold the organization of the dermis is more pronounced and shows the beginning of regeneration of appendages (FIG. 10C). Immunohistochemical studies (FIG. 11A and FIG. 11B) reveal a more mature epithelium (robust staining of the epidermis with pan-cytokeratin) in the WSSoy treated wounds, whereas the control wounds show little or no staining. Importantly, while appendage re-generation was observed by day 14 in all WSsoy treated animals (n=4) studied so far, the extent was more robust in some of them and seen even in the center of the wounds.

Following purification of specific bioactive protein fractions, the effectiveness of each of these fractions are tested on wound healing in vivo using a previously established model of delayed rat wound healing (Galiano, R. D., et al., 2004, *Wound Repair Regen* 12, 485-492). Moreover, the findings are further validated in a pig study (see below).

Specifically BCF5-5 is prepared in delivery vehicles/formulations that will quickly provide these proteins in soluble form at the site of the wound. Potential formulations include preparing the fraction as a powder, admixed with a hydrogel that has no bioactivity, such as gelatin which is crosslinked with genipin (Saglam A., et al., 2013, *J Mol Neurosci* 49, 334-346) or encapsulated in microspheres incorporated in an electrospun scaffold (Zabrodin, I., 2009, MS thesis, Drexel University, *Biomedical Engineering* p 104). By contrast, BCF9-4 is prepared in an immobilized form, e.g., as an electrospun scaffold or admixed with a biologically inactive polymer as an electrospun scaffold. These delivery systems are first tested and optimized in a rat model of delayed wound healing (Har-el Y. et al., 2014, *Biomedical Engineering Society Annual Meeting*; Galiano, R. D., et al., 2004, *Wound Repair Regen* 12, 485-492 and then validated in a pig model of wound healing (Har-el Y., et al., 2014, *Wound Medicine* 5, 9-15).

Experiments are performed to prepare a system to deliver soluble BCF5-5 for treatment of wounds in vivo and to determine the optimal delivery system in a rat model of delayed wound healing. Experiments are also performed to prepare a system to deliver immobilized BCF9-4 for treatment of wounds in vivo and to determine the optimal delivery system in a rat model of delayed wound healing. Further, the optimal delivery systems for both BCF5-5 and BCF9-4 are validated in a pig model of wound healing.

The rat studies are time course studies to determine how well BCF5-5 and BCF9-4 enhance re-epithelialization of the skin over time. Early and late time points are investigated to analyze histologically how these fractions enhance re-epithelialization and vascularization compared to both positive and negative controls. The rat ring model of delayed wound healing is based on published methods (Galiano, R. D., et al., 2014, *Wound Repair Regen* 12, 485-492; Har-el Y. et al., 2014, *Biomedical Engineering Society Annual Meeting*). The experiments are terminated at predetermined time-points (see below). After euthanasia, the wounded/healing skin and surrounding healthy tissue is collected and processed for routine histology and frozen sections, as described (Har-el Y., et al., 2015, *Wound Medicine* 5, 9-15). Thin paraffin embedded sections (5 μm) are stained with Hematoxylin & Eosin, and Masson's Trichrome and Picro-sirius Red (ECM recovery, specifically collagen). Immunohistochemistry (IHC) is performed on the sections to determine the extent of inflammation/immune response, vascularization and re-epithelialization. All these staining techniques are well established are performed using published protocols (Mondrinos, M. J., et al. 2006, *Tissue Eng* 12, 717-728; Mondrinos, M. J., et al., 2007, *Am J Physiol Lung Cell Mol Physiol* 293 L639-650; Mondrinos, M. J., et al., 2008 *Tissue Eng Part A* 14, 361-368). Further, tissue sections are also stained for macrophages, using iNOS and CD206, two established markers for M1 and M2a macrophages, as heralds of inflammation and tissue repair, respectively (Novak, M. L., et al., 2013, *J Leukoc Biol* 93, 875-881). Endothelial cells are stained with anti-CD31 antibodies, while pan-cytokeratin and cytokeratin 15 antibodies are used to stain for epithelial cells. This staining reveals the extent that the skin was able to repair itself by revascularization and epithelialization and how quickly this repair progresses in each treatment group. In all cases, isotype-match pre-immune antibodies from the same species as the primary antibody are used as negative controls. For multiplex staining secondary antibodies labeled with different fluorophores are used, as described (Mondrinos, M. J., et al., 2006, *Tissue Eng* 12, 717-728; Mondrinos, M. J., et al., 2007, *Am J Physiol Lung Cell Mol Physiol* 293 L639-650; Mondrinos, M. J., et al., 2008, *Tissue Eng Part A* 14, 361-368).

The tested delivery system for the BCF5-5 consists of 3 options A. Delivery of BCF5-5 powder sprinkled on the wound. B. Hydrogels made with a non-bioactive natural polymer such as gelatin, admixed with BCF5-5. Gelatin hydrogels are stable at 37° C. when crosslinked with genipin (Seglam, A., et al., 2013, *J Mol Neurosci* 49, 334-346). This method allows for the alteration of the concentration of genipin used to achieve a hydrogel whose stiffness is close to that of natural skin. C. BCF5-5 in microcapsules and incorporated electrospun scaffolds using a previously described technique (Zabrodin, I., 2009, MS thesis, Drexel University, *Biomedical Engineering*, p 104). The scaffolds are made from a polymer that is biocompatible, but has no known bioactivity such as a blend of PLGA/Gelatin/Elastin (PGE) (Han, J. et al., 2011, *Biomacromolecules* 12, 399-408). The microspheres are made from PLGA (Zabrodin, I., 2009, MS thesis, Drexel University, *Biomedical Engineering*, p 104; Har-el Y, 2005, PhD thesis, Johns Hopkins University, *Chemical and Biomolecular Engineering* p 199), or from alginate (Zabrodin, I., 2009, MS thesis, Drexel University, *Biomedical Engineering*, p 104) depending on which method yields better release of BCF5-5. Prior to the start of in vivo studies, tests of loading efficiency and in vitro release studies are performed to determine the extent of release of BCF5-5 from each of the microsphere formulations, as described (Zabrodin, I., 2009, MS thesis, Drexel University, *Biomedical Engineering*, p 104; Har-el Y., et al., 2005, PhD thesis, Johns Hopkins University, *Chemical and Biomolecular Engineering* p 199). It is estimated that the first two purification steps of WSsoy (to reach Fractions 5-5 and 9-4) have enriched the protein by at least 50-fold. Further purification can enrich the active protein to a total ~100-fold. Therefore, to deliver equivalent doses of BCF5-5 and BCF9-4 a dose of 100 μg is needed in the rats, or 1% of the original WSsoy. For each system, WSsoy acts as a positive control and an untreated wound serves as a negative control.

Comparison of wound healing ability of soluble BCF5-5 delivered as a powder (40 rats): Two of four treatments described below are administered to each rat in a random manner (no rat receives two of the same treatment). The treatments are: A. BCF5-5 powder (100 μg) admixed with methylcellulose (Bonadio, W. A., et al., 1992, *Ann Emerg Med* 21, 1435-1438) (10 mg). B. Whole WSsoy powder (10 mg, positive control) C. Methylcellulose alone (10 mg) D.

Untreated. Total 10 rats per time point (20 wounds). Time points to be examined: days 3, 7, 14, and 28.

Comparison of wound healing ability of soluble BCF5-5 delivered as a hydrogel (25 rats): Two treatments described below are administered to each rat. The treatments are: A. BCF5-5/crosslinked gelatin hydrogel (100 ug of BCF5-5) B. Untreated. Total 5 rats per time point (10 wounds). Time points to be examined: days 3, 7, 14, and 28.

Comparison of wound healing ability of soluble BCF5-5 delivered from microspheres (28 rats): Two of three treatments described below are administered to each rat in a random manner (no rat receives two of the same treatment). The treatments are: A. BCF5-5 in microspheres incorporated in a PGE electrospun scaffold B. Blank microspheres incorporated in a PGE electrospun scaffold (negative control) C. Untreated. Total 7 rats per time point (14 wounds, 5 wounds of A and B, and 4 of Controls). Time points to be examined: days 3, 7, 14, and 28.

BCF9-4 is prepared in an immobilized form as an electrospun scaffold matrix. Electrospun WSsoy acts as a positive control and Fraction 4 (which has not shown bioactivity in any studies to date) serves as a negative control. Concentrations of BCF9-4 that are used are calculated based dose response in cell studies. The experiments are carried out and analyzed following the same protocols described above.

Comparison of wound healing ability in the delivery of immobilized BCF9-4 as an electrospun scaffold (28 rats): Two of three treatments described below are administered to each rat in a random manner (no rat receives two of the same treatment). The treatments are: A. BCF9-4 as an electrospun scaffold B. Whole WSsoy as an electrospun scaffold C. Untreated. Total 7 rats per time point (14 wounds, 5 wounds of A and B, and 4 of Controls). Time points to be examined: days 3, 7, 14, and 28.

Determination of possible additive or synergistic effect of combining BCF5-5 and BCF9-4 in one treatment (60 rats): Two of six treatments are administered to each rat in a random manner (no rat receives two of the same treatments). The treatments are: A. BCF5-5 microspheres incorporated in an electrospun BCF9-4 scaffold (for synergistic effect). B. Optimal formulation of BCF9-4 (positive control for BCF9-4). C. Optimal formulation of BCF5-5 (positive control for BCF5-5). D. BCF5-5 in microspheres incorporated in a PGE electrospun scaffold. E. Whole WSsoy as an electrospun scaffold (overall positive control). F. Untreated. Total 15 rats per time point (30 wounds) so that there are 5 wounds from each of these treatments. Time points to be examined: days 3, 7, 14, and 28.

Pig studies are carried out similar to what was previously described (Har-el Y., et al., 2014, *Wound Medicine* 5, 9-15). Following euthanasia, one half of the excised tissues are fixed in formalin overnight at 4° C. and then processed for histological analysis, the other half are frozen in OCT for processing as frozen sections. The samples for histological analysis are cut from the center of the wound. Area removed spans the width of the wound and include 2-3 mm of the healthy surrounding tissue. There are at least two sections (~2 cm×3 mm) removed from each tissue collected for histological analysis. All histological H&E and trichrome staining are performed as described for the rat model. Immunohistological analysis on frozen samples are carried out using pig specific primary antibodies to the same antigens described in the rat study.

Compare optimal treatments identified in rat studies #3.1-3.5 in a large animal pig model (20 pigs): In this study, pigs are given 5 different treatments (3 wounds per animal of each treatment with a different treatment extra for each animal): A. The optimal delivery system for BCF5-5; B. The optimal delivery system for BCF9-4; C. Whole WSsoy electrospun scaffold; D. The combination of BCF5-5 and BCF9-4 delivery systems; E. Untreated. All groups have the same wound treatments described here. Group 1 (n=5 pigs): Sacrifice 28 days after treatment. The extent of wound healing for each treatment is analyzed. Group 2 (n=5 pigs): Sacrifice 3 days after treatment. Group 3 (n=5 pigs): Sacrifice 7 days after treatment. Group 4 (n=5 pigs): Sacrifice 14 days after treatment.

The experiments presented herein examine whether inclusion of BCF5-5 and BCF9-4 alone or in combination enhance cutaneous wound healing in these large animal models as seen by enhanced re-epithelialization compared to non-treated controls. An alternative to gelatin/BCF5-5 hydrogels would be to incorporate BCF5-5 in a PEG hydrogel system that has been studied with soy and the PEG has been shown to have no biological activity (Snyders, R., et al., 2007, *J Biomed Mater Res A* 83, 88-97). If BCF9-4 cannot be electrospun on its own, it can be co-electrospin it with PGE and use the optimal co-spun scaffold in the studies of synergistic effect. Further experiments can include inhibition studies, such as dosing the rats with VLO5 to inhibit the activity of BCF9-4.

If problems are encountered with excessive background fluorescence, colorimetric staining techniques (HRP, AP, etc.) can be employed, using the appropriate Vector ABC kits.

Example 5: Bioactive Proteins in WSsoy

Each of the fractions (Fraction 5 (F5) and Fraction 9 (F9)) have been further purified to yield smaller protein fractions. Of these, bioactive subfractions were identified using the same assays that identified the bioactivity in F5 and F9 (FIG. 14 shows the bioactivity of the F9 subfractions). These bioactive subfractions and non-active subfractions were subjected to proteomic analysis via SDS-PAGE.

The proteomic analysis of F9 (FIG. 17) suggests a similarity to β-conglycinin. Specifically, the highest identity of the active fractions was with the β-conglycinin alpha' (prime) chain (out of the three chains) (Maruyama, N., et al., 1998, *Eur J Biochem* 258, 854-862-Fig. FIG. 12 depicts overlapping areas of sequence of β-conglycinin alpha' with peptides from proteomics that are in red. The most important factor is that in the sequence of β-conglycinin alpha' there is present an LDV motif (highlighted in yellow, FIG. 12). This is one of the best characterized biologically active motifs, which is present in the CS-1 fragment of fibronectin (Komoriya, A., et al., 1991, *J Biol Chem* 266, 15075-15079; Yokosaki, Y., et al., 1998, *J Biol Chem* 273, 11423-11428; Keinan, O., et al., 2014, *J Cell Sci* 127, 4740-4749). It was characterized as a binding site for α4β1 integrin. α4β1 and α9β1 integrins are very similar and they share several ligands. The CS-1 sequence is included in FIG. 12 in green, marking LDV.

CS-1, which contains the LDV (EILDVPST) sequence (SEQ ID NO.: 1), was purchased and tested in a cell adhesion assay. LN18 cells transfected with the α9 integrin subunit (α9LN18) were used in this assay. Immobilized F9 fraction and recombinant VCAM-1 were used as ligands for α9β1 integrin. The EILDVPST peptide (SEQ ID NO.: 1) completely inhibited adhesion of these cells to both ligands at concentrations around 500 μM. This is the first proof that the LDV motif present in β-conglycinin alpha' is a binding site for α9β1 integrin. This motif's presence in soy proteins has never been published as biologically active. Next steps include synthesizing a peptide that resembles CS-1 peptide from β-conglycinin alpha' (RDLDVFLS) (SEQ ID NO.: 2), which will be tested as an inhibitor of binding of α9β1 integrin to F9 and to VCAM-1 in a cell adhesion assay using cells expressing this integrin, as well as in an ELISA using purified α9β1 integrin. This strategy will confirm that the LDV motif present in soy β-conglycinin alpha' is a binding site for α9β1 integrin.

The proteomic analysis of Fraction 5 suggests that the active Bioactive Component Fraction BCF5-5 can indicate possible candidates for active protein (FIG. 16). The results from Bioactive Component Fraction BCF5-4, which is inactive, support the elimination of band C from consideration due to having similar peptide sequences (FIG. 16). Of the remaining bands, 10 peptides were identified with potential activity for further studies.

Example 5: WSsoy Matrices Enhance the Healing of Dermal Wounds

WSsoy was tested as a wet composition and as a dry composition that was sprinkled onto the wet wound surface for self-assembly in situ to forming a wound-dressing matrix. Histological stains (FIG. 18A, FIG. 18C, FIG. 18E, and FIG. 18G are H&E; FIG. 18B, FIG. 18D, FIG. 18F, and FIG. 18H are picrosirius red, a collagen stain) of tissue show robust and complex re-epithelialization and regeneration of appendages (hair follicles, sweat glands) concomitant with re-organization of the collagen in the extracellular matrix (ECM), while the untreated wounds show formation of an immature epithelial layer only and very little collagen deposition.

Example 6: Biocompatibility, Toxicity, Safety, and Tolerability of WSsoy In Vitro and In Vivo Cytotoxicity is assessed in vitro by measuring adhesion, proliferation, and migration of cultured human dermal cells (endothelial cells, fibroblasts, and keratinocytes, as previously described (Du L et al., Wound Repair and Regeneration, 2012, 20:904-910; Lin L et al., Journal of Tissue Engineering and Regenerative Medicine, 2013, 7:994-1008; Ribeiro M P et al., Wound Repair and Regeneration, 2009, 17:817-824; Vandenbulcke K et al., The International Journal of Lower Extremity Wounds, 2006, 5:109-114) in the presence of various concentrations of WSsoy. In brief, fibroblasts, endothelial cells, and keratinocytes are resuspended in their respective cell culture media together with increasing concentrations of WSsoy (0, 0.1-200 mg/mL), corresponding to and exceeding the doses to be tested in vivo. Initial cell adhesion is measured by assessing the fraction of cells adhering in 30 minutes in the absence or presence of WSsoy (Lecht S et al., Biochimica et Biophysica Acta, 2015, 1850:1169-1179), cell proliferation is measured continually over a 7 day period using the AlamarBlue assay (Lin L et al., Journal of Tissue Engineering and Regenerative Medicine, 2013, 7:994-1008), cell migration is evaluated using an established in vitro wound healing assay (Ventresca E M et al., Cellular Signaling, 2015, 27:1225-1236).

For the in vivo safety and tolerability studies, increasing doses of WSsoy are applied to a model of delayed wound healing (splinted full thickness wounds 1 cm in diameter) in "normal" male hairless Sprague-Dawley rats (Carlson M A et al., Matrix Biology, 2004, 23:243-250). The majority of the preliminary studies were carried out with 10 mg soy protein/wound; the maximum amount of soy applied to each wound did not exceed 25 mg/wound.

The experiments examine three separate aims: the safety and tolerability of increasing doses of WSsoy delivered as a wet WSsoy composition, as a dry WSsoy composition, and in the case of the wet WSsoy composition, the effect of matrix thickness upon a constant dose. In all cases, the animals are followed for up to 4 weeks post-surgery, with behavior and weight monitored every other day. Blood and urine samples are taken weekly to assess, respectively, blood cell count and general/liver toxicity, as well as urinary excretion/clearance (using sensitivity soy-specific HPLC techniques), following FDA guidelines (Lee M H et al., Tissue Engineering Part B, Reviews, 2010, 16:41-54). At the end of the study (after 4 weeks), animals are sacrificed. The lesion site and the surrounding "healthy" tissue are evaluated for signs of continued presence of inflammatory/immune cells by conventional histopathology methods. Internal organs (e.g., lung, liver, kidney, brain) are visually inspected for gross lesions (emboli) and assessed by routine H&E histology.

To test increasing WSsoy concentration, 0.2 mL of wet WSsoy compositions comprising 1.25-25% WSsoy in neutral PBS (equivalent to ca. 2.5-50 mg WSsoy) is applied, which according to preliminary data generates a ca. 250 μm thin, uniform wound matrix. The safety of 2.5, 5, 10, 25, and 50 mg WSsoy/wound is tested for a total of 5 samples (25 animals). The same amounts of dry WSsoy powder are aseptically applied (sprinkle and aerosolized) onto moistened wounds to allow for self-assembly of matrices of various concentrations (25 animals). Another set of wounds are covered with the wet WSsoy composition (made of 15% WSsoy) of various thicknesses (1, 2.5, 5 mm, equivalent to the thickness of, respectively, an electrospun scaffold, half-thickness, and full thickness wounds), in analogy to the study design testing a FDA 510(k) approved collagen-glycosaminoglycan (Integra™) wound dressing (15 animals) (Heit Y I et al., Plastic and Reconstructive Surgery, 2013, 132:767e-776e).

Amongst the small animal models for dermal wound healing (Birch M et al., Methods in Molecular Medicine, 2005, 117:223-235), the splinted full thickness excisional wound in rodents (Carlson M A et al., Matrix Biology, 2004, 23:243-250; Galiano R D et al., Wound Repair Regen, 2004, 12:485-492) is well established as a model for delayed wound healing by epithelialization rather than by contraction (Har-el Y et al., Biomedical Engineering Society Annual Meeting, San Antonio, TX, 2014). Each rat receives dorsally 2 full excisional wounds that are 1 cm in diameter. One wound is treated with a wet WSsoy composition; the contralateral side is treated either with the Integra™ Matrix, or left untreated. All wounds and the surrounding skin are covered with Tegaderm to minimize infection.

The safety and toxicity experiments are endpoint experiments that are terminated after 4 weeks, while other studies are time-course studies to study in more detail the wet WSsoy-enhanced re-epithelialization appendage regeneration over time. Early and late time points are examined to analyze histologically how these treatments modulate the inflammatory response, re-epithelialization and vascularization compared to controls. After euthanasia, the wounded/healing skin and surrounding healthy tissue is collected and processed for routine histology and frozen sections (Har-el Y et al., Wound Medicine, 2014, 5:9-15). Thin paraffin embedded sections (5 μm) are stained with Hematoxylin & Eosin, Masson's Trichrome and Picrosirius Red (ECM recovery, specifically collagen). Immunohistochemistry (IHC) is performed on the sections to determine the extent of inflammation/immune response, vascularization and re-epithelialization (Mondrinos M J et al., Tissue Engineering, 2006, 12:717-728; Mondrinos M J et al., American Journal of Physiology Lung Cellular and Molecular Physiology, 2007, 293:L639-650; Mondrinos M J et al., Tissue Engineering Part A, 2008, 14:361-368). No cytotoxicity is expected in vitro; neither are overt toxicity or adverse immune reactions expected when WSsoy is applied topically as a wound matrix in vivo (Har-el Y et al., Wound Medicine, 2014, 5:9-15; Lin L et al., Journal of Tissue Engineering and Regenerative Medicine, 2013, 7:994-1008).

Example 7: Measuring WSsoy Stability in Serum

The purpose of this study is to establish the stability of WSsoy when exposed to serum/wound exudate. The rationale is to assess the rate of proteolytic degradation of WSsoy matrices of various thicknesses and to determine whether the potential (rapid) degradation of WSsoy warrants periodic re-application during the treatment span. Serum stability testing of WSsoy in vitro is an important component of any POC study and will be carried out in an experimental setting that realistically mimics the milieu in diabetic wounds in vivo. This study measures, for up to 4 weeks, the degradation/stability of WSsoy matrices of various thicknesses (0.25-1 mm) in culture medium containing 50% serum from normal and diabetic rats in the presence or absence of polymorphonuclear leukocytes (PMNs, $10^6$ cells/mL, approximating normal PMN count), from normal and diabetic rats. PMNs are prepared following established protocols (Yuli I et al., European Journal of Biochemistry/FEBS, 1991, 201:421-430) and activated by inflammatory cytokines (e.g. IL-1). This system mimics some of the earliest invading leukocytes that release proteolytic enzymes and may attack the WSsoy. Degradation is initially quantified by measuring the reduction in size (shrinkage) of the WSsoy matrices using an automated x-y stage in an inverted phase/fluorescent cell culture microscope (EVOS). Subsequently, in select cases (maximal and minimal effects) soy degradation products in the supernatants are analyzed using capillary C18 HPLC separation and specific immunoassays (Brandon D L et al., Journal of Agricultural and Food Chemistry, 2002, 50:6635-6642). The injectable WSsoy matrix is expected to be biodegradable and even the thickest WSsoy matrix will degrade in 4 weeks or less (Har-el Y et al., Wound Medicine, 2014, 5:9-15; Lin L et al., Journal of Tissue Engineering and Regenerative Medicine, 2013, 7:994-1008). Histology images of frozen sections from preliminary studies show only remnants of the WSsoy matrices 14 days post-surgery.

Example 8: Determination of Optimally Effective SWM Formulation

The purpose of this study is to identify the formulation/embodiment of WSsoy that optimally enhances re-epithelialization and regeneration of appendages in full-thickness excisional wounds in "normal" rats. Building on endpoint results from prior studies, the effects of an optimally tolerable and efficacious concentration of WSsoy is evaluated in a time-dependent manner on the kinetics of delayed wound healing in a "normal" rat model. The first formulation delivers wet WSsoy compositions of an optimal concentration/thickness as established in previous studies. The second formulation delivers the same amount of dry WSsoy powder by sprinkling/aerosolizing controlled amounts of dry WSsoy onto the moistened wound. A commercially available wound matrix such as Integra™ acts as a positive control.

A single effective dose of the wet WSsoy composition is applied as 0.5 mL (25 mg WSsoy), equivalent to half-thickness layer of gel-like injectable matrices (prepared as 50 mg/mL), following the protocol for a similar Integra™ product (Heit Y I et al., Plastic and Reconstructive Surgery, 2013, 132:767e-776e). Each animal receives dorsally 2 wounds that are 1 cm in diameter. One wound is treated with wet WSsoy, the contralateral side treated either with the Integra™ matrix or left untreated and covered with Tegaderm only. Wound healing is evaluated on days 3, 7, 14, 21, and 28. 5 animals are used per time point for a total of 25 animals.

Following the same rationale, 25 mg dry WSsoy powder is sprinkled/aerosolized onto one pre-moistened wound on each "normal" rat. The contralateral side is treated either with Integra™ matrix or left untreated and covered with Tegaderm only. Wound healing is evaluated on days 3, 7, 14, 21, and 28. 5 animals are used per time point for a total of 25 animals. In total, 55 animals are used, including an excess of 10% to account for possible mortality and illness.

The study is expected to validate and extend the endpoint data obtained in prior studies and provide insight into the accelerated kinetics and enhanced quality of wound healing as induced by WSsoy. WSsoy is also expected to be equivalent if not better than the comparable commercial Integra™ product.

Example 9: WSsoy for Enhancing Diabetic Wound Healing in Animal Models

Diabetic foot ulcers (DFUs), venous leg ulcers (VLUs) and other diabetic complications are most frequently encountered in patients with late onset type 2 diabetes (T2D), who are in most cases also obese. Thus, the genetically diabetic Zucker diabetic fatty (ZDF) rat is used, which in many aspects mimics the progression of human T2D. Specifically, wounds in ZDF rats heal considerably slower than in other rat models of diabetes (e.g., Streptozotocin induced T2D model, or syngeneic "normal controls") (Michaels J T et al., Wound Repair and Regeneration, 2007, 15:665-670). ZDF rats are therefore ideal to initially demonstrate in a small animal model the beneficial effects of any treatment regimen in terms of accelerating wound closure and enhancing the healing/regeneration process. While the pig is recognized as an excellent general model for human disease (Sullivan T P et al., Wound Repair and Regeneration, 2001, 9:66-76), especially for dermal wound healing (Seaton M et al., ILAR Journal, 2015, 56:127-138), there is no suitable genetic porcine model for T2D. Instead, the Streptozotocin (STZ) induced diabetic pig model has been shown to exhibit delayed wound healing compared to non-diabetic control pigs (Velander P et al., Wound Repair and Regeneration, 2008, 16:288-293).

Experiments on ZDF rats are carried out as described previously using the most efficacious embodiment of WSsoy. The same treatment groups from Example 4 with the optimally tolerable/efficacious dose from Example 2 are used. Control animals will be the (syngeneic) ZDF lean rats, which are not diabetic. As with the rat studies, a one dose/delivery method for the WSsoy is used for the pig studies. Using Yorkshire pigs (ca. 60 kg), diabetes is induced as described and validated by measuring elevated glucose levels (Velander P et al., Wound Repair and Regeneration, 2008, 16:288-293). Once the animals are diabetic, sixteen full thickness wounds (3 cm×3 cm×1 cm) are excised dorsally in two rows of 4 on each side (Har-el Y et al., Wound Medicine, 2014, 5:9-15). WSsoy is applied to the wounds at the optimally chosen dose/application method extrapolated to the significantly large size of the wounds in pigs (9 $cm^2$) vs. rats (1.7 $cm^2$). Control wounds do not have any wound dressing applied. Each wound is secured individually with occlusive Tegaderm dressing and the whole area is bandaged. Due to the large number of wounds that can be applied to each pig, it is possible to create wounds of multiple time points in each pig, allowing for each pig to be its own control. Wounds are created at three different time points, and the pig is sacrificed and tissue is collected on the same day (Har-el Y et al., Wound Medicine, 2014, 5:9-15). Surgeries are performed 4 weeks, 2 weeks, and 3 days prior to tissue harvesting, ensuring the time points. Tissue is harvested and analyzed as described in Example 2. 4 pigs are used; 2 with STZ-induced diabetes and two healthy control pigs. It is expected that treatment of porcine wounds with WSsoy will enhance cutaneous wound healing. Given that wound healing in diabetic animals is significantly delayed, it is also expected that there will be certain acceleration of the healing process.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for promoting wound healing and tissue regeneration in a subject in need thereof, the method comprising administering a composition to a treatment site on the subject, the composition comprising a bioactive peptide component of a soy protein isolate wherein the bioactive peptide component consists of:

a) SEQ ID NOs: 34, 35, 37, and 38; or b) SEQ ID NOs: 4, 5, and 39-64.

2. A method of treating a wet wound in a subject in need thereof, the method comprising applying an effective amount of a dry composition comprising purified water-soluble soy protein isolate (WSsoy) to the wet wound on the subject, wherein the dry WSsoy self-assembles into a semi-liquid matrix upon contacting moisture in the wet wound and wherein the purified WSsoy consists of:

a) SEQ ID NOs: 34, 35, 37, and 38; or b) SEQ ID NOs: 4, 5, and 39-64.

3. The method of claim 2, wherein the amount of dry WSsoy is between 1 and 200 mg per 1 $cm^2$ of wound.

4. The method of claim 2, wherein application of the dry WSsoy comprises a thickness between 50 and 5000 μm.

* * * * *

SEQUENCE LISTING

```
<160> NUMBER OF SEQ ID NOS: 64

<210> SEQ ID NO 1
<211> LENGTH: 8
<212> TYPE: PRT
<213> ORGANISM: Artificial Sequence
<220> FEATURE:
<223> OTHER INFORMATION: LDV

<400> SEQUENCE: 1

Glu Ile Leu Asp Val Pro Ser Thr
1               5


<210> SEQ ID NO 2
<211> LENGTH: 8
<212> TYPE: PRT
<213> ORGANISM: Artificial Sequence
<220> FEATURE:
<223> OTHER INFORMATION: CS-1

<400> SEQUENCE: 2

Arg Asp Leu Asp Val Phe Leu Ser
1               5


<210> SEQ ID NO 3
<211> LENGTH: 559
<212> TYPE: PRT
<213> ORGANISM: Artificial Sequence
<220> FEATURE:
<223> OTHER INFORMATION: beta-conglycinin subunit alpha, partial

<400> SEQUENCE: 3

Val Glu Glu Glu Glu Glu Cys Glu Glu Gly Gln Ile Pro Arg Pro Arg
1               5                   10                  15

Pro Gln His Pro Glu Arg Glu Arg Gln Gln His Gly Glu Lys Glu Glu
            20                  25                  30

Asp Glu Gly Glu Gln Pro Arg Pro Phe Pro Phe Pro Arg Pro Arg Gln
        35                  40                  45

Pro His Gln Glu Glu Glu His Glu Gln Lys Glu Glu His Glu Trp His
    50                  55                  60

Arg Lys Glu Glu Lys Glu Gly Gly Lys Gly Ser Glu Glu Glu Gln Asp
65                  70                  75                  80

Glu Arg Glu His Pro Arg Pro His Gln Pro His Gln Lys Glu Glu Glu
                85                  90                  95

Lys His Glu Trp Gln His Lys Gln Glu Lys His Gln Gly Lys Glu Ser
            100                 105                 110
```

```
Glu Glu Glu Glu Glu Asp Gln Asp Glu Asp Glu Glu Gln Asp Lys Glu
        115                 120                 125

Ser Gln Glu Ser Glu Gly Ser Glu Ser Gln Arg Glu Pro Arg Arg His
    130                 135                 140

Lys Asn Lys Asn Pro Phe His Phe Asn Ser Lys Arg Phe Gln Thr Leu
145                 150                 155                 160

Phe Lys Asn Gln Tyr Gly His Val Arg Val Leu Gln Arg Phe Asn Lys
                165                 170                 175

Arg Ser Gln Gln Leu Gln Asn Leu Arg Asp Tyr Arg Ile Leu Glu Phe
            180                 185                 190

Asn Ser Lys Pro Asn Thr Leu Leu Leu Pro His His Ala Asp Ala Asp
        195                 200                 205

Tyr Leu Ile Val Ile Leu Asn Gly Thr Ala Leu Leu Thr Leu Val Asn
    210                 215                 220

Asn Asp Asp Arg Asp Ser Tyr Asn Leu Gln Ser Gly Asp Ala Leu Arg
225                 230                 235                 240

Val Pro Ala Gly Thr Thr Tyr Tyr Val Val Asn Pro Asp Asn Asp Glu
                245                 250                 255

Asn Leu Arg Met Ile Thr Leu Ala Ile Pro Val Asn Lys Pro Gly Arg
            260                 265                 270

Phe Glu Ser Phe Phe Leu Ser Ser Thr Gln Ala Gln Gln Ser Tyr Leu
        275                 280                 285

Gln Gly Phe Ser Lys Asn Ile Leu Glu Ala Ser Tyr Asp Thr Lys Phe
    290                 295                 300

Glu Glu Ile Asn Lys Val Leu Phe Gly Arg Glu Glu Gly Gln Gln Gln
305                 310                 315                 320

Gly Glu Glu Arg Leu Gln Glu Ser Val Ile Val Glu Ile Ser Lys Lys
                325                 330                 335

Gln Ile Arg Glu Leu Ser Lys His Ala Lys Ser Ser Ser Arg Lys Thr
            340                 345                 350

Ile Ser Ser Glu Asp Lys Pro Phe Asn Leu Arg Ser Arg Asp Pro Ile
        355                 360                 365

Tyr Ser Asn Lys Leu Gly Lys Leu Phe Glu Ile Thr Pro Glu Lys Asn
    370                 375                 380

Pro Gln Leu Arg Asp Leu Asp Val Phe Leu Ser Val Val Asp Met Asn
385                 390                 395                 400

Glu Gly Ala Leu Phe Leu Pro His Phe Asn Ser Lys Ala Ile Val Val
                405                 410                 415

Leu Val Ile Asn Glu Gly Glu Ala Asn Ile Glu Leu Val Gly Ile Lys
            420                 425                 430

Glu Gln Gln Gln Arg Gln Gln Gln Glu Phe Gln Pro Leu Glu Val Arg
        435                 440                 445

Lys Tyr Arg Ala Glu Leu Ser Glu Gln Asp Ile Phe Val Ile Pro Ala
    450                 455                 460

Gly Tyr Pro Val Val Val Asn Ala Thr Ser Asp Leu Asn Phe Phe Ala
465                 470                 475                 480

Phe Gly Ile Asn Ala Glu Asn Asn Gln Arg Asn Phe Leu Ala Gly Ser
                485                 490                 495

Lys Asp Asn Val Ile Ser Gln Ile Pro Ser Gln Val Gln Glu Leu Ala
            500                 505                 510

Phe Pro Gly Ser Ala Lys Asp Ile Glu Asn Leu Ile Lys Ser Gln Ser
        515                 520                 525
```

```
Glu Ser Tyr Phe Val Asp Ala Gln Pro Gln Gln Lys Glu Glu Gly Asn
    530                 535                 540

Lys Gly Arg Lys Gly Pro Leu Ser Ser Ile Leu Arg Ala Phe Tyr
545                 550                 555


<210> SEQ ID NO 4
<211> LENGTH: 114
<212> TYPE: PRT
<213> ORGANISM: Artificial Sequence
<220> FEATURE:
<223> OTHER INFORMATION: BCF9-4

<400> SEQUENCE: 4

Ser Gln Gln Leu Gln Asn Leu Arg Asp Ser Tyr Asn Leu Gln Ser Gly
1               5                   10                  15

Asp Ala Leu Arg Val Pro Ala Gly Thr Thr Tyr Tyr Val Val Asn Pro
            20                  25                  30

Asp Asn Asp Glu Asn Leu Arg Met Ile Thr Leu Ala Ile Pro Val Asn
        35                  40                  45

Lys Pro Gly Arg Asn Ile Leu Glu Ala Ser Tyr Asp Thr Lys Val Leu
    50                  55                  60

Phe Gly Arg Glu Glu Gly Gln Gln Gln Gly Glu Glu Arg Thr Ile Ser
65                  70                  75                  80

Ser Glu Asp Lys Pro Phe Asn Leu Arg Asp Glu Leu Pro Gln Leu Val
                85                  90                  95

Thr Leu Pro His Pro Ser Leu His Gly Pro Glu Ile Leu Asp Val Pro
            100                 105                 110

Ser Thr


<210> SEQ ID NO 5
<211> LENGTH: 37
<212> TYPE: PRT
<213> ORGANISM: Artificial Sequence
<220> FEATURE:
<223> OTHER INFORMATION: BCF9-4

<400> SEQUENCE: 5

Leu Gln Ser Gly Asp Ala Leu Arg Asn Ile Leu Glu Ala Ser Tyr Asp
1               5                   10                  15

Thr Lys Phe Glu Glu Ile Asn Lys Lys Thr Ile Ser Ser Glu Asp Lys
            20                  25                  30

Pro Phe Asn Leu Arg
        35


<210> SEQ ID NO 6
<211> LENGTH: 25
<212> TYPE: PRT
<213> ORGANISM: Artificial Sequence
<220> FEATURE:
<223> OTHER INFORMATION: CS-1

<400> SEQUENCE: 6

Asp Glu Leu Pro Gln Leu Val Thr Leu Pro His Pro Ser Leu His Gly
1               5                   10                  15

Pro Glu Ile Leu Asp Val Pro Ser Thr
            20                  25


<210> SEQ ID NO 7
<211> LENGTH: 22
<212> TYPE: PRT
<213> ORGANISM: Artificial Sequence
```

```
<220> FEATURE:
<223> OTHER INFORMATION: BCF5-4A

<400> SEQUENCE: 7

Gln His Gly Asn Thr Gly Gly Leu Tyr Tyr Gly Thr Asp Thr Ala Asp
1               5                   10                  15

Thr Gly Thr Gly Pro Arg
            20


<210> SEQ ID NO 8
<211> LENGTH: 9
<212> TYPE: PRT
<213> ORGANISM: Artificial Sequence
<220> FEATURE:
<223> OTHER INFORMATION: BCF5-4A

<400> SEQUENCE: 8

Val Gly Ala Thr Val Met Ile Asn Ile
1               5


<210> SEQ ID NO 9
<211> LENGTH: 14
<212> TYPE: PRT
<213> ORGANISM: Artificial Sequence
<220> FEATURE:
<223> OTHER INFORMATION: BCF5-4A

<400> SEQUENCE: 9

Tyr Tyr Gly Thr Asn Thr Ala Asp Thr Gly Thr Gly Pro Arg
1               5                   10


<210> SEQ ID NO 10
<211> LENGTH: 10
<212> TYPE: PRT
<213> ORGANISM: Artificial Sequence
<220> FEATURE:
<223> OTHER INFORMATION: BCF5-4A

<400> SEQUENCE: 10

His Ala Ala Trp Thr Tyr Val Ala Thr Arg
1               5                   10


<210> SEQ ID NO 11
<211> LENGTH: 13
<212> TYPE: PRT
<213> ORGANISM: Artificial Sequence
<220> FEATURE:
<223> OTHER INFORMATION: BCF5-4B

<400> SEQUENCE: 11

Gln Gly Glu Thr Val Val Pro Gly Gly Thr Gly Gly Lys
1               5                   10


<210> SEQ ID NO 12
<211> LENGTH: 10
<212> TYPE: PRT
<213> ORGANISM: Artificial Sequence
<220> FEATURE:
<223> OTHER INFORMATION: BCF5-4B

<400> SEQUENCE: 12

Lys Val Asp Glu Tyr Gly Asn Val Glu Lys
1               5                   10


<210> SEQ ID NO 13
<211> LENGTH: 14
```

<212> TYPE: PRT
<213> ORGANISM: Artificial Sequence
<220> FEATURE:
<223> OTHER INFORMATION: BCF5-4B

<400> SEQUENCE: 13

His His Gly Thr Thr Gly Val Tyr Gly Ile Asp Thr Asp Arg
1 5 10

<210> SEQ ID NO 14
<211> LENGTH: 20
<212> TYPE: PRT
<213> ORGANISM: Artificial Sequence
<220> FEATURE:
<223> OTHER INFORMATION: BCF5-4B

<400> SEQUENCE: 14

Gln Thr Asp Glu Tyr Gly Asn Pro Val His Ala Ala Ser Val Thr Tyr
1 5 10 15

Val Ala Thr Arg
20

<210> SEQ ID NO 15
<211> LENGTH: 22
<212> TYPE: PRT
<213> ORGANISM: Artificial Sequence
<220> FEATURE:
<223> OTHER INFORMATION: BCF5-4B

<400> SEQUENCE: 15

Gln His Gly Asn Ile Gly Gly Pro Tyr Tyr Gly Thr Asn Thr Ala Asp
1 5 10 15

Thr Gly Thr Gly Pro Arg
20

<210> SEQ ID NO 16
<211> LENGTH: 7
<212> TYPE: PRT
<213> ORGANISM: Artificial Sequence
<220> FEATURE:
<223> OTHER INFORMATION: BCF5-4B

<400> SEQUENCE: 16

Gln Cys Ala His Val Cys Arg
1 5

<210> SEQ ID NO 17
<211> LENGTH: 7
<212> TYPE: PRT
<213> ORGANISM: Artificial Sequence
<220> FEATURE:
<223> OTHER INFORMATION: BCF5-4B

<400> SEQUENCE: 17

Cys Phe Cys Ser Arg Pro Cys
1 5

<210> SEQ ID NO 18
<211> LENGTH: 10
<212> TYPE: PRT
<213> ORGANISM: Artificial Sequence
<220> FEATURE:
<223> OTHER INFORMATION: BCF5-4B

<400> SEQUENCE: 18

Ser Asp Gly Phe Ile Gly Gly Gln Cys Arg

```
1               5                   10


<210> SEQ ID NO 19
<211> LENGTH: 15
<212> TYPE: PRT
<213> ORGANISM: Artificial Sequence
<220> FEATURE:
<223> OTHER INFORMATION: BCF5-4B

<400> SEQUENCE: 19

Gln Ile Val Thr Val Glu Gly Gly Leu Ser Val Ile Ser Pro Lys
1               5                   10                  15


<210> SEQ ID NO 20
<211> LENGTH: 16
<212> TYPE: PRT
<213> ORGANISM: Artificial Sequence
<220> FEATURE:
<223> OTHER INFORMATION: BCF5-4B

<400> SEQUENCE: 20

Gln Gln His Asp Ala Ile Gly Val Tyr Pro Gly Ile Asp Ile Gly Arg
1               5                   10                  15


<210> SEQ ID NO 21
<211> LENGTH: 22
<212> TYPE: PRT
<213> ORGANISM: Artificial Sequence
<220> FEATURE:
<223> OTHER INFORMATION: BCF5-4B

<400> SEQUENCE: 21

Gln His Gly Asn Thr Gly Gly Leu Tyr Tyr Gly Thr Asp Thr Ala Asp
1               5                   10                  15

Thr Gly Thr Gly Pro Arg
            20


<210> SEQ ID NO 22
<211> LENGTH: 8
<212> TYPE: PRT
<213> ORGANISM: Artificial Sequence
<220> FEATURE:
<223> OTHER INFORMATION: BCF5-4C

<400> SEQUENCE: 22

Glu Leu Met Asn Leu Ala Ile Arg
1               5


<210> SEQ ID NO 23
<211> LENGTH: 13
<212> TYPE: PRT
<213> ORGANISM: Artificial Sequence
<220> FEATURE:
<223> OTHER INFORMATION: BCF5-4C

<400> SEQUENCE: 23

Leu Gly Pro Met Ile Gly Cys Asp Leu Ser Ser Asp Asp
1               5                   10


<210> SEQ ID NO 24
<211> LENGTH: 15
<212> TYPE: PRT
<213> ORGANISM: Artificial Sequence
<220> FEATURE:
<223> OTHER INFORMATION: BCF5-4C

<400> SEQUENCE: 24
```

Cys Arg Leu Gly Pro Met Ile Gly Cys Asp Leu Ser Ser Asp Asp
1 5 10 15

<210> SEQ ID NO 25
<211> LENGTH: 7
<212> TYPE: PRT
<213> ORGANISM: Artificial Sequence
<220> FEATURE:
<223> OTHER INFORMATION: BCF5-4D

<400> SEQUENCE: 25

Gln Cys Ala His Val Cys Arg
1 5

<210> SEQ ID NO 26
<211> LENGTH: 7
<212> TYPE: PRT
<213> ORGANISM: Artificial Sequence
<220> FEATURE:
<223> OTHER INFORMATION: BCF5-4D

<400> SEQUENCE: 26

Cys Phe Cys Ser Arg Pro Cys
1 5

<210> SEQ ID NO 27
<211> LENGTH: 10
<212> TYPE: PRT
<213> ORGANISM: Artificial Sequence
<220> FEATURE:
<223> OTHER INFORMATION: BCF5-4D

<400> SEQUENCE: 27

Ser Asp Gly Phe Ile Gly Gly Gln Cys Arg
1 5 10

<210> SEQ ID NO 28
<211> LENGTH: 12
<212> TYPE: PRT
<213> ORGANISM: Artificial Sequence
<220> FEATURE:
<223> OTHER INFORMATION: BCF5-4D

<400> SEQUENCE: 28

Cys Leu Phe Asp Arg Gln Cys Ala His Val Cys Arg
1 5 10

<210> SEQ ID NO 29
<211> LENGTH: 12
<212> TYPE: PRT
<213> ORGANISM: Artificial Sequence
<220> FEATURE:
<223> OTHER INFORMATION: BCF5-4D

<400> SEQUENCE: 29

Ser Met Pro Pro Gln Cys Ser Cys Glu Asp Ile Arg
1 5 10

<210> SEQ ID NO 30
<211> LENGTH: 13
<212> TYPE: PRT
<213> ORGANISM: Artificial Sequence
<220> FEATURE:
<223> OTHER INFORMATION: BCF5-4D

<400> SEQUENCE: 30

```
Cys Leu Asp Thr Asn Asp Phe Cys Tyr Lys Pro Cys Lys
1               5                   10


<210> SEQ ID NO 31
<211> LENGTH: 8
<212> TYPE: PRT
<213> ORGANISM: Artificial Sequence
<220> FEATURE:
<223> OTHER INFORMATION: BCF5-4D

<400> SEQUENCE: 31

Cys Gly Val Asn Ile Pro Tyr Lys
1               5


<210> SEQ ID NO 32
<211> LENGTH: 15
<212> TYPE: PRT
<213> ORGANISM: Artificial Sequence
<220> FEATURE:
<223> OTHER INFORMATION: BCF5-4D

<400> SEQUENCE: 32

Asp Glu Tyr Ser Lys Pro Cys Cys Asp Leu Cys Met Cys Thr Arg
1               5                   10                  15


<210> SEQ ID NO 33
<211> LENGTH: 13
<212> TYPE: PRT
<213> ORGANISM: Artificial Sequence
<220> FEATURE:
<223> OTHER INFORMATION: BCF5-5

<400> SEQUENCE: 33

Leu Gly Pro Met Ile Gly Cys Asp Leu Ser Ser Asp Asp
1               5                   10


<210> SEQ ID NO 34
<211> LENGTH: 12
<212> TYPE: PRT
<213> ORGANISM: Artificial Sequence
<220> FEATURE:
<223> OTHER INFORMATION: BCF5-5

<400> SEQUENCE: 34

Ile Met Asp Asn Gln Ser Glu Gln Leu Glu Gly Lys
1               5                   10


<210> SEQ ID NO 35
<211> LENGTH: 13
<212> TYPE: PRT
<213> ORGANISM: Artificial Sequence
<220> FEATURE:
<223> OTHER INFORMATION: BCF5-5

<400> SEQUENCE: 35

Lys Gln Met Glu Arg Glu Leu Met Asn Leu Ala Ile Arg
1               5                   10


<210> SEQ ID NO 36
<211> LENGTH: 15
<212> TYPE: PRT
<213> ORGANISM: Artificial Sequence
<220> FEATURE:
<223> OTHER INFORMATION: BCF5-5

<400> SEQUENCE: 36

Cys Arg Leu Gly Pro Met Ile Gly Cys Asp Leu Ser Ser Asp Asp
```

```
1               5                   10                  15


<210> SEQ ID NO 37
<211> LENGTH: 16
<212> TYPE: PRT
<213> ORGANISM: Artificial Sequence
<220> FEATURE:
<223> OTHER INFORMATION: BCF5-5

<400> SEQUENCE: 37

Cys Cys Ser Glu Met Ser Glu Leu Lys Ser Pro Ile Cys Gln Cys Lys
1               5                   10                  15


<210> SEQ ID NO 38
<211> LENGTH: 15
<212> TYPE: PRT
<213> ORGANISM: Artificial Sequence
<220> FEATURE:
<223> OTHER INFORMATION: BCF5-5

<400> SEQUENCE: 38

Gln Ile Val Thr Val Glu Gly Gly Leu Ser Val Ile Ser Pro Lys
1               5                   10                  15


<210> SEQ ID NO 39
<211> LENGTH: 8
<212> TYPE: PRT
<213> ORGANISM: Artificial Sequence
<220> FEATURE:
<223> OTHER INFORMATION: BCF9-4

<400> SEQUENCE: 39

Ser Gln Gln Leu Gln Asn Leu Arg
1               5


<210> SEQ ID NO 40
<211> LENGTH: 10
<212> TYPE: PRT
<213> ORGANISM: Artificial Sequence
<220> FEATURE:
<223> OTHER INFORMATION: BCF9-4

<400> SEQUENCE: 40

Asn Ile Leu Glu Ala Ser Tyr Asp Thr Lys
1               5                   10


<210> SEQ ID NO 41
<211> LENGTH: 12
<212> TYPE: PRT
<213> ORGANISM: Artificial Sequence
<220> FEATURE:
<223> OTHER INFORMATION: BCF9-4

<400> SEQUENCE: 41

Asp Ser Tyr Asn Leu Gln Ser Gly Asp Ala Leu Arg
1               5                   10


<210> SEQ ID NO 42
<211> LENGTH: 12
<212> TYPE: PRT
<213> ORGANISM: Artificial Sequence
<220> FEATURE:
<223> OTHER INFORMATION: BCF9-4

<400> SEQUENCE: 42

Thr Ile Ser Ser Glu Asp Lys Pro Phe Asn Leu Arg
1               5                   10
```

<210> SEQ ID NO 43
<211> LENGTH: 13
<212> TYPE: PRT
<213> ORGANISM: Artificial Sequence
<220> FEATURE:
<223> OTHER INFORMATION: BCF9-4

<400> SEQUENCE: 43

Met Ile Thr Leu Ala Ile Pro Val Asn Lys Pro Gly Arg
1 5 10

<210> SEQ ID NO 44
<211> LENGTH: 13
<212> TYPE: PRT
<213> ORGANISM: Artificial Sequence
<220> FEATURE:
<223> OTHER INFORMATION: BCF9-4

<400> SEQUENCE: 44

Lys Thr Ile Ser Ser Glu Asp Lys Pro Phe Asn Leu Arg
1 5 10

<210> SEQ ID NO 45
<211> LENGTH: 15
<212> TYPE: PRT
<213> ORGANISM: Artificial Sequence
<220> FEATURE:
<223> OTHER INFORMATION: BCF9-4

<400> SEQUENCE: 45

Val Leu Phe Gly Arg Glu Glu Gly Gln Gln Gln Gly Glu Glu Arg
1 5 10 15

<210> SEQ ID NO 46
<211> LENGTH: 16
<212> TYPE: PRT
<213> ORGANISM: Artificial Sequence
<220> FEATURE:
<223> OTHER INFORMATION: BCF9-4

<400> SEQUENCE: 46

Asn Ile Leu Glu Ala Ser Tyr Asp Thr Lys Phe Glu Glu Ile Asn Lys
1 5 10 15

<210> SEQ ID NO 47
<211> LENGTH: 19
<212> TYPE: PRT
<213> ORGANISM: Artificial Sequence
<220> FEATURE:
<223> OTHER INFORMATION: BCF9-4

<400> SEQUENCE: 47

Val Pro Ala Gly Thr Thr Tyr Tyr Val Val Asn Pro Asp Asn Asp Glu
1 5 10 15

Asn Leu Arg

<210> SEQ ID NO 48
<211> LENGTH: 8
<212> TYPE: PRT
<213> ORGANISM: Artificial Sequence
<220> FEATURE:
<223> OTHER INFORMATION: BCF9-4

<400> SEQUENCE: 48

Leu Gln Ser Gly Asp Ala Leu Arg

```
1               5


<210> SEQ ID NO 49
<211> LENGTH: 13
<212> TYPE: PRT
<213> ORGANISM: Artificial Sequence
<220> FEATURE:
<223> OTHER INFORMATION: BCF9-4

<400> SEQUENCE: 49

Leu Ile Thr Leu Ala Ile Pro Val Asn Lys Pro Gly Arg
1               5                   10


<210> SEQ ID NO 50
<211> LENGTH: 19
<212> TYPE: PRT
<213> ORGANISM: Artificial Sequence
<220> FEATURE:
<223> OTHER INFORMATION: BCF9-4

<400> SEQUENCE: 50

Val Pro Ser Gly Thr Thr Tyr Tyr Val Val Asn Pro Asp Asn Asn Glu
1               5                   10                  15

Asn Leu Arg


<210> SEQ ID NO 51
<211> LENGTH: 13
<212> TYPE: PRT
<213> ORGANISM: Artificial Sequence
<220> FEATURE:
<223> OTHER INFORMATION: BCF9-4

<400> SEQUENCE: 51

Ile Ser Thr Leu Asn Ser Leu Thr Leu Pro Ala Leu Arg
1               5                   10


<210> SEQ ID NO 52
<211> LENGTH: 19
<212> TYPE: PRT
<213> ORGANISM: Artificial Sequence
<220> FEATURE:
<223> OTHER INFORMATION: BCF9-4

<400> SEQUENCE: 52

Ala Ile Pro Ser Glu Val Leu Ser Asn Ser Tyr Asn Leu Gly Gln Ser
1               5                   10                  15

Gln Val Arg


<210> SEQ ID NO 53
<211> LENGTH: 17
<212> TYPE: PRT
<213> ORGANISM: Artificial Sequence
<220> FEATURE:
<223> OTHER INFORMATION: BCF9-4

<400> SEQUENCE: 53

Phe Asn Glu Cys Gln Leu Asn Asn Leu Asn Ala Leu Glu Pro Asp His
1               5                   10                  15

Arg


<210> SEQ ID NO 54
<211> LENGTH: 8
<212> TYPE: PRT
<213> ORGANISM: Artificial Sequence
<220> FEATURE:
```

<223> OTHER INFORMATION: BCF9-5

<400> SEQUENCE: 54

Leu Gln Ser Gly Asp Ala Leu Arg
1               5

<210> SEQ ID NO 55
<211> LENGTH: 8
<212> TYPE: PRT
<213> ORGANISM: Artificial Sequence
<220> FEATURE:
<223> OTHER INFORMATION: BCF9-5

<400> SEQUENCE: 55

Ser Pro Gln Leu Gln Asn Leu Arg
1               5

<210> SEQ ID NO 56
<211> LENGTH: 10
<212> TYPE: PRT
<213> ORGANISM: Artificial Sequence
<220> FEATURE:
<223> OTHER INFORMATION: BCF9-5

<400> SEQUENCE: 56

Asn Ile Leu Glu Ala Ser Tyr Asp Thr Lys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: BCF9-5

<400> SEQUENCE: 57

Leu Ile Thr Leu Ala Ile Pro Val Asn Lys Pro Gly Arg
1               5                   10

<210> SEQ ID NO 58
<211> LENGTH: 12
<212> TYPE: PRT
<213> ORGANISM: Artificial Sequence
<220> FEATURE:
<223> OTHER INFORMATION: BCF9-5

<400> SEQUENCE: 58

Thr Ile Ser Ser Glu Asp Lys Pro Phe Asn Leu Arg
1               5                   10

<210> SEQ ID NO 59
<211> LENGTH: 15
<212> TYPE: PRT
<213> ORGANISM: Artificial Sequence
<220> FEATURE:
<223> OTHER INFORMATION: BCF9-5

<400> SEQUENCE: 59

Leu Gln Glu Ser Val Ile Val Glu Ile Ser Lys Glu Gln Ile Arg
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: BCF9-5

-continued

```
<400> SEQUENCE: 60

Val Leu Phe Ser Arg Glu Glu Gly Gln Gln Gln Gly Glu Gln Arg
1               5                   10                  15


<210> SEQ ID NO 61
<211> LENGTH: 19
<212> TYPE: PRT
<213> ORGANISM: Artificial Sequence
<220> FEATURE:
<223> OTHER INFORMATION: BCF9-5

<400> SEQUENCE: 61

Val Pro Ser Gly Thr Thr Tyr Tyr Val Val Asn Pro Asp Asn Asn Glu
1               5                   10                  15

Asn Leu Arg


<210> SEQ ID NO 62
<211> LENGTH: 8
<212> TYPE: PRT
<213> ORGANISM: Artificial Sequence
<220> FEATURE:
<223> OTHER INFORMATION: BCF9-5

<400> SEQUENCE: 62

Ser Gln Gln Leu Gln Asn Leu Arg
1               5


<210> SEQ ID NO 63
<211> LENGTH: 13
<212> TYPE: PRT
<213> ORGANISM: Artificial Sequence
<220> FEATURE:
<223> OTHER INFORMATION: BCF9-5

<400> SEQUENCE: 63

Met Ile Thr Leu Ala Ile Pro Val Asn Lys Pro Gly Arg
1               5                   10


<210> SEQ ID NO 64
<211> LENGTH: 19
<212> TYPE: PRT
<213> ORGANISM: Artificial Sequence
<220> FEATURE:
<223> OTHER INFORMATION: BCF9-5

<400> SEQUENCE: 64

Val Pro Ala Gly Thr Thr Tyr Tyr Val Val Asn Pro Asp Asn Asp Glu
1               5                   10                  15

Asn Leu Arg
```